United States Patent
Martin et al.

(10) Patent No.: US 12,036,339 B2
(45) Date of Patent: *Jul. 16, 2024

(54) NANOFIBER-HYDROGEL COMPOSITES FOR ENHANCED SOFT TISSUE REPLACEMENT AND REGENERATION

(71) Applicant: The Johns Hopkins University, Baltimore, MD (US)

(72) Inventors: Russell Martin, Baltimore, MD (US); Hai-Quan Mao, Baltimore, MD (US); Sashank Reddy, Baltimore, MD (US); Kevin Colbert, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/515,819

(22) Filed: Jul. 18, 2019

(65) Prior Publication Data

US 2020/0069846 A1    Mar. 5, 2020

Related U.S. Application Data

(63) Continuation of application No. PCT/US2019/031638, filed on May 9, 2019.

(60) Provisional application No. 62/669,307, filed on May 9, 2018.

(51) Int. Cl.
| | |
|---|---|
| A61L 27/56 | (2006.01) |
| A61L 27/36 | (2006.01) |
| A61L 27/48 | (2006.01) |
| A61L 27/54 | (2006.01) |

(52) U.S. Cl.
CPC .......... *A61L 27/56* (2013.01); *A61L 27/3633* (2013.01); *A61L 27/48* (2013.01); *A61L 27/54* (2013.01); *A61L 2300/236* (2013.01); *A61L 2300/62* (2013.01); *A61L 2400/06* (2013.01); *A61L 2430/34* (2013.01)

(58) Field of Classification Search
None
See application file for complete search history.

(56) References Cited

U.S. PATENT DOCUMENTS

| | | |
|---|---|---|
| 1,683,347 A | 9/1928 | Gray et al. |
| 1,698,049 A | 1/1929 | Clarke et al. |
| 1,880,560 A | 10/1932 | Webber et al. |
| 1,880,808 A | 10/1932 | Clarke et al. |
| 1,984,147 A | 12/1934 | Malm |
| 2,129,052 A | 9/1938 | Fordyce |
| 3,475,407 A | 10/1969 | Birkenmeyer |
| 3,509,127 A | 4/1970 | Kagan et al. |
| 3,513,155 A | 5/1970 | Birkenmeyer et al. |
| 3,544,551 A | 12/1970 | Kagan et al. |
| 3,617,201 A | 11/1971 | Berni et al. |
| 3,989,816 A | 11/1976 | Rajadhyaksha |
| 4,043,331 A | 8/1977 | Martin et al. |
| 4,316,893 A | 2/1982 | Rajadhyaksha |
| 4,405,616 A | 9/1983 | Rajadhyaksha |
| 4,557,934 A | 12/1985 | Cooper |
| 4,568,343 A | 2/1986 | Leeper et al. |
| 4,582,865 A | 4/1986 | Balazs et al. |
| 4,783,450 A | 11/1988 | Fawzi et al. |
| 4,973,493 A | 11/1990 | Guire |
| 5,258,041 A | 11/1993 | Guire et al. |
| 5,522,879 A | 6/1996 | Scopelianos |
| 5,563,056 A | 10/1996 | Swan et al. |
| 5,637,460 A | 6/1997 | Swan et al. |
| 5,766,710 A | 6/1998 | Turnlund et al. |
| 5,846,558 A | 12/1998 | Nielsen et al. |
| 6,278,018 B1 | 8/2001 | Swan |
| 6,280,474 B1 | 8/2001 | Cassidy et al. |
| 6,488,872 B1 | 12/2002 | Beebe et al. |
| 6,896,904 B2 | 5/2005 | Spiro et al. |
| 6,991,652 B2 | 1/2006 | Burg |
| 7,651,703 B2 | 1/2010 | Cleland et al. |
| 8,183,042 B2 | 5/2012 | Liao et al. |
| 8,691,259 B2 | 4/2014 | Bowman et al. |
| 8,697,044 B2 | 4/2014 | Schroeder et al. |
| 8,790,702 B2 | 7/2014 | Gravett et al. |
| 8,822,676 B2 | 9/2014 | Lebreton |
| 9,334,262 B2 | 5/2016 | Van Epps et al. |
| 10,131,718 B2 | 11/2018 | Karlsson et al. |
| 10,471,181 B2 | 11/2019 | Martin et al. |

(Continued)

FOREIGN PATENT DOCUMENTS

| | | |
|---|---|---|
| AU | 2010203698 B2 | 7/2011 |
| CN | 103333349 A | 10/2013 |

(Continued)

OTHER PUBLICATIONS

KR 2007-0073008 machine translation.*
Yusong, et al., "Mechanical properties of nanohydroxyapatite reinforced poly(vinyl alcohol) gel composites as biomaterial", Journal of Materials Science, Jul. 2007, 42(13):5129-5134.
Zagho, et al., "Recent Overviews in Functional Polymer Composites for Biomedical Applications", Polymers (Basel), Jul. 2018, 10(7):739.
Zhang, et al., "Electrospinning of gelatin fibers and gelatin/PCL composite fibrous scaffolds", Journal of Biomedical Materials Research Part B, Jan. 2005, 72B(1):156-165.
Zhou, et al., "A novel polyacrylamide nanocomposite hydrogel reinforced with natural chitosan nanofibers", Colloids and Surfaces B: Biointerfaces, May 2011, 84(1):155-162.

(Continued)

*Primary Examiner* — David J Blanchard
*Assistant Examiner* — Sarah J Chickos
(74) *Attorney, Agent, or Firm* — Fox Rothschild LLP

(57) ABSTRACT

A composite material can include a gel and at least one nanostructure disposed within the gel. A method for healing a soft tissue defect can include applying a composite material to a soft tissue defect, wherein the composite material includes a gel and a nanostructure disposed within the gel. A method for manufacturing a composite material for use in healing soft tissue defects can include providing a gel and disposing nanofibers within the gel.

20 Claims, 43 Drawing Sheets

Specification includes a Sequence Listing.

(56) References Cited

U.S. PATENT DOCUMENTS

| | | | |
|---|---|---|---|
| 2004/0013626 A1* | 1/2004 | Gref | C08B 37/00 |
| | | | 424/70.13 |
| 2004/0197367 A1 | 10/2004 | Rezania et al. | |
| 2005/0222083 A1 | 10/2005 | Bulpitt et al. | |
| 2006/0273279 A1 | 12/2006 | Kaplan et al. | |
| 2007/0141108 A1 | 6/2007 | Thomas et al. | |
| 2007/0202074 A1 | 8/2007 | Shalaby | |
| 2007/0224277 A1 | 9/2007 | Borbely et al. | |
| 2007/0243259 A1 | 10/2007 | Sung et al. | |
| 2008/0262078 A1* | 10/2008 | Namdeo | A61K 47/10 |
| | | | 514/449 |
| 2009/0163936 A1 | 6/2009 | Yang et al. | |
| 2010/0217403 A1 | 8/2010 | Champion et al. | |
| 2010/0331980 A1 | 12/2010 | Lee et al. | |
| 2011/0117171 A1 | 5/2011 | Melican et al. | |
| 2011/0151011 A1 | 6/2011 | Flynn | |
| 2011/0288199 A1 | 11/2011 | Lowman et al. | |
| 2012/0040461 A1 | 2/2012 | Beachley et al. | |
| 2012/0100185 A1 | 4/2012 | Wen et al. | |
| 2012/0207813 A1 | 8/2012 | Rhee et al. | |
| 2012/0264190 A1 | 10/2012 | Christman et al. | |
| 2012/0267810 A1* | 10/2012 | Mao | B01F 3/0807 |
| | | | 264/11 |
| 2013/0052254 A1 | 2/2013 | Arinzeh et al. | |
| 2013/0230601 A1 | 9/2013 | Itskovitz-eldor et al. | |
| 2013/0244943 A1 | 9/2013 | Yu et al. | |
| 2014/0030315 A1 | 1/2014 | Johnson | |
| 2014/0112990 A1 | 4/2014 | Bencherif et al. | |
| 2015/0105863 A1 | 4/2015 | Zussman et al. | |
| 2016/0083690 A1 | 3/2016 | Birch et al. | |
| 2016/0243281 A1 | 8/2016 | Leach | |
| 2016/0303281 A1 | 10/2016 | Salamone et al. | |
| 2017/0165397 A1 | 6/2017 | Matteuzzi | |
| 2017/0224874 A1 | 8/2017 | Maki et al. | |
| 2017/0333304 A1 | 11/2017 | Artzi et al. | |
| 2018/0050130 A1 | 2/2018 | Jiang et al. | |
| 2018/0064854 A1 | 3/2018 | Hingtgen et al. | |
| 2018/0243480 A1 | 8/2018 | Martin et al. | |
| 2019/0060516 A1 | 2/2019 | Martin et al. | |
| 2019/0175784 A1 | 6/2019 | Lee et al. | |
| 2020/0069846 A1 | 3/2020 | Martin et al. | |
| 2021/0308055 A1 | 10/2021 | Masi | |

FOREIGN PATENT DOCUMENTS

| | | | |
|---|---|---|---|
| GB | 2082665 A | | 3/1982 |
| JP | 2009518498 | | 5/2009 |
| JP | 2014514336 A | | 6/2014 |
| KR | 2007-0073008 | * | 7/2007 |
| KR | 2007-0073008 A | | 7/2007 |
| RU | 2539395 C2 | | 1/2015 |
| RU | 2593790 C2 | | 8/2016 |
| WO | 98/32675 A2 | | 7/1998 |
| WO | 2007/090102 A2 | | 8/2007 |
| WO | 2007/146261 A2 | | 12/2007 |
| WO | 2008/003320 A2 | | 1/2008 |
| WO | 2008/147817 A2 | | 12/2008 |
| WO | 2009/042829 A1 | | 4/2009 |
| WO | 2009/046530 A1 | | 4/2009 |
| WO | 2009/120995 A2 | | 10/2009 |
| WO | 2011/019822 A2 | | 2/2011 |
| WO | 2011/063152 A1 | | 5/2011 |
| WO | 2012/131095 A1 | | 10/2012 |
| WO | WO 2017/031167 | * | 10/2012 |
| WO | 2013/071107 A1 | | 5/2013 |
| WO | 2013/110056 A1 | | 7/2013 |
| WO | 2013/172788 A1 | | 11/2013 |
| WO | 2015/048224 A1 | | 4/2015 |
| WO | 2016/025945 A1 | | 2/2016 |
| WO | 2017/031171 A1 | | 2/2017 |
| WO | 2017/136935 A1 | | 8/2017 |
| WO | 2019/126169 A1 | | 6/2019 |
| WO | 2019/139381 A1 | | 7/2019 |

OTHER PUBLICATIONS

International Search Report and Written Opinion of PCT Application No. PCT/US2016/047288, dated Dec. 12, 2016, 10 pages.

Barreto-Ortiz, et al., "A Novel In Vitro Model for Microvasculature Reveals Regulation of Circumferential ECM Organization by Curvature" PLoS One, Nov. 21, 2013, 8(11): e81061.

Kim, et al., "Fibrous Hyaluronic Acid Hydrogels that Direct MSC Chondrogenesis through Mechanical and Adhesive Cues", Biomaterials, Jul. 2013, 34(22):5571-5580.

Kim, et al., "Tissue Response to Implants of Hyaluronic Acid Hydrogel Prepared by Microbeads", Tissue Engineering and Regenerative Medicine, Feb. 2014, 11(1):32-38.

Korrapati, et al., "Recent Advancements in Nanotechnological Strategies in Selection, Design and Delivery of Biomolecules for Skin Regeneration", Materials Science and Engineering: C, Oct. 2016, 67:747-765.

Lau, et al., "Opportunities for Multicomponent Hybrid Hydrogels in Biomedical Applications", Biomacromolecules, 2015, 16(1)28-42.

Lee, et al., "Enhanced Chondrogenesis of Mesenchymal Stem Cells in Collagen Mimetic Peptide-Mediated Microenvironment", Tissue Engineering: Part A, 2008, 14(11):1843-1851.

Li, et al., "Engineering In Situ Cross-Linkable and Neurocompatible Hydrogels", Journal of Neurotrauma, Aug. 2014, 31(16):1431-1438.

Li, et al., "Nanofiber-hydrogel composite-mediated angiogenesis for soft tissue reconstruction", Science Translation Medicine, 2019, 11(490):1-11.

Lim, et al., "Electrospun scaffolds for stem cell engineering", Advanced Drug Delivery Reviews, Oct. 5, 2009, 61(12):1084-1096.

Lim, et al., "The effect of nanofiber-guided cell alignment on the preferential differentiation of neural stem cells", Biomaterials, Dec. 2010, 31(34):9031-9039.

Loh, et al., "Three-Dimensional Scaffolds for Tissue Engineering Applications: Role of Porosity and Pore Size", Tissue Engineering. Part B, Dec. 2013, 19(6):485-502.

Lotempio, et al., "Breast Reconstruction with SGAP and IGAP Flaps", Plastic and Reconstructive Surgery, Aug. 2010, 126(2):393-401.

Martin, et al., "P-142: Preparation and Characterization of Nanofiber-Loaded Hyaluronic Acid Hydrogel for Soft Tissue Repair", 2014 TERMIS-AM Conference, Tissue Engineering Part A, Abstract only, Dec. 2014, 20(Suppl 1):S1 & S63.

Mochane, et al., "Morphology and Properties of Electrospun PCL and Its Composites for Medical Applications: A Mini Review", Applied Sciences, May 2019, 9(11):2205.

Nam, et al., "Improved Cellular Infiltration in Electrospun Fiber via Engineered Porosity", Tissue Engineering, Sep. 2007, 13(9):2249-2257.

Nicodemus, et al., "Cell Encapsulation in Biodegradable Hydrogels for Tissue Engineering Applications", Tissue Engineering Part B: Reviews, Jun. 2008, 14(2):149-165.

Nie, et al., "IFATS Collection: Combinatorial Peptides Identify ?5?1 Integrin as a Receptor for the Matricellular Protein SPARC on Adipose Stromal Cells", Stem Cells, Oct. 2008, 26(10):2735-2745.

Patel, et al., "Management of Massive Mastectomy Skin Flap Necrosis Following Autologous Breast Reconstruction", Annals of Plastic Surgery, Aug. 2012, 69(2):139-144.

Pei, et al., "Fiber-reinforced scaffolds in soft tissue engineering", Regenerative Biomaterials, Aug. 2017, 4(4):257-268.

Placone, et al., "Human Astrocytes Develop Physiological Morphology and Remain Quiescent in a Novel 3D Matrix", Biomaterials, Feb. 2015, 42:134-143.

Quake, et al., "From Micro- to Nanofabrication with Soft Materials", Science, Nov. 24, 2000, 290 (5496):1536-1540.

Ren, et al., "Enhanced Differentiation of Human Neural Crest Stem Cells Towards Schwann Cell Lineage by Aligned Electrospun Fiber Matrix", Acta biomaterialia, Apr. 2013, 9(8):7727-7736.

Rivet, et al., "Cell infiltration into a 3D electrospun fiber and hydrogel hybrid scaffold implanted in the brain", Biomatter, 2015, 5(1):e1005527-1-e1005527-7.

(56) References Cited

OTHER PUBLICATIONS

Ryu, et al., "Catechol-Functionalized Chitosan/Pluronic Hydrogels for Tissue Adhesives and Hemostatic Materials", Biomacromolecules, May 21, 2011, 12(7):2653-2659.

Saez-Martinez, et al., "New hybrid system: Poly(ethylene glycol) hydrogel with covalently bonded pegylated nanotubes", Journal of Applied Polymer Science, 2011, 120(1):124-132.

Salibian, et al., "Stem Cells in Plastic Surgery: A Review of Current Clinical and Translational Applications", Archives of Plastic Surgery, Nov. 2013, 40(6):666-675.

Seliktar, "Designing Cell-Compatible Hydrogels for Biomedical Applications", Science, Jun. 2012, 336(6085):1124-1128.

Shapiro, et al., "Hydrogel Composite Materials for Tissue Engineering Scaffolds", JOM: the journal of the Minerals, Apr. 2013, 65(4):505-516.

Sheffield, et al., "Application of Composite Hydrogels to Control Physical Properties in Tissue Engineering and Regenerative Medicine", Gels, May 2018, 4(2):51.

Shin, et al., "Engineered ECM-like microenvironment with fibrous particles for guiding 3D-encapsulated hMSC behaviours", Journal of Materials Chemistry B, Feb. 2015, 3(13):2732-2741.

Siddiqui, et al., "PCL-Based Composite Scaffold Matrices for Tissue Engineering Applications", Molecular Biotechnology, Jul. 2018, 60(7):506-532.

Slevin, et al., "Angiogenic Oligosaccharides of Hyaluronan Induce Multiple Signaling Pathways Affecting Vascular Endothelial Cell Mitogenic and Wound Healing Responses", The Journal of Biological Chemistry, Oct. 25, 2002, 277(43):41046-41059.

Sommer, et al., "Multiaxial mechanical properties and constitutive modeling of human adipose tissue: A basis for preoperative simulations in plastic and reconstructive surgery", Acta Biomaterialia, Nov. 2013, 9(11):9036-9048.

Su, "Thiol-Mediated Chemoselective Strategies for In Situ Formation of Hydrogels", Gels, 2018, 4(3):72.

Tate, et al., "Fibronectin Promotes Survival and Migration of Primary Neural Stem Cells Transplanted Into the Traumatically Injured Mouse Brain", Cell Transplantation, 2002, 11(3):283-295.

Tiwari, et al., "Biodegradable Hydrogels Based on Novel Photopolymerizable Guar Gum-Methacrylate Macromonomers for In Situ Fabrication of Tissue Engineering Scaffolds", Acta Biomaterialia, 2009, 5(9):3441-3452.

Toh, et al., "Advances in hydrogel delivery systems for tissue regeneration", Materials Science and Engineering: C, Dec. 2014, 45:690-697.

Trochon, et al., "Evidence of involvement of CD44 in endothelial cell proliferation, migration and angiogenesis in vitro", International Journal of Cancer, May 1996, 66(5):664-668.

Tsoi, et al., "Safety of Tissue Expander/Implant versus Autologous Abdominal Tissue Breast Reconstruction in Postmastectomy Breast Cancer Patients: A Systematic Review and Meta-Analysis", Plastic and Reconstructive Surgery, Feb. 2014, 133(2):234-249.

Varma, et al., "Injectable Carboxymethylcellulose Hydrogels for Soft Tissue Filler Applications", Acta Biomaterialia, Aug. 2014, 10(12):4996-5004.

Visser, et al., "Reinforcement of hydrogels using three-dimensionally printed microfibres", Nature Communications, 2015, 6(6933):1-10.

Wan, "Microfluidic-Based Synthesis of Hydrogel Particles for Cell Microencapsulation and Cell-Based Drug Delivery", Polymers, Dec. 2012, 4(4):1084-1108.

Whitesides, et al., "Flexible Methods for Microfluidics", Physics Today, Jun. 2001, 54(6):42-48.

Whitesides, et al., "Soft Lithography", Angewandte Chemie International Edition, Mar. 16, 1998, 37(5):550-575.

Wu, et al., "Enhancing cell infiltration of electrospun fibrous scaffolds in tissue regeneration", Bioactive Materials, Sep. 2016, 1(1):56-64.

Wu, et al., "In vitro behaviors of hydroxyapatite reinforced polyvinyl alcohol hydrogel composite", Materials Chemistry and Physics, Feb. 15, 2008, 107(2-3):364-369.

Xu, et al., "Composites of electrospun-fibers and hydrogels: A potential solution to current challenges in biological and biomedical field", Journal of Biomedical Materials Research Part B, Apr. 2016, 104(3):640-656.

Xu, et al., "Material properties and osteogenic differentiation of marrow stromal cells on fiber-reinforced laminated hydrogel nanocomposites", Acta Biomaterialia, Jun. 2010, 6(6):1992-2002.

Yin, et al., "High density of immobilized galactose ligand enhances hepatocyte attachment and function", Journal of Biomedical Materials Research Part A, Dec. 2003, 67A(4):1093-1104.

Young, et al., "Injectable Hydrogel Scaffold from Decellularized Human Lipoaspirate", Acta Biomaterialia, Mar. 2011, 7(3):1040-1049.

Youngblood, et al., "It's All in the Delivery: Designing Hydrogels for Cell and Non-viral Gene Therapies", Molecular Therapy, Sep. 5, 2018, 26(9):2087-2106.

Extended European Search Report issued in European Application No. 15831684.4, dated Jan. 25, 2018, 7 pages.

Extended European Search Report issued in European Application No. 16837727.3, dated Mar. 25, 2019, 7 pages.

Extended European Search Report issued in European Application No. 16837731.5, dated Jun. 19, 2019, 15 pages.

International Search Report and Written Opinion of PCT Application No. PCT/US2015/045494, dated Nov. 6, 2015, 11 pages.

International Search Report and Written Opinion of PCT Application No. PCT/US2016/047282, dated Oct. 27, 2016, 11 pages.

International Search Report and Written Opinion of PCT Application No. PCT/US2016/047285, dated Dec. 20, 2016, 16 pages.

Japanese Office Action issued in Japanese Application No. 2017-528772, dated May 8, 2019, 6 pages of English Translation.

Notice of Allowance mailed in U.S. Appl. No. 15/432,606, filed Feb. 14, 2017, dated May 29, 2019, 9 pages.

Office Action issued in European Patent Application No. 15831684.4, dated Jan. 10, 2019, 5 pages.

Response of U.S. Non-Final Office Action issued in U.S. Appl. No. 15/432,606, filed Feb. 14, 2017, filed on Apr. 1, 2019, 9 pages.

U.S. Non-Final Office Action issued in U.S. Appl. No. 15/432,606, filed Feb. 14, 2017, dated Dec. 31, 2018, 21 pages.

Abedalwafa, et al., "Biodegradable Poly-Epsilon-Caprolactone (PCL) for Tissue Engineering Applications: A Review", Reviews on Advanced Materials Science, 2013, 34(2):123-140.

Alkhouli, et al., "The Mechanical Properties of Human Adipose Tissues and their Relationships to the Structure and Composition of the Extracellular Matrix", American Journal of Physiology, Endocrinology and Metabolism, Oct. 2013, 305(12):E1427-1435.

Annabi, et al., "Controlling the Porosity and Microarchitecture of Hydrogels for Tissue Engineering". Tissue Engineering Part B, Aug. 2010, 16(4):371-383.

Becker, et al., "Polymer Microfluidic Devices", Talanta, Feb. 2002, 56(2):267-287.

Beebe, et al., "Functional hydrogel structures for autonomous flow control inside microfluidic channels", Nature, 2000, 404(6778):588-559.

Bosworth, et al., "State of the art composites comprising electrospun fibres coupled with hydrogels: a review", Nanomedicine: Nanotechnology, Biology and Medicine, Apr. 2013, 9(3):322-335.

Brandt, et al., "Hyaluronic acid gel fillers in the management of facial aging", Clinical Interventions in Aging, 2008, 3(1):153-159.

Burdick, et al., "Hyaluronic Acid Hydrogels for Biomedical Applications", Advanced Healthcare Materials, Mar. 25, 2011, 23(12):H41-H56.

Butcher, et al., "Nanofibrous hydrogel composites as mechanically robust tissue engineering scaffolds", Trends in Biotechnology, Nov. 2014, 32(11):564-570.

Calobrace, et al., "The Biology and Evolution of Cohesive Gel and Shaped Implants", Plastic Reconstructive Surgery, Jul. 2014, 134(1S):6S-11S.

Chan, et al., "Functionalizable Hydrogel Microparticles of Tunable Size and Stiffness for Soft-Tissue Filler Applications", Acta biomaterialia, Feb. 2014, 10(6):2563-2573.

Cheng, et al., "An Update Review on Recent Skin Fillers", Plastic and Aesthetic Surgery, Mar. 2016, 3:92-99.

(56) References Cited

OTHER PUBLICATIONS

Chhaya, et al., "Chapter 10—Breast Reconstruction Using Biofabrication-Based Tissue Engineering Strategies", Biofabrication, Mar. 2013, pp. 183-216.
Choe, et al., "Hydrogel Biomaterials for Stem Cell Microencapsulation", Polymers (Basel), Sep. 2018, 10(9):997.
Choi, et al., "Pluronic/Chitosan Hydrogels Containing Epidermal Growth Factor with Wound-Adhesive and Photo-Crosslinkable Properties", Journal of Biomedical Materials Research Part A, Nov. 2010, 95A(2):564-573.
Christopherson, et al., "The influence of fiber diameter of electrospun substrates on neural stem cell differentiation and proliferation", Biomaterials, Feb. 2009, 30(4):556-564.
Chua, et al., "Stable immobilization of rat hepatocyte spheroids on galactosylated nanofiber scaffold", Biomaterials, May 2005, 26(15):2537-2547.
Chua, et al., "Surface-Aminated Electrospun Nanofibers Enhance Adhesion and Expansion of Human Umbilical cord Blood Hematopoietic Stem/Progenitor Cells", Biomaterials, Dec. 2006, 27(36):6043-6051.
Chun, et al., "Effect of Molecular Weight of Hyaluronic Acid (HA) on Viscoelasticity and Particle Texturing Feel of HA Dermal Biphasic Fillers", Biomaterials Research, Sep. 2016, 20(1):24.
Chung, et al., "Microfluidic Fabrication of Microengineered Hydrogels and their Application in Tissue Engineering", Lab Chip, Oct. 2011, 12(1):45-59.
Coburn, et al., "Biomimetics of the Extracellular Matrix: An Integrated Three-Dimensional Fiber-Hydrogel Composite for Cartilage Tissue Engineering", Smart Structures and Systems, Mar. 25, 2011, 7(3):213-222.
Daelemans, et al., "Nanostructured Hydrogels by Blend Electrospinning of Polycaprolactone/Gelatin Nanofibers", Nanomaterials, Jul. 2018, 8(7):551.
Dash, et al., "Stem Cells and Engineered Scaffolds for Regenerative Wound Healing", Bioengineering (Basel), Mar. 2018, 5(1):23.
Ekaputra, et al., "The Three-Dimensional Vascularization of Growth Factor-Releasing Hybrid Scaffold of Poly(Epsilon-Caprolactone)/Collagen Fibers and Hyaluronic Acid Hydrogel", Biomaterials, Nov. 2011, 32(32):8108-8117.
El-Sherbiny, et al., "Hydrogel scaffolds for tissue engineering: Progress and challenges", Global Cardiology Science and Practice, Nov. 2013, 2013(3):316-342.
Freeman, et al., "Evaluation of a Hydrogel-Fiber Composite for ACL Tissue Engineering", Journal of Biomechanics, Feb. 24, 2011, 44(4):694-699.
Gizaw, et al., "Electrospun Fibers as a Dressing Material for Drug and Biological Agent Delivery in Wound Healing Applications", Bioengineering, Jan. 2018, 5(1):1-28.
Gizaw, et al., "The Role of Electrospun Fiber Scaffolds in Stem Cell Therapy for Skin Tissue Regeneration", Med One, Feb. 2015, 4:1-40.
Goktas, et al., "Self-Assembled Peptide Amphiphile Nanofibers and PEG Composite Hydrogels as Tunable ECM Mimetic Microenvironment", Biomacromolecules, 2015, 16(4):1247-1258.
Han, et al., "Cell Attachment to Hydrogel-Electrospun Fiber Mat Composite Materials", Journal of Functional Biomaterials, Sep. 2012, 3(3):497-513.
Holloway, et al., "Interfacial optimization of fiber-reinforced hydrogel composites for soft fibrous tissue applications", Acta Biomaterialia, Aug. 2014, 10(8):3581-3589.
Jiang, et al., "The effect of nanofibre surface amine density and conjugate structure on the adhesion and proliferation of human haematopoietic progenitor cells", Interface Focus, Aug. 2011, 1(5):725-733.
Jordan, et al., "In Situ Fabrication of Fiber Reinforced Three-Dimensional Hydrogel Tissue Engineering Scaffolds", ACS Biomaterials Science and Engineering, Jun. 2017, 3(8):1869-1879.
Kai, et al., "Mechanical properties and in vitro behavior of nanofiber-hydrogel composites for tissue engineering applications", Nanotechnology, Mar. 9, 2012, 23(9):095705.
Kakagia, et al., "Autologous Fat Grafting: In Search of the Optimal Technique", Surgical Innovation, 2014, 21(3):327-336.
Katayama, et al., "Coil-reinforced hydrogel tubes promote nerve regeneration equivalent to that of nerve autografts", Biomaterials, Jan. 2006, 27(3):505-518.
Khetan, et al., "Degradation-mediated cellular traction directs stem cell fate in covalently crosslinked three-dimensional hydrogels", Nature Materials, May 2013, 12(5):458-465.
Kim, et al., "A Composite Dermal Filler Comprising Cross-Linked Hyaluronic Acid and Human Collagen for Tissue Reconstruction", Journal of Microbiology and Biotechnology, 2015, 25(3):399-406.
Kim, et al., "Biomimetic Scaffolds for Tissue Engineering", Advanced Functional Materials, 2012, 22(12):2446-2468.
Chinese OA issued in related CN Application No. 201980046070.1 on Aug. 25, 2022.
Japanese OA issued in JP Appl. No. 2021-156259 on Oct. 31, 2022.
Korean Office Action issued in KR 10-2017-7007215 dated Nov. 1, 2022.
Hyun Jong Lee et al., "Fabrication of Nanofiber Microarchitectures Localized within Hydrogel Microparticles and Their Application to Protein Delivery and Cell Encapsulation" (2013), Adv. Funct. Mater. vol. 23, pp. 591-597.
H. F. Zhu: "Catalyst Carriers", Chemical Industry, Press, p. 28-30 1980.
X,. Z. Ma, "Organic Chemistry", China Medical Science and Technology Press, p. 345 Jul. 31, 2014.
J. Zhang, et al. "Crosslinking of hyaluronic acid and human-like collagen with divinyl sulfone" Journal of Chemical and Pharmaceutical Research, 2014, 6(1):726-730.
Ibrahim, S., Q.K. Kang, and A. Ramamurthi, The impact of hyaluronic acid oligomer content on physical, mechanical, and biologic properties of divinyl sulfone?crosslinked hyaluronic acid hydrogels. Journal of Biomedical Materials Research Part A, 2010. 94(2): p. 355-370.
Russian Search Report issued in RU Application No. 2020140105 dated Dec. 13, 2022.
Israeli Office Action issued in 276313.4 dated Sept. 9, 2022.
Japanese Office Action dated Feb. 17, 2023 in JP 2020-563415.
Japanese Office Action dated Feb. 17, 2023 in JP 2020-563561.

* cited by examiner

NANOFIBER-HYDROGEL COMPOSITES FOR ENHANCED SOFT TISSUE REPLACEMENT AND REGENERATION

CROSS-REFERENCES TO RELATED APPLICATIONS

This application is a Continuation Application of PCT/US19/31638, filed on May 9, 2019 which claims the benefit of U.S. Provisional Application 62/669,307 filed May 9, 2018, which are incorporated by reference herein in their entirety.

GOVERNMENT SUPPORT

This invention was made with government support under grant no. 1R21NS085714 awarded by the U.S. National Institutes of Health and grant no. DMR1410240 awarded by the National Science Foundation. The government has certain rights in the invention.

SEQUENCE LISTING

The instant application contains a Sequence Listing which has been submitted electronically in ASCII format and is hereby incorporated by reference in its entirety. Said ASCII copy, created on Jul. 17, 2019, is named 048317-556001US_SL.txt and is 802 bytes in size.

BACKGROUND

Field

The present disclosure relates to composite materials and methods that restore lost soft tissue volume while promoting soft tissue regeneration. The present invention also relates to composite materials and methods for cosmetic, and reconstructive purposes.

Description of Related Art

Soft tissue defects resulting from trauma, oncologic resection, or congenital malformation are difficult to treat by conventional means. Current therapies, including tissue rearrangements or tissue transfer, cause donor site defects. Other therapies, such as prosthetic implants, lead to fibrosis and encapsulation. Existing strategies to promote tissue ingrowth are also inadequate for the treatment of soft tissue defects. Current acellular matrices result in flat, fibrotic sheets of tissue rather than the soft, three-dimensional tissue required for ideal reconstructions. Finally, while fat grafting can restore soft tissue defects, its wider use is hampered by variable graft survival and limited volumes of restoration. An ideal approach to soft tissue reconstruction would encourage regeneration of soft tissues such as adipose tissue in vivo followed by implantation of the tissues to promote regeneration. However, tissue regrowth requires a suitable matrix for cells to attach, migrate, proliferate, differentiation, and organize into new tissue. Much of the native extracellular matrix (ECM) is missing at the repair site. Therefore, recreating a synthetic matrix that not only immediately restores the lost tissue volume, but also reconditions the microenvironment, supports host cell infiltration, and encourages regeneration of soft tissue, becomes an essential task when repairing soft tissue defects using adipose tissue-based reconstruction.

Hydrogels have received significant interest as ECM mimics due to their high water content and water-swollen networks that allow for facile transport of water-soluble biomolecules. Therefore, hydrogels offer several advantages as a filler material for soft tissue reconstruction.

While several hydrogels have shown some benefits in soft tissue reconstruction, there is no current material that is able to address all of the mechanical challenges in succession.

To achieve sufficient mechanical property, higher cross-linking densities are usually required. Under these conditions, however, host tissue cells (e.g., adipocyte progenitors and endothelial progenitors) are not able to penetrate and grow into the scaffolds. In case of degradable hydrogels, scarring and fibrous tissue formation are typical because ingrowth of host tissue occurs too slowly, or at least at a pace slower than the absorption of the fiber material.

Recently, functionalized nanofibers have been developed to serve as ECM mimics to support various cell activities. FDA-compliant synthetic biodegradable poly-α-esters, such as polycaprolactone (PCL) or poly(lactide-co-glycolide) (PLGA) can be used to generate nanofibers through a process known as electrospinning. Biodegradable sutures and implants prepared from these polymers have been widely used clinically due to their excellent track record on biocompatibility. Various nanofibers of varying diameters and topographies for stem cell engineering applications have been developed. These nanofibers, however, do not offer macroscopic structures, making them difficult to use as 3D scaffolds.

Many commercialized hydrogel fillers cause moderate to severe inflammation in the patient, while not retaining full original volume over time.

Given the various problems associated with such conventional methods and systems, there is still a need in the art for improved solutions to healing soft tissue defects. The present disclosure provides a solution for this need that overcomes the various problems noted in the art.

SUMMARY

The compositions and methods in the following disclosure have been designed to addresses this need by using compositions comprising fiber-hydrogel composites such as fiber-hydrogel composite microbeads that possess improved properties (e.g., improved qualities for reconstruction of soft tissue, as detailed further infra).

Thus, in one aspect, disclosed herein is a population of substantially non-spherical microbeads comprising a functionalized hyaluronic acid network covalently linked to a plurality of polycaprolactone fibers having a mean length of less than about 200 micrometers, and a crosslinking agent present at a concentration from about 1 mg/mL to about 25 mg/mL, wherein the mean size of the microbeads is within the range of about 50 micrometers to about 300 micrometers along the longest dimension, wherein the microbeads are pre-reacted, wherein the microbeads are substantially stable at room temperature for at least about 6 months.

In another aspect, disclosed herein is a lyophilized formulation comprising a population of substantially non-spherical microbeads comprising a functionalized hyaluronic acid network covalently linked to a plurality of polycaprolactone fibers having a mean length of less than about 200 micrometers, and a crosslinking agent present at a concentration from about 1 mg/mL to about 25 mg/mL, wherein the microbeads are pre-reacted, wherein the microbeads comprise a moisture content of less than about 15%, wherein the microbeads are substantially stable at room temperature for at least about 12 months.

In one embodiment, the microbeads are substantially non-inflammatory.

In one embodiment, the functionalized hyaluronic acid comprises acrylated hyaluronic acid, and the crosslinking agent comprises thiolated poly(ethylene glycol), or a derivative thereof.

In another embodiment, the functionalized hyaluronic acid comprises thiolated hyaluronic acid, and the crosslinking agent comprises poly(ethylene glycol) diacrylate (PEGDA), or a derivative thereof.

In particular embodiments, the plurality of polycaprolactone fibers comprises an electrospun fiber.

In one embodiment, the diameter of the polycaprolactone fibers, is within the range of about 100 nanometers to about 5 micrometers.

In another embodiment, the microbeads has a mean storage modulus of between about 50 Pa and about 2500 Pa.

In one embodiment, the microbeads comprises plurality of pores. Optionally, the pores are disposed throughout the hyaluronic acid network such that it promotes tissue growth and cell infiltration when administered into a target tissue of a subject. In another embodiment, the plurality of pores comprises an area density of no less than about 50 pores per $cm^2$, with at least about 80% of pores having a mean size of no less than about 5 micrometers.

In one aspect provided here is an implantable or injectable biomaterial comprising the population of microbeads, wherein the biomaterial is formulated for dermal or subdermal administration into a target tissue of a subject.

In one aspect provided here is a formulation comprising the biomaterial, wherein the formulation is suitable for dermal injection via a needle no larger than 16-gauge, 18-gauge, 20-gauge, 22-gauge, 24-gauge, 26-gauge, 27-gauge, 28-gauge, 29-gauge, 30-gauge, 31-gauge, or smaller than 31-gauge.

A further aspect of the invention provides a kit comprising a syringe comprising from about 0.1 mL to about 20 mL of the microbeads, wherein said microbeads are formulated as i) substantially dehydrated beads or ii) hydrated beads that are ready for injection into a target tissue of a subject.

An additional aspect of the invention provides a formulation comprising the population of microbeads, wherein the microbeads are lyophilized to form dehydrated microbeads, and wherein the dehydrated microbeads are suitable for reconstitution with water, saline solution or suitable reconstitution fluid to substantially replace the water mass lost (as measured by weight) prior to administration into a target tissue of a subject such that when the water mass lost is replaced, the concentration of the microbeads in the reconstitution fluid is the same or substantially the same as the concentration of microbeads before lyophilization.

In one aspect provided here is the formulation, wherein the dehydrated microbeads retain or regain its beaded form upon reconstitution by water, saline solution or suitable reconstitution fluid prior to administrating into a target tissue of a subject in need thereof. In particular aspect provided here is the formulation, wherein the dehydrated microbeads are substantially stable at room temperature for at least about 12 months.

Another aspect of the invention provides a kit for preparation of the population of microbeads for immediate administration into a target tissue of a subject, the kit comprising: a vial containing the microbeads, said microbeads having been lyophilized and formed into powder cakes, wherein the lyophilized powder cakes are able to be reconstituted by water, saline solution or suitable reconstitution fluid.

A further aspect of the invention provides a kit for preparation of the population of microbeads for immediate injection into a target tissue of a subject, the kit comprising: (i) a syringe comprising the microbeads formulated as lyophilized gel beads; and (ii) a vial comprising water, saline solution or suitable reconstitution fluid, wherein water, saline solution or suitable reconstitution fluid is capable of being drawn up from the vial into the syringe, whereby the lyophilized microbeads are rehydrated.

A further aspect of the invention provides a kit for preparation of the population of microbeads for immediate injection into a target tissue of a subject, the kit comprising: (i) a syringe comprising the microbeads; and (ii) a vial comprising water, saline solution or suitable reconstitution fluid, wherein water, saline solution or suitable reconstitution fluid is capable of being drawn up from the vial into the syringe, whereby the lyophilized microbeads are rehydrated.

A further aspect of the invention provides the population of microbeads further comprising a compound selected from the group consisting of growth factors, compounds stimulating angiogenesis, immun A further aspect of the invention provides modulators, inhibitors of inflammation, and combinations thereof.

Another aspect of the invention provides the population of microbeads further comprising a compound that have therapeutic effects, vascularization effects, anti-vascularization effects, anti-inflammatory effects, anti-bacterial effects, anti-histamine effects, and combinations thereof.

In one embodiment, the population of microbeads further comprises a processed tissue extracellular matrix, wherein the processed tissue extracellular matrix is derivable from an adipose tissue.

A further aspect of the invention provides a method for performing a cosmetic procedure or a reconstructive procedure or reducing or reversing a tissue defect resulting from trauma, surgical intervention, or an age-associated disease, disorder or condition, comprising injecting into the tissue and/or the tissue defect a population of substantially non-spherical microbeads comprising a functionalized hyaluronic acid network covalently linked to a plurality of polycaprolactone fibers having a mean length of less than about 200 micrometers, and a crosslinking agent present at a concentration from about 1 mg/mL to about 25 mg/mL, wherein the mean size of the microbeads is within the range of about 50 micrometers to about 300 micrometers along the longest dimension, wherein the microbeads are pre-reacted, wherein the microbeads are substantially stable at room temperature for at least about 6 months.

Another aspect of the invention provides a population of substantially non-spherical microbeads comprising a functionalized hydrogel network covalently linked to a plurality of polymeric fibers having a mean length of less than about 200 micrometers, and a crosslinking agent present at a concentration from about 1 mg/mL to about 25 mg/mL, wherein the mean size of the microbeads is within the range of about 50 micrometers to about 300 micrometers along the longest dimension, wherein the microbeads are pre-reacted, wherein the microbeads are substantially stable at room temperature for at least about 6 months. In particular embodiments, the polymeric fiber, or fragments thereof, comprises a synthetic polymeric material comprising a poly (lactic-co-glycolic acid), poly(lactic acid), and/or a poly-caprolactone, or a combination or derivatives thereof; or a biological polymeric material selected from the group consisting of a silk, collagen, elastin, hyaluronic acid, chitosan, a derivative thereof, or a combination thereof. In another embodiment, the hydrogel material comprises a poly(ethylene glycol), a collagen, a dextran, an elastin, an alginate, a hyaluronic acid, a poly(vinyl alcohol), a derivative thereof, or a combination thereof.

Where applicable or not specifically disclaimed, any one of the embodiments described herein are contemplated to be able to combine with any other one or more embodiments, even though the embodiments are described under different aspects of the invention.

These and other embodiments are disclosed or are obvious from and encompassed by, the following Detailed Description.

BRIEF DESCRIPTION OF THE DRAWINGS

FIG. 1A depicts a comparison of the inflammatory response at post-injection day 1 for gels containing thiolated HA (HA-SH)+diacrylated polyethylene glycol (PEGDA) (crosslinking agent) (upward-pointing arrows) compared to gels containing acrylated HA (HA-Ac)+thiolated polyethylene glycol (PEGSH, downward-pointing arrow). FIG. 1B shows images from the inflammation study in a porcine inner thigh model at Day 0 (center panel) and Day 2 (right panel). The left panel shows the identity of the composite in each s.c. injection corresponding to the pattern shown on the inner thigh images. FIG. 1C shows the histological response to key groups in the porcine inner thigh model 48 hours after implantation. The blue staining indicates hyaluronic acid, and the red staining indicates immune cell staining. The injection site is encapsulated with a definitive boarder between host tissue and injection site in the thiolated-HA group, as visualized by the monocyte activation on the periphery of the injection site, which depicts a strong acute immune response to this HA group. FIG. 1D is a graph showing the shear storage modulus (in Pa) for the LS stiff and soft composites and relevant commercial controls.

FIG. 2A shows the composite after being particularized into 250-micron diameter beads; FIG. 2B shows the composite after being lyophilized and rehydrated, illustrating that the composite retains its original appearance; FIG. 2C is a 10× image depicting nanofiber and hydrogel components of the beaded formulation; and FIG. 2D is an optical microscopy image of the beaded formulation in a non-diluted state. FIG. 2E shows the non-effect of beading and lyophilization on the storage modulus. FIG. 2F is a schematic for generation of composite microbeads. FIG. 2G is a histogram of bead diameters (Mean=209.412±62.27 Median=210 n=51). Diameters of the beads were measured along the longest axis of the particles under a confocal microscope image. FIG. 2G is a microscopy image of beads with 75 um sieve (left), 150 μm sieve (middle), 250 μm sieve (right). FIG. 2H demonstrates beads of size ~75 μm, ~150 μm and ~200 μm by measuring the longest axis within the particle. Further characterized beads distribution was performed using image analysis program that will use edge detection for more consistent measurements. FIG. 2I is a injection force curve showing displacement under certain pressure to assess injectability of the composite depending on their bead size. The syringes filled with 150 μm and 75 μm beads were loaded into a syringe fixture (Instron) attached to a MTS Criterion 43 mechanical tester. The gel was injected out of the syringe through a 27 gauge needle (½" length, BD) at a crosshead speed of 1 mm/sec. The 150 μm and 75 μm groups both resulted in acceptable injection profiles. FIG. 2J shows the length distribution of the fibers dispersed throughout the hydrogel (Mean=110.36±85.4 μm, Range=12.00-442.00 μm, n=108). FIG. 2K shows the length distribution of the fibers from first Good Manufacturing Protocol (GMP) (Lot 0001-0025) nm dispersed throughout the hydrogel (Mean=30.10±26.87 Range=2.50-205.00 n=993).

FIG. 4A shows volume retention for the beaded composite compared to commercial controls as assessed by MRI quantification. FIG. 4B shows the effect of HA molecular weight (MW) on shear storage modulus of the composite prepared under the same HA concentration and fiber loading as used in 4A. FIG. 4C shows the effect of HA concentration (mg/ml) on shear storage modulus of the composite prepared under the same HA MW and fiber loading conditions; FIG. 4D shows the effect of HA concentration (mg/ml) on compression storage modulus of the composite prepared under the same HA MW and fiber loading conditions; FIG. 4E shows volume retention of scaffolds with variation in properties (see Table 1), demonstrating the tunability of the composite.

FIG. 5A shows 0% tissue ingrowth on Day 14, 30, and 50 post-injection with JUVÉDERM® filler, demonstrating the lack of host cell tissue ingrowth in this product. FIG. 5B shows tissue ingrowth after injection of the LS-9 formulation: 18% new tissue at Day 14, 52% new tissue at Day 30, and 84% new tissue at Day 50. FIG. 5C depicts the five parameters that were altered in order to determine which had the greatest effect on persistence of the composite in vivo: hydrogel molecular weight, hydrogel modification degree, hydrogel concentration, nanofiber concentration, and crosslinking density. As shown, linear predictive capability of the linear regression models is acceptable at 14 and 30 days (R2=0.95 and 0.86, respectively). The hydrogel concentration and the nanofiber concentration appeared to have the greatest effect.

FIG. 6A shows images of the pre-formed composite (lower left injection) in comparison with JUVÉDERM (lower right injection) at day 0 and day 2 with both image (top panels) and MRI cross section (bottom panels). FIG. 6B shows pairwise graphical comparison of the swelling effect on day 0 (left bars) and day 2 (right bars) of JUVÉDERM® VOLUMA XC® (left pair), ULTRA PLUS XC® (center pair) and LS beads (right pair). FIG. 6C is a graph showing that the LS-9 composite differentiates itself from market comparables by limiting post-procedural swelling and maximizing host tissue ingrowth.

FIG. 7C is three images showing a comparison of the composite (top left) with native human fat (bottom left). The two materials are shown side by side in the right panel.

FIGS. 8A-C show optical microscopy images of the LS beaded composite. HA-Ac, nanofibers, and 5k 2-arm PEGSH are formulated in PBS and reacted overnight. FIG. 8A is an image of the composite before the overnight reaction ("pre-beading"); FIG. 8B is an image of the composite after bead formation ("Beads"); FIG. 8C is an image of the composite after lyophilization and rehydration ("Post-lyophilization"). FIG. 8D is a graph showing measurement of shear storage modulus for each of 8A-8C, demonstrating the increased stability of the beaded composite compared to the bulk composite.

FIG. 10A shows the storage modulus for 250-micron bead samples including before beading, after beading, lyophilized in sugar solution, lyophilized in PBS. FIG. 10B shows shear elastic modulus after beading. FIG. 10C shows the tan delta after beading of 250-micron and 150-micron beads. FIG. 10D shows the trend in lower tan delta of commercial formulations, including the composite described herein.

FIG. 11A shows the general procedure for creating defects in the inguinal fat pad in a rabbit model. FIG. 11B shows host blood vessel infiltration into different graft matrices (150-Pa composite, 150-Pa hydrogel, and 80-Pa hydrogel) on POD 14. Endothelial cells were stained with CD31 in red and cell nuclei were stained with DAPI in blue. Fibers were F8BT-labelled in green. Scale bar: 100 μm.

DETAILED DESCRIPTION

Figure 1A:
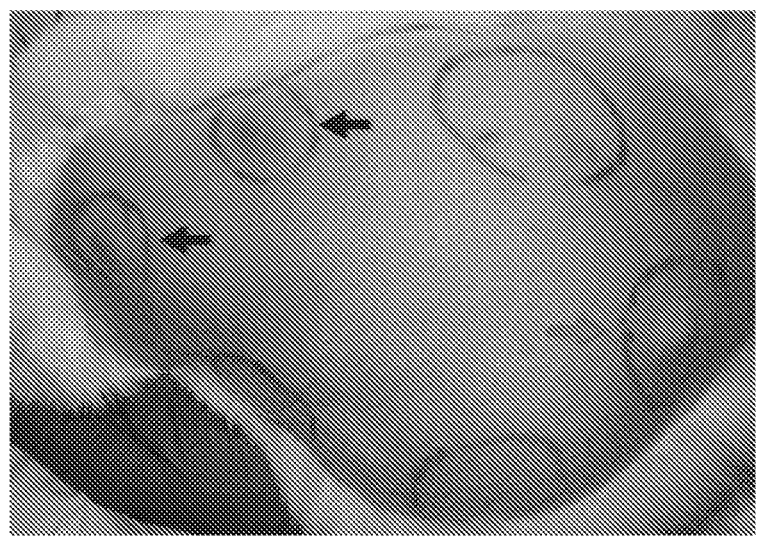
FIGS. 1A-1D are a set of images showing post-injection inflammatory responses.

The following detailed description, given by way of example, but not intended to limit the invention solely to the specific embodiments described, may best be understood in conjunction with the accompanying drawings.

The present invention relates to pre-reacted, beaded composite materials comprising a hydrogel and a nanostructure for use in methods for reconstruction of soft tissue.

The invention also relates to methods for repairing or reconstructing a soft tissue injury using a composition comprising a scaffold complex comprising a biomaterial covalently linked to a biodegradable fiber. The invention in other aspects also relates to a method of fabricating a composition for use in soft tissue reconstruction where the composition comprises a hydrogel and a nanostructure disposed therein.

The following is a detailed description of the invention provided to aid those skilled in the art in practicing the present invention. Those of ordinary skill in the art may make modifications and variations in the embodiments described herein without departing from the spirit or scope of the present invention. Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, figures and other references mentioned herein are expressly incorporated by reference in their entirety.

Although any methods and materials similar or equivalent to those described herein can also be used in the practice or testing of the present invention, the preferred methods and materials are now described. All publications mentioned herein are incorporated herein by reference to disclose and described the methods and/or materials in connection with which the publications are cited.

Unless defined otherwise, all technical and scientific terms used herein have the meaning commonly understood by a person skilled in the art to which this invention belongs. The following references, the entire disclosures of which are incorporated herein by reference, provide one of skill with a general definition of many of the terms (unless defined otherwise herein) used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, the Harper Collins Dictionary of Biology (1991). Generally, the procedures of molecular biology methods described or inherent herein and the like are common methods used in the art. Such standard techniques can be found in reference manuals such as for example Sambrook et al., (2000, Molecular Cloning—A Laboratory Manual, Third Edition, Cold Spring Harbor Laboratories); and Ausubel et al., (1994, Current Protocols in Molecular Biology, John Wiley & Sons, New-York).

The following terms may have meanings ascribed to them below, unless specified otherwise. However, it should be understood that other meanings that are known or understood by those having ordinary skill in the art are also possible, and within the scope of the present invention. All publications, patent applications, patents, and other references mentioned herein are incorporated by reference in their entirety. In the case of conflict, the present specification, including definitions, will control. In addition, the materials, methods, and examples are illustrative only and not intended to be limiting.

Definitions

The term "a" and "an" refers to one or to more than one (i.e., to at least one) of the grammatical object of the article. By way of example, "an element" means one element or more than one element.

As used herein, "about" can mean plus or minus less than 1 or 1, 2, 3, 4, 5, 6, 7, 8, 9, 10, 11, 12, 13, 14, 15, 16, 17, 18, 19, 20, 25, 30, or greater than 30 percent, depending upon the situation and known or knowable by one skilled in the art.

As used herein the specification, "subject" or "subjects" or "individuals" may include, but are not limited to, mammals such as humans or non-human mammals, e.g., domesticated, agricultural or wild, animals, as well as birds, and aquatic animals.

As used herein, the term "biologically active material" refers to any organic or inorganic agent that is biologically active, i.e. it induces a statistically significant biological response in a living tissue, organ or organism. The biologically active agent can be a medicine, peptide, polysaccharide or a polynucleotide, e.g. DNA and RNA.

It can be an agent for treatment of diseases in therapeutic areas like alimentary/metabolic, blood and clotting, cardiovascular, dermatological, genitourinary, hormonal, immunological, infection, cancer, musculoskeletal, neurological, parasitic, ophthalmic, respiratory and sensory. It can further be for treatment of diseases like osteoporosis, epilepsy, Parkinson's disease, pain and cognitive dysfunction. It can be an agent for the treatment of hormonal dysfunction diseases or hormonal treatment e.g. for contraception, hormonal replacement therapy or treatment with steroidal hormones. It can further be an agent such as an antibiotic or antiviral, anti-inflammatory, neuroprotective, prophylactic vaccine, memory enhancer, analgesic (or analgesic combination), immunosuppressant, antidiabetic or an antiviral. It can be an antiasthmatic, anticonvulsant, antidepressant, antidiabetic, or antineoplastic. It can be an antipsychotic, antispasmodic, anticholinergic, sympathomimetic, antiarrhythmic, antihypertensive, or diuretics. It can be an agent for pain relief or sedation. It can also be a tranquilliser or a drug for cognitive dysfunction. The agent can be in a free acid or base form, a salt or a neutral compound. It can be a peptide, e.g. levodopa; or an antibody fragment. It can be a polynucleotide, a soluble ion or a salt.

As used herein, a "scaffold complex" includes any covalent association of two components: a polymeric fiber and a hydrogel material. The scaffold complex contains the polymeric fiber and hydrogel material in a "functional network", meaning that the interactions between components results in a chemical, biochemical, biophysical, physical, or physiological benefit. In addition, a functional network may include additional components, including cells, biological materials (e.g., polypeptides, nucleic acids, lipids, carbohydrates), therapeutic compounds, synthetic molecules, and the like. In certain embodiments, the scaffold complex promotes tissue growth and cell infiltration when implanted into a target tissue present in a human subject.

As used herein, the term "hydrogel" is a type of "gel," and refers to a water-swellable polymeric matrix, consisting of a three-dimensional network of macromolecules (e.g., hydrophilic polymers, hydrophobic polymers, blends thereof) held together by covalent or non-covalent crosslinks that can absorb a substantial amount of water (e.g., 50%, 60% 70%, 80%, 90%, 95%, 96%, 97%, 98%, 99% or greater than 99% per unit of non-water molecule) to form an elastic gel. The polymeric matrix may be formed of any suitable synthetic or naturally occurring polymer material. As used herein, the term "gel" refers to a solid three-dimensional network that spans the volume of a liquid medium and ensnares it through surface tension effects. This internal network structure may result from physical bonds (physical gels) or chemical bonds (chemical gels), as well as crystallites or other junctions that remain intact within the extending fluid. Virtually any fluid can be used as an extender including water (hydrogels), oil, and air (aerogel). Both by weight and volume, gels are mostly fluid in composition and thus exhibit densities similar to those of their constituent liquids. A hydrogel is a type of gel that uses water as a liquid medium.

The definitions of "hydrophobic" and "hydrophilic" polymers are based on the amount of water vapor absorbed by polymers at 100% relative humidity. According to this classification, hydrophobic polymers absorb only up to 1% water at 100% relative humidity ("rh"), while moderately hydrophilic polymers absorb 1-10% water, hydrophilic polymers are capable of absorbing more than 10% of water, and hygroscopic polymers absorb more than 20% of water. A "water-swellable" polymer is one that absorbs an amount of water greater than at least 50% of its own weight, upon immersion in an aqueous medium.

The term "crosslinked" herein refers to a composition containing intramolecular and/or intermolecular crosslinks, whether arising through covalent or noncovalent bonding, and may be direct or include a cross-linker. "Noncovalent" bonding includes both hydrogen bonding and electrostatic (ionic) bonding.

The term "polymer" includes linear and branched polymer structures, and also encompasses crosslinked polymers as well as copolymers (which may or may not be crosslinked), thus including block copolymers, alternating copolymers, random copolymers, and the like. Those compounds referred to herein as "oligomers" are polymers having a molecular weight below about 1000 Da, preferably below about 800 Da. Polymers and oligomers may be naturally occurring or obtained from synthetic sources.

As used herein, the term "microbead" means a particle of the invention material of less than 300 μm in the longest dimension.

As used herein, the term "processed tissue extracellular matrix" means an extracellular matrix (ECM) taken from an animal subject, preferably human, and processed to disinfect and remove cells.

As used herein, the term "biomaterial" means an organic material that has been engineered to interact with biological systems. In some embodiments of the invention, a biomaterial is a hydrogel. In some embodiments, biomaterial is a bacterially derived hyaluronic acid.

As used herein, the term "biodegradable" refers to a material that can be broken down by biological means in a subject.

As used herein, the term "storage modulus" is used to define the measurement of the elastic components of the dynamic modulus which illustrates how the material responds to deformation or stress. In an embodiment, "deformation" means the change in shape or size of an object due to applied force.

As used herein, the term "shear modulus" also known as the modulus of rigidity, denoted by G, is defined as the ratio of shear stress to the shear strain. In an embodiment, "shear stress" means the component of stress coplanar with a material cross section. In an embodiment, "shear strain" means the force perpendicular to the material cross section.

As used herein, the term "implantable" means able to be formulated for implantation via a syringe to a subject.

As used herein, the term "soft tissue" refers to tissues that connect, support, or surround other structures and organs of the body. Soft tissue includes muscles, tendons, ligaments, fascia, nerves, fibrous tissues, fat, blood vessels, and synovial membranes.

As used herein, the term "stable" refers to a material that does not degrade at room temperature.

As used herein, the term "autologous" refers to any material derived from the same individual to whom it is later to be re-introduced into the individual.

As used herein, the term "allogeneic" or, alternatively, "allogenic," refers to any material derived from a different animal of the same species or different patient as the individual to whom the material is introduced.

As used herein, the term "lyophilized" refers to a material after undergoing a lyophilization, which is a process used for preserving materials by removing the water from the material, which involves first freezing the material and then drying it, under a vacuum, at very low temperatures.

As used herein, the term "functionalized" refers to a material that is uniformly or non-uniformly modified so as to have a functional chemical moiety associated therewith (e.g., chemically modified). In some cases, functional chemical moiety is capable of reacting to permit the formation of a covalent or non-covalent bond. In some cases, functional chemical moiety can provide the material improved properties.

Soft Tissue Reconstruction

Devastating soft tissue losses from tumor extirpation, trauma, aging, or congenital malformation affect millions of people each year. The loss of tissues including skin, fat, and muscle lead to major functional and aesthetic disturbances that are difficult to treat by conventional means. As an example, over 300,000 partial mastectomies are performed in the United States each year, leading to disfiguring breast scars from the loss of breast soft tissue. Existing options for soft tissue restoration have significant drawbacks. Autologous tissue flaps requires moving soft tissues from another part of the body in lengthy surgical procedures that leave donor-site deficits LoTempio 2010. *Plastic and Reconstructive Surgery*, 126(2), 393-401; Patel 2012. *Annals of Plastic Surgery*, 69(2), 139-144}. Prosthetic implants are prone to foreign-body response leading to fibrosis and encapsulation{Calobrace 2014 *Plastic and Reconstructive Surgery*, 134(1 Suppl), 6S-11; Tsoi 2014. *Plastic and Reconstructive Surgery*, 133(2), 234-249}. Fat grafting involving placement of adipocytes harvested during liposuction is limited to small volumes and is hampered by poor graft survival {Kakagia 2014 *Surgical Innovation*, 21(3), 327-336; Largo 2014 *British Journal of Plastic Surgery*, 67(4), 437-448}.

Finally, injectable hydrogel soft tissue fillers can be used, but these are suitable only for smaller defects. However, the volume restoration provided by existing fillers is transient {Young 2011. *Acta Biomaterialia*, 7(3), 1040-1049; Varma 2014 *Acta Biomaterialia*, 10(12), 4996-5004}. There exists a need in the art to provide long-lasting fillers that can provide a solution for age-related aesthetic defects. A new generation of tissue engineering solutions has been proposed to focus on using hydrogel scaffolds as templates to regenerate soft tissues such as adipose tissue at the site of reconstruction.

Current Tissue Engineering Approaches to Soft Tissue Reconstruction

Adipose-derived stem cells (ASCs) have been identified in wound beds surrounding soft tissue defects {Salibian 2013 *Archives of plastic surgery* 40.6: 666-675}. They can be differentiated into soft tissues such as fat, when supported with a suitable matrix microenvironment. Therefore strategies to fill the repair site with functional materials have the potential to enable the regeneration of new tissue using the endogenous ASCs or using ASCs and/or other mesenchymal cells present in liposuction aspirates that are readily obtainable using standard surgical practices. Hydrogels have been widely studied as a scaffold matrix for the regeneration of tissue defects due to their three-dimensional (3D) nature and elastic properties, which are similar to those of soft tissues. Various methods have been used to generate hydrogel scaffolds with moduli similar to that of native fat tissues (~2 kPa) {Alkhouli 2013 *American Journal of Physiology. Endocrinology and Metabolism*, 305(12), E1427-35; Sommer 2013 *Acta biomaterialia* 9.11 (2013): 9036-9048} while maintaining their volume and shape against physical stress from the surrounding tissue. This requires higher crosslinking density and smaller average pore size {Ryu 2011 *Biomacromolecules* 12.7 (2011): 2653-2659; Khetan 2013 *Nature Materials*, 12(5), 458-465; Li 2014 *Journal of Neurotrauma*, 31(16), 1431-1438}, leading to low cellular infiltration and poor regeneration. The ability for hydrogel scaffolds to promote cellular infiltration is the key to successful soft tissue restoration. Lack of vascular infiltration is responsible for the failure of large-volume fat grafting and other tissue engineering attempts. No currently available materials can fill the volume lost in soft tissue defects while promoting early vascularization and ASC differentiation to regenerate soft tissue.

Hydrogel Matrix

Various methods have been used to generate hydrogel fillers with shear storage moduli (G') similar to that of native fat tissues (150 to 500 Pa), so they may maintain their unique volume and shape against physical stress from the surrounding tissue. To date, these resilient structural properties have been achieved at the expense of high cross-linking density and small average pore size in the hydrogel networks, leading to limited cellular infiltration and consequently poor regeneration.

Porosity and pore size of the implant materials can influence host biological responses because of their effect on macrophage infiltration and activities. Several studies have shown that skewed polarization of macrophages triggered by pore features and mechanical property of the scaffold can influence the degree of fibrosis and scar formation (M1 macrophage-dominant response) versus angiogenesis and matrix remodeling (M2 macrophage-dominant response). Porous materials implanted in soft tissues, compared with nonporous implants, modulated pro-regenerative polarization of macrophages, promoted angiogenesis, and reduced fibrosis and scar formation. Therefore, the ability for hydrogel scaffolds to promote cellular infiltration and vascular ingrowth is key to modulating acute and chronic inflammation, promoting tissue remodeling, angiogenesis, and regeneration, and achieving a long-lasting soft tissue restoration.

Over the past few years, Li and Wen have developed a hyaluronic acid (HA) hydrogel conjugated with laminin-derived loop peptide (CCRRIKVAVWLC (SEQ ID NO: 1), 10 µM) with optimized pore size and modulus (10-100 Pa) for stem cell transplantation. They have shown that this hydrogel supports robust neural stem cell (NSC) migration and neurite sprouting from the differentiated cells {Li 2014 *Journal of Neurotrauma*, 31(16), 1431-1438}. In a rat controlled cortical injury (CCI) model for traumatic brain injury, this hydrogel, when injected on day 3 after the CCI injury, promoted significant vasculature network formation filling the lesion site (>10 mm) at 4 weeks to 6 months post implantation. This improved angiogenesis was attributed to the ability of this hydrogel to retain and present tissue-secreted growth factors, particularly vascular endothelial growth factor (VEGF). Literature reports also revealed that small HA degradation fragments of 3-10 disaccharide units were potent regulators of endothelial cell proliferation, migration, tubule formation, and angiogenesis {Slevin 2002 *Journal of Biological Chemistry*, 277(43), 41046-41059}. In a recent study, the effectiveness of this HA hydrogel to deliver human fetal tissue derived-NSC spheroids in a brain lesion site after CCI injury was tested. This HA hydrogel delivered robust vascular formation inside the scaffold matrix following transplantation. Regenerated blood vessels grew into the lesion and penetrated through the implanted matrix, and supported the survival and growth the neuronal progenitors. These results confirmed the unique ability of this optimized HA hydrogel composition in promoting host vascular ingrowth. More importantly, the hydrogel matrix is sufficiently porous to allow robust cell migration inside the hydrogel matrix. However, using this HA hydrogel directly for soft tissue reconstruction is not feasible, as its mechanical property is not sufficiently high to maintain the integrity of the implantation site—the surrounding adipose tissue has a modulus of more than 10-times higher. Increasing crosslinking density to improve its modulus will make it poorly permeable for cell infiltration and migration. A new strategy is needed to increase the mechanical property without significantly decreasing the average pore size of the bulk hydrogel. In an embodiment, the hydrogel of this invention is a substantially purified hyaluronic acid (HA), preferably produced by a bacterium.

Provided is a scaffold matrix that combines hydrogel materials or other biomaterials with polymeric fibers, formulated such that the density, ratio of gel to fibers, and other properties are variable, while maintaining sufficient porosity and strength. Provided is a scaffold matrix comprising materials that contain and/or are isolated from a processed tissue extracellular matrix, such as extracellular matrix derived and/or derivable from an adipose tissue.

In some embodiments, hydrogel materials are functionalized. In particular embodiments, hydrogel materials are functionalized with groups comprising hydroxyl, amino, carboxyl, thio, acrylate, sulfonate, phosphate, amide, as well as modified forms thereof, such as activated or protected forms. In preferred embodiments, hydrogel material comprises a hyaluronic acid (HA). In more preferred embodiments, hydrogel material comprises functionalized hyaluronic acid (HA). In other preferred embodiments, hydrogel material comprises acrylated hyaluronic acid (HA). In some embodiments, hydrogel material comprises thiolated hyaluronic acid (HA).

Scaffold Complexes

Provided herein are scaffold complexes suitable for use medical devices that are incorporated into a tissue of a human subject to whom the complexes are administered, e.g., by injection or implantation. The scaffold complexes contain a polymeric fiber, generally having a mean diameter of from about 10 nm to about 10,000 nm, such as about 100 nm to about 8000 nm, or about 150 nm to about 5,000 nm, or about 100, 150, 200, 250, 300, 350, 400, 450, 500, 600, 700, 800, 900, 1,000, 1,500, 2,000, 2,500, 3,000, 3,500, 4,000, 4,500, 5,000, 5,500, 6,000, 6,500, 7,000, 7,500, or 8,000. The polymeric fiber generally has a mean length of from about 10 µm to about 500 µm, such as about 10, 50, 100, 150, 200, 250, 300, 350, 400, 450, or 500 µm. In an embodiment, the length of the fibers is determined using optical fluorescence microscopy. In an embodiment, the length of the fibers is determined using electron microscopy.

In some embodiments, fibers are functionalized. In some embodiments, fibers are functionalized with groups comprising hydroxyl, amino, carboxyl, thio, acrylate, sulfonate, phosphate, maleimide, amide, as well as modified forms thereof, such as activated or protected forms.

As provided herein, the ratio of polymeric fiber to hydrogel material can be determined my any means known in the art. For example, the ratio of polymeric fiber to hydrogel material is from about 1:100 to about 100:1 on a component-mass basis, such as about 1:50 to about 50:1, or 1:10 to about 10:1, such as 1:5 to about 5:1, such as about 1:3 to about 3:1. The ratio of polymeric fiber to hydrogel material is also provided as a concentration basis, e.g., a given weight of polymeric fiber per volume of hydrogel material. For example, the concentration is from about 1 to 50 mg/mL. The hydrogel material is generally disposed on the polymer fiber, such as being bonded to the outer surface (or an outer surface, depending upon the composition and shape) of the polymer fiber. The scaffold complex is not generally a uniform solid material. Instead, scaffold complexes contain a plurality of pores present on or within a surface of the scaffold complex. The presence, size, distribution, frequency and other parameters of the pores can be modulated during the creation of the scaffold complex. Pore size can be from below about 1 µm to up to 100 µms, including 1, 2, 3, 4 5, 10, 15, 20, 30, 40, 50, 60 70, 80, 90 or 100 µms, and the size thereof may be narrowly tailored, e.g., such that at least 40%, such as 50%, 60%, 70%, 80%, 90%, 95% or greater than 95% of the pores are in a desired size or within a desired size range.

The scaffold complexes of the invention are suitable for incorporation into a tissue of a human subject, and thus they are generally "biocompatible", meaning capable of interacting with a biological system (such as found in a human subject) without inducing a pathophysiological response therein and/or thereby. In some embodiments the scaffold complex is provided in order to be durably retained in the tissue. Alternatively, the scaffold complexes are transiently retained in the human subject and are provided as substantially biodegradable. Preferably, a polymeric fiber contains a biocompatible biodegradable polyester. In a preferred embodiment, the polymeric fiber contains polycaprolactone.

As provided herein, one preferred form of interaction of the complex containing polymer fiber and hydrogel includes a crosslinking moiety, generally present in an amount effective to introduce bonding between polymer fiber and hydrogel material, e.g., to induce crosslinking between polycaprolactone fiber and hyaluronic acid.

Scaffold Design for Soft Tissue Restoration

The composite concept has been widely used as a material-reinforcement mechanism. For example, adding hydroxyapatite particles into hydrogel can increase its stiffness {Wu 2008 *Materials Chemistry and Physics* 107.2 (2008): 364-369}, and the composite tensile modulus increases even more for elongated particles {Yusong 2007 *Journal of Materials Science*, 42(13), 5129-5134}. Electrospun nanofiber meshes have been used widely as a tissue engineering substrate due to their topographical similarity to the native ECM. Of particular interest, the decellularized ECM of adipose tissue is highly fibrous and porous in nature (FIG. 6G) {Young 2011. *Acta Biomaterialia*, 7(3), 1040-1049}. Several recent studies have attempted to recapitulate the fibrous components by introducing fragmented poly (lactide) (PLA) or chitosan fibers to a polyethylene glycol (PEG), polyacrylamide, or alginate hydrogel {Coburn 2011 *Smart Structures and Systems*, 7(3), 213; #37; Zhou 2011 *Colloids and Surfaces B: Biointerfaces*, 84(1), 155-162; Shin 2015 *Journal of Materials Chemistry*}. The fragmented fibers are mixed with hydrogel precursor solutions and incorporated into hydrogel during the gelation process to create a 3D architecture. These fiber-embedded hydrogels have shown improved mechanical properties over the corresponding hydrogels. However, there has been no report on testing host cell infiltration in vivo. In addition, these hydrogels are non-degradable and require adhesive ligands for adipocyte adhesion and differentiation.

Nanofiber-Biomaterial Composite Design

To achieve fiber-reinforcement effect while maintaining high porosity in the hydrogel phase, an electrospun fiber-hydrogel composite that offers superior properties as compared to other scaffolds is provided. Beyond blending nanofibers and a hydrogel matrix, which has been reported previously {Coburn 2011 *Smart Structures and Systems*, 7(3), 213}, introduced here are interfacial bonding between fiber surfaces and the hydrogel crosslinking network (FIG. 6). Such a composite design not only allows stronger mechanical reinforcement from the solid fiber component, but also allows independent tuning of bulk mechanical properties and the average pore size/porosity of the hydrogel phase, enabling both optimal cell infiltration properties and structural integrity. It is further contemplated that fibers can be employed as preferred cell adhesion substrates for ASCs and endothelial progenitors, therefore acting as a guide to support cell migration and ASC differentiation.

To further achieve the desired effects, the invention includes a PEG crosslinking agent to introduce crosslinking between the nanofibers and also between the nanofibers and the hydrogel. This helps to extend durability of the product, and allows for modulation of crosslinking density in order to achieve optimal other properties.

Non-Spherical Beaded Formulation

In other dermal filler compositions known in the art, the composites/hydrogels are formed into particulate formulations, enabling use of higher concentrations of each component and enhanced stability. For example, some commercial hydrogel-based fillers us a blending method in order to form these beads. This method is not ideal because it allows for little control over bead size and shape.

Figure 3:
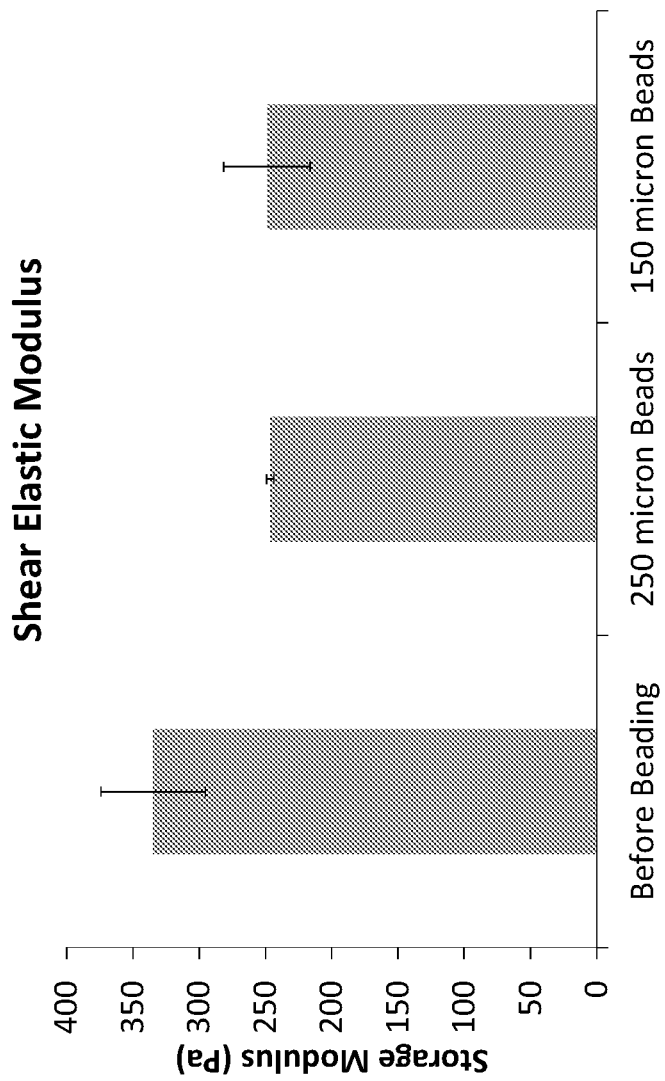
FIG. 3 shows the storage modulus for the bulk composite gel compared to beaded particles at 150 and 250 μm.

In versions of the invention, the nanoparticle-hydrogel scaffold matrix is formed as a bulk composite gel. Provided are improvements including introducing the composite as a beaded gel. This allows for the user to vary the bead properties in order to get desirable results (Table 1, FIGS. 4B, 4C, and 4D) and improves the storage modulus of the composite (FIG. 3). The current invention introduces a system of particulation wherein the pre-formed hydrogel-nanofiber composite is physically modulated, such as by being pushed through one, two, three, or more than three mesh screens, creating a population of nonspherical beads that are relatively similar to one another in shape and size. This two-screen system allows for tight control over the size of the beads, thus allowing the user to modulate the size as needed (Table 1).

tions of human factors, e.g. the user preparation and handling that this necessitated. Varying mixing and wait times can change the reaction time and thus significantly alter the stiffness of the complex. This could cause the gel to be too stiff to be injected through a syringe, or not stiff enough, which would create undesirable properties when injected into a subject. To address this problem, the inventors developed a pre-reacted composition, wherein the reaction (e.g gelation) takes place prior to storage.

The formulation, comprising 7 mg/mL HA-Ac, 8 to 10 mg/mL of fibers with maleimide, and 6.9 m/mL of PEGSH, is fully reacted in bulk at 37° C. By pre-reacting the gel during manufacturing, the inventors removed the need to protect the labile functional groups and removed the need for extensive mixing and curing by the end-user.

Lyophilization

The present invention includes a step of lyophilization prior to storage of the complex. The introduction of lyophilization allows for storage of the product at room temperature for extended periods of time without loss of function. In an embodiment, the beaded product is lyophilized in an isotonic solution of sucrose, Trehalose, and sodium chloride. These variables protect the microstructure during the drying process and extend the product's shelf life. In an embodiment, the lyophilized gel beads are reconstituted with water after storage, allowing them to be ready for injection within seconds.

The mechanical properties of the nanofiber phase of the fiber-hydrogel composite do not substantially change in the dried or frozen state, as opposed to most hydrogel components. Thus, during freezing or lyophilization, the fiber fraction can help maintain the overall composite microstructure. With the correct lyophilization cycle and formulation,

TABLE 1

The pre-formed composite were mixed with high and low crosslinking densities (stiffness), combining the advantages of both particle types (stiffer, slower degrading, and longer lasting; vs. more porous, better cell infiltration, and vascularization). The ratio of the two types of composite particles can be tuned to combine various desirable qualities of the invention. Fourteen of the formulation were made based on these optimization parameters and are being tested.

| # | HA-Ac MW (MDa) | Acrylation (%) | HA-Ac (mg/mL) | PCL Fibers (mg/mL) | PEGSH (mg/mL) | Storage Mod (Pa) |
|---|---|---|---|---|---|---|
| LS-1 | 0.7 | 10.0 | 7.0 | 10.0 | 7.2 | 121 |
| LS-2 | 0.7 | 19.0 | 7.0 | 10.0 | 7.7 | 222 |
| LS-3 | 1.5 | 23.0 | 7.0 | 10.0 | 11.7 | 191 |
| LS-4 | 1.5 | 23.0 | 15.0 | 10.0 | 24.0 | 627 |
| LS-5 | 1.5 | 23.0 | 15.0 | 30.0 | 25.7 | 2190 |
| LS-6 | 1.5 | 23.0 | 20.0 | 20.0 | 32.5 | 1259 |
| LS-7 | 2.7 | 15.3 | 7.0 | 10.0 | 6.0 | 186 |
| LS-8 | 2.7 | 15.3 | 7.0 | 20.0 | 8.9 | 281 |
| LS-9 | 2.7 | 15.3 | 7.0 | 30.0 | 12.3 | 386 |
| LS-10 | 2.7 | 15.3 | 15.0 | 30.0 | 18.0 | 1277 |
| LS-11 | 1.3 | 20.4 | 13.4 | 26.0 | 22.0 | 1273 |
| LS-12 | 1.3 | 20.4 | 17.4 | 18.0 | 27.4 | 984 |
| LS-13 | 1.5 | 23.0 | 10.0 | 20.0 | 16.0 | 546 |
| LS-14 | 1.5 | 23.0 | 10.0 | 30.0 | 15.0 | 340.68 |
| Voluma XC | 2.5 | #N/A | 24.0 | #N/A | #N/A | 265 |
| Prevelle | #N/A | #N/A | 7.0 | #N/A | #N/A | 195 |

Pre-Reacted Composite

As noted herein, the invention described comprises a complex that is reacted prior to injection or prior to storage. In previous embodiments of the invention, the components of the formulation were mixed by the end-user immediately prior to injection into a subject. This introduced complicathe composite can be lyophilized, while still remaining as distinct beads upon rehydration.

Innovation

In certain aspects, an innovation is the pre-reacted, beaded nanofiber-hydrogel composite design with crosslinking and interfacial bonding between nanofiber surfaces and the hydrogel network, that is able to be lyophilized and maintain its composition post-rehydrating. This engineered composite has the potential to drastically improve the mechanical property of the hydrogel without significantly decreasing the average pore size in the hydrogel phase. The introduction of interfacial bonding can offer superior mechanical strengthening effect comparing to just physical blending of the two components. This study will map out the range of mechanical properties (density, porosity, and shear moduli) attainable with electrospun polycaprolactone (PCL) fiber-HA hydrogel composites in contrast to blends.

Figure 1B:
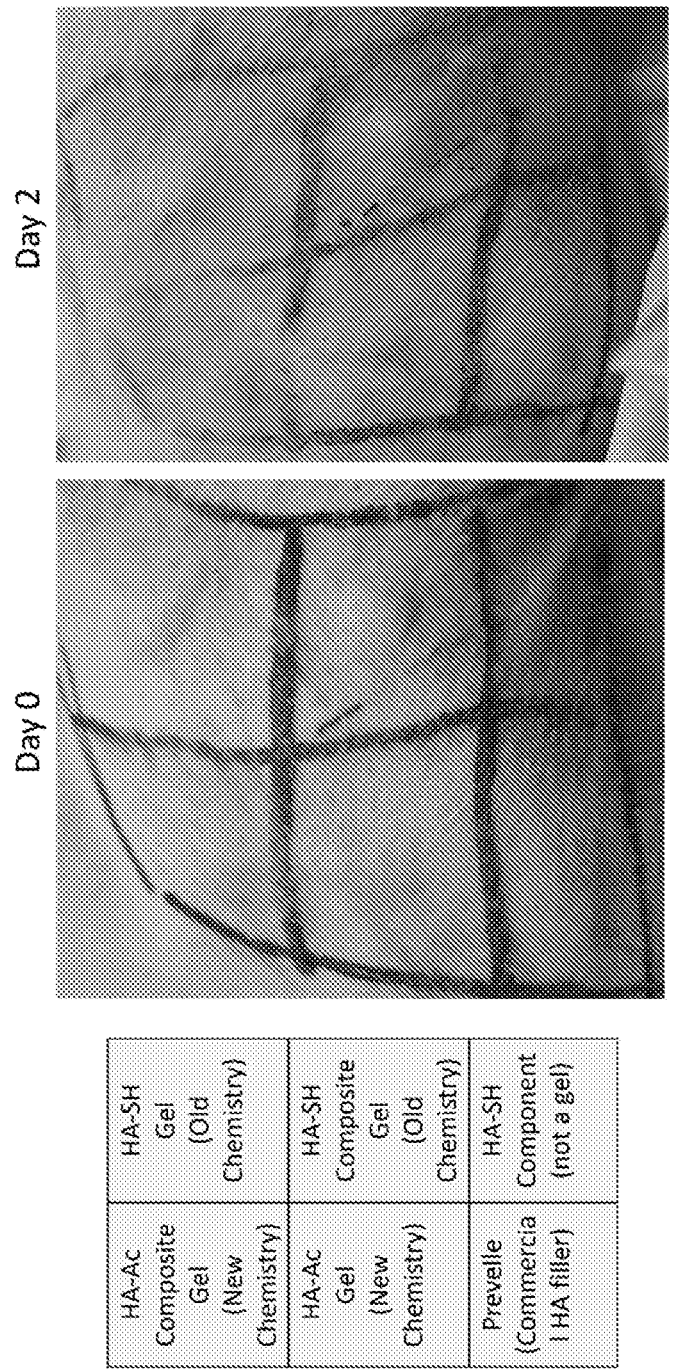
Figure 1C:
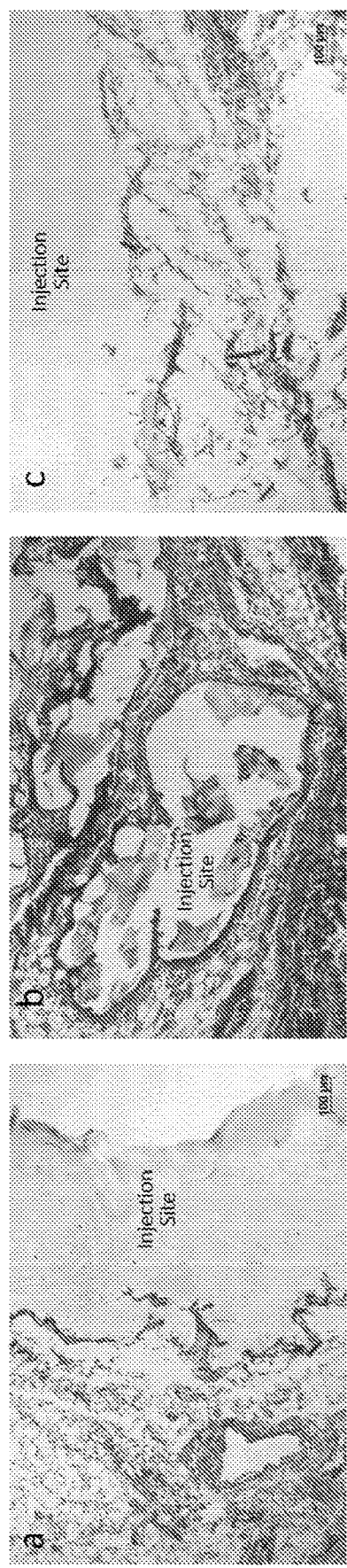

A key innovation is the reduction in inflammation achieved by optimizing the chemistry in the in-situ forming of this composite material. The inventors have improved the invention in comparison to previous work by identifying the chemical properties that cause inflammation in a subject, and creating compositions with new properties that reduced this problem. Previous embodiments of this invention used thiolated-HA (HA-SH) and an acrylated PEG crosslinker (PEGDA). This had a negative response in subjects, including acute immune response as shown in FIG. 1C, and inflammation after injection (FIGS. 1A and 1B). Using an alternative composition comprising acrylated HA (HA-Ac) and thiolated PEG crosslinking agent (PEGSH). This reduction of reactive groups offered a solution to the inflammation problem. FIGS. 1A and 1B demonstrate this improvement in comparison to previous embodiments of the invention and in comparison to other commercially available fillers.

Another innovation is the demonstration of such a nanofiber-hydrogel composite to restore soft tissue defects. Preliminary characterization demonstrated that the composite shared structural characteristics with adipose tissue (FIG. 6) {Christman, 2012 US 20120264190 A1; Young 2011. *Acta Biomaterialia*, 7(3), 1040-1049}. It was hypothesized that this composite offers structural integrity and mechanical properties important for soft tissue regeneration. This study has also demonstrated the versatility and efficiency of composites, as compared to hydrogels.

In other aspects, a key innovation is the incorporation of cell-binding or tissue-binding moieties into the nanofiber-hydrogel composite material. These moieties including peptides, aptamers, antibodies, small molecules, or other binding reagents confer enhanced ability of the composite to incorporate cells from the local wound environment or exogenously provided cells. The resultant integral structure of bound nanofibers, hydrogel, and cells behaves more like native tissue than the nanofiber-hydrogel composite alone. The incorporated cellular elements including adipocytes, endothelial cells, pericytes, and other mesenchymal cells can better interface with and remodel the nanofiber-hydrogel composite as well as surrounding tissues to effect a more natural and durable repair.

In other aspects, a key innovation is the association of cells to the nanofiber-hydrogel composite material. The associated cellular elements including adipocytes, endothelial cells, pericytes, and other mesenchymal cells can better interface with and remodel the nanofiber-hydrogel composite as well as surrounding tissues to effect a more natural and durable repair while providing a suitable mechanical strength to mimic ECM.

In other aspects, a key innovation is the association of tissue to the nanofiber-hydrogel composite material. The associated tissue such as adipose tissue can better interface with and remodel the nanofiber-hydrogel composite as well as surrounding tissues to effect a more natural and durable repair while providing a suitable mechanical strength to mimic ECM.

A key innovation of the current invention is the stability of the complex at room temperature (between 15° C. (59° F.) and 18° C. (64° F.)). A problem faced by many commercially available hydrogel- or hyaluronic acid-based fillers is the necessity to be stored in cool conditions. This limits the amount of time they can be stored, thus shortening the window in which the end-user can administer the product to a subject. An objective of the invention herein is improved storage stability. The creation of a pre-reacted, beaded formulation that can be lyophilized and rehydrated for administration addresses this unmet need.

The successful completion of this project will deliver an off-the-shelf solution for the restoration of missing soft tissue volume, particularly for larger defects where establishing vascular network, maintaining tissue repair site integrity, promoting cell migration and organization, and recruiting host cells are all crucial to a sustainable tissue restoration. The extensive clinical track record for the materials components used in this composite design, i.e. HA hydrogel and biodegradable polyester fibers, together with these preliminary data on tissue compatibility, suggested superior tissue compatibility and a straightforward regulatory approval path for clinical translation.

Features:

In some embodiments, the invention provides the crosslinking and interfacial bonding between nanofibers and polymer network in the hydrogel component. This is important for the formation of a "true" composite. It was demonstrated that blending such fibers and hydrogel did not provide the same degree of mechanical enhancement. There are also previous reports on the use of nanofiber-hydrogel blends. In other words, the crosslinking and interfacial bonding importantly differentiates this new work from the art. Furthermore, the interfacial bonding could include covalent bonds as shown in this manuscript, and secondary bonding, such as hydrogen bonds and electrostatic charge interaction.

In some embodiments, the invention provides mesenchymal cell binding elements in the nanofiber-hydrogel composites that can enhance the ability of the resultant composite to recruit, capture, and/or embed mesenchymal cells. The resultant material consisting of both cells and nanofiber-hydrogel composite can behave more like native tissue and can effect more natural and durable repair than the nanofiber-hydrogel composite alone.

In some embodiments, the invention provides mesenchymal cells incorporated into the composite structure. Optionally, these cells can be obtained from liposuction aspirates in routine clinical practice by those skilled in the art. Such cells including adipocytes, mesenchymal stem cells, endothelial precursors, adipocyte precursors, endothelial cells, and pericytes can be incorporated into the nanofiber-hydrogel composite to generate novel materials that resemble native soft tissue.

This is also the first work in the field that demonstrates isotropic reinforcement—the composite is stronger in all orientations, as needed to replace volumetric defects of arbitrary geometry. Designs with nanofiber mats or a small number of aligned filaments are inherently anisotropic. This design is capable of forming both isotropic and anisotropic materials.

In this invention, the chemical composition of each component has been altered in order to reduce inflammation in a patient, while maintaining other important physical properties of the scaffold, such as strength and storage modulus. [[Specifics on this should be disclosed in an Example.

Especially important: the position of the thiol group in this formulation (section A2 in invention disclosure) had big effect on sensitivity.]]

The work presented herein defines a scaffold complex that is formulated into non-spherical microbeads. This beading improves the storage stability of the gel and allows for variation of other properties that can improve the function of the complex and differentiate the qualities for different purposes.

Figure 12:
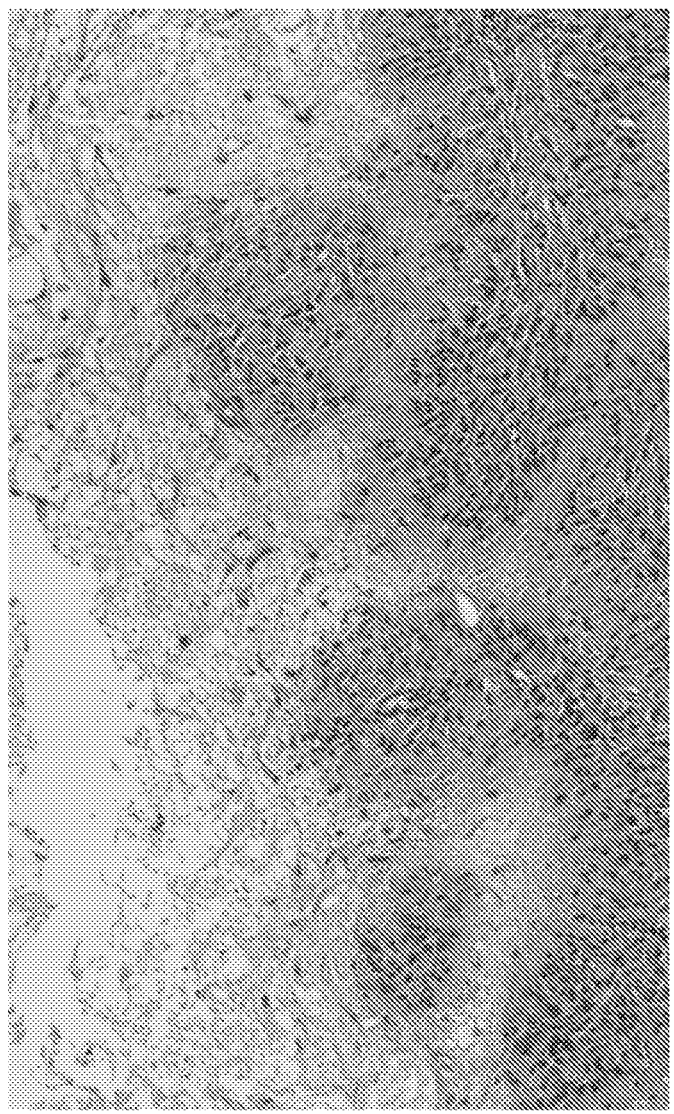
FIG. 12 shows the histological analysis (H & E-stained) in rat model at POD 13 weeks after injection of LS-5. It is clearly observed that the growth/infiltration pattern of the cells, which recapitulate the underlying bead morphology.

The work presented herein defines a scaffold complex that is reacted prior to injection, in order to reduce the possibility of end-user error. In situ forming of the composite introduces the complication of human factors, including the user preparation and handling that it necessitates. Mixing and wait times on the order of minute affect properties of the formulation, such as undesirable stiffness and elasticity (FIGS. 12A and 12B).

The invention herein introduces the step of lyophilizing the beaded scaffold complex, allowing it to be stable when stored at room temperature (FIG. 11). The beads can be rehydrated prior to use within seconds, while maintaining their original properties. Existing HA fillers can't be irradiated for sterilization because the aqueous environment enables too much HA chain scission. Lyophilizing the product prior to storage not only allows for the composition to be stored for longer periods of time, but also enables additional terminal sterilization modalities, i.e. irradiation via gamma or e-beam.

The work presented herein, for at least certain aspects, defines the components used for the formation of composite to be a hydrogel network with sufficient pore size and porosity (around the beads and within the beads) for cell migration and host tissue ingrowth, and nanofibers which loosely include polymer fibers with diameters ranging from 50 nm to 10 μm.

Gel/Hydrogel Component

In an embodiment, the scaffold complex of the invention is a composite comprising a hydrogel. The hydrogel can include any type of suitable hydrogel component. The invention contemplates nanostructure/gel composites that include any suitable gel component, including any suitable hydrogel component known in the art. The gel and/or hydrogels can be formed of any suitable synthetic or naturally-occurring materials.

For example, the polymer component of the gels and/or hydrogels can comprise a cellulose ester, for example, cellulose acetate, cellulose acetate propionate (CAP), cellulose acetate butyrate (CAB), cellulose propionate (CP), cellulose butyrate (CB), cellulose propionate butyrate (CPB), cellulose diacetate (CDA), cellulose triacetate (CTA), or the like. These cellulose esters are described in U.S. Pat. Nos. 1,698,049, 1,683,347, 1,880,808, 1,880,560, 1,984,147, 2,129,052, and 3,617,201, and may be prepared using techniques known in the art or obtained commercially. Commercially available cellulose esters suitable herein include CA 320, CA 398, CAB 381, CAB 551, CAB 553, CAP 482, CAP 504, all available from Eastman Chemical Company, Kingsport, Tenn. Such cellulose esters typically have a number average molecular weight of between about 10,000 and about 75,000.

The cellulose esters and comprise a mixture of cellulose and cellulose ester monomer units; for example, commercially available cellulose acetate butyrate contains cellulose acetate monomer units as well as cellulose butyrate monomer units and unesterified cellulose units.

The gels/hydrogels of the invention may also be comprised of other water-swellable polymers, such as acrylate polymers, which are generally formed from acrylic acid, methacrylic acid, methyl acrylate, ethyl acrylate, methyl methacrylate, ethyl methacrylate, and/or other vinyl monomers. Suitable acrylate polymers are those copolymers available under the tradename "EUDRAGIT®" from Rohm Pharma (Germany), as indicated, supra. The Eudragit series E, L, S, RL, RS and NE copolymers are available as solubilized in organic solvent, in an aqueous dispersion, or as a dry powder. Preferred acrylate polymers are copolymers of methacrylic acid and methyl methacrylate, such as the Eudragit L and Eudragit S series polymers. Particularly preferred such copolymers are Eudragit L-30D-55 and Eudragit L-100-55 (the latter copolymer is a spray-dried form of Eudragit L-30D-55 that can be reconstituted with water). The molecular weight of the Eudragit L-30D-55 and Eudragit L-100-55 copolymer is approximately 135,000 Da, with a ratio of free carboxyl groups to ester groups of approximately 1:1. The copolymer is generally insoluble in aqueous fluids having a pH below 5.5. Another particularly suitable methacrylic acid-methyl methacrylate copolymer is Eudragit S-100, which differs from Eudragit L-30D-55 in that the ratio of free carboxyl groups to ester groups is approximately 1:2. Eudragit S-100 is insoluble at pH below 5.5, but unlike Eudragit L-30D-55, is poorly soluble in aqueous fluids having a pH in the range of 5.5 to 7.0. This copolymer is soluble at pH 7.0 and above. Eudragit L-100 may also be used, which has a pH-dependent solubility profile between that of Eudragit L-30D-55 and Eudragit S-100, insofar as it is insoluble at a pH below 6.0. It will be appreciated by those skilled in the art that Eudragit L-30D-55, L-100-55, L-100, and S-100 can be replaced with other acceptable polymers having similar pH-dependent solubility characteristics.

Hyaluronic Acid (HA).

In various other embodiments, the composite materials of the invention can be based on hyaluronic acid (HA) as the hydrogel material. HA is a non-sulfated, linear polysaccharide with repeating disaccharide units which form the hydrogel component. HA is also a non-immunogenic, native component of the extracellular matrix in human tissues, and widely used as a dermal filler in aesthetic and reconstructive procedures.

In some embodiments, hyaluronic acid are functionalized. In particular embodiments, hyaluronic acid are functionalized with groups comprising hydroxyl, amino, carboxyl, thio, acrylate, sulfonate, phosphate, amide, as well as modified forms thereof, such as activated or protected forms.

Breakdown of HA is facilitated by native hyaluronidases whose expression is increased in areas of tissue damage and inflammation. Importantly, studies have shown that small HA degradation fragments of 3-10 disaccharide units are potent regulators of endothelial cell proliferation, migration, tubule formation, and angiogenesis. These biological functions of HA are thought to be mediated via CD44 in a pathway involving Ras and PKC. Blockade of CD44/HA interactions using anti-CD44 antibodies reduced proliferation and migration of human microvascular endothelial cells in vitro. HA hydrogels have been investigated as potential matrices for cell delivery in a variety of models of cell and tissue injury. These hydrogels can serve as a protective and supporting scaffold for cells and can also reduce scarring. Thus, it is believed HA has a critical role in enhancing tissue regeneration by promoting cell infiltration and promoting angiogenesis.

First, the material has three-dimensional integrity and a consistency similar to that of native fat tissue. This renders it suitable for off-the-shelf restoration of missing soft tissue volume. Second, the material preferably may be deposited with a plurality of flexible nanofibers that can serve as substrates for migration of adipocytes and endothelial progenitors. Third, the material has sufficient porosity to allow these precursor cells to rapidly infiltrate and integrate into the scaffold rather than forming a fibrous capsule around it. Fourth, the HA hydrogel component provides compressibility and volumetric expansion while also providing important angiogenic cues. Fifth, the nanofiber and hydrogel components are biodegradable allowing them to be replaced by regenerated soft tissue. Sixth, all component materials have strong safety track records in numerous FDA-approved devices, potentially reducing regulatory hurdles for clinical translation.

Figure 4A:
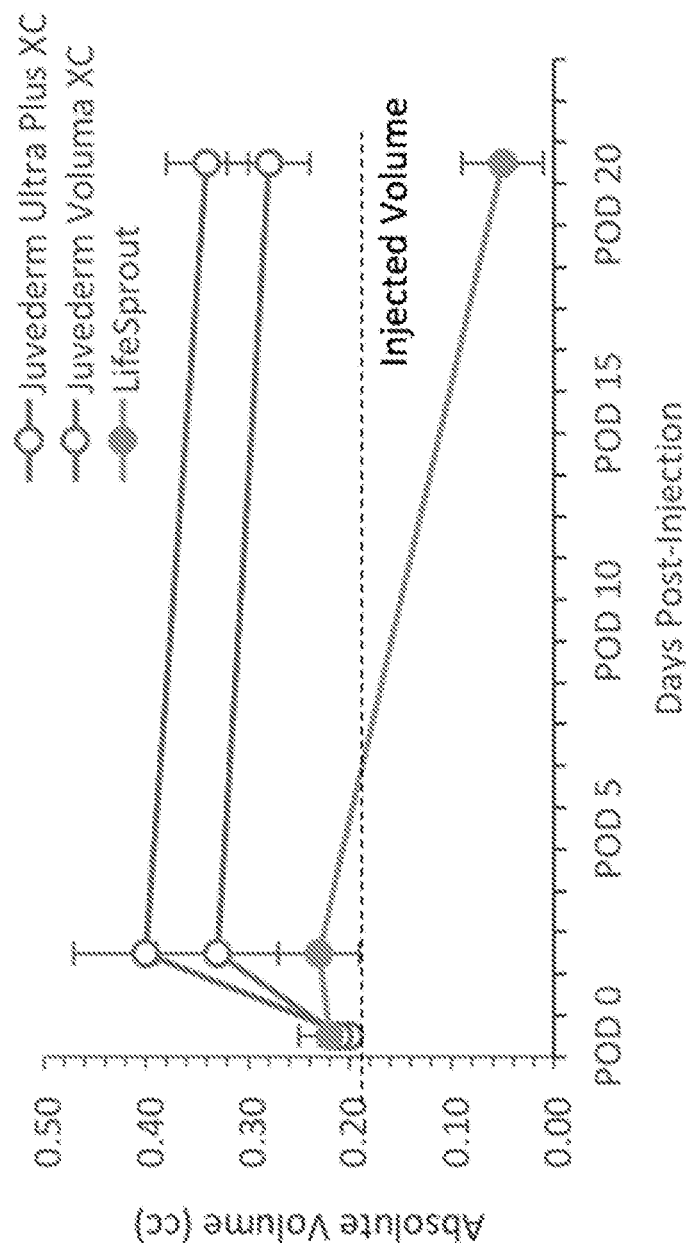
FIGS. 4A-4E are two graphs showing analysis of the composite LS-1.
Figure 4B:
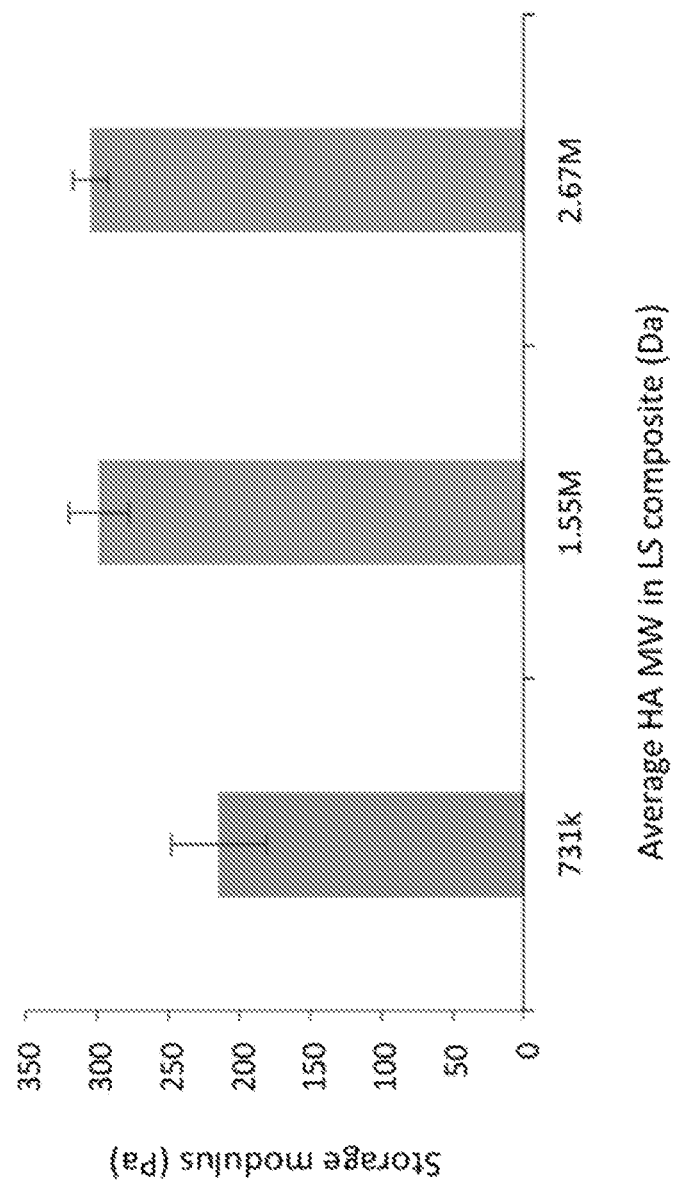

The molecular weight of hyaluronic acid affects the overall properties of the composite (FIG. 4B). Allergan and other dermal filler manufacturers also recognize the significance of HA molecular weight on product persistence. Allergan's Juvederm products are manufactured with a 2.5 MDa molecular weight HA. Further, in Juvederm patent U.S. Pat. No. 8,450,475 B2, Allergan elaborates, "In a typical embodiment of the invention, the ratio of high molecular weight to low molecular weight HA is at least about, and preferably greater than 2 (w/w≥2) with the high molecular weight HA having a molecular weight of above 1.0 MDa."

Disclosures of HA include U.S. patent application Ser. No. 12/393,884; U.S. Pat. No. 6,921,819 (a process for cross-linking solid hyaluronic acid (HA) by reacting it with a polyfunctional linker during hydration of the HA); U.S. Pat. No. 6,685,963 (acrylic particles of HA); U.S. publication 200610194758 (a method for making a hydrogel by cross linking high and low molecular weight sodium HAs); U.S. publication 2009/0036403 (cross-linking HA with a tetra functional PEG epoxide to provide "tunably" cross-linked HA); U.S. publication 2009/0143331 (a HA dermal filler with a degradation inhibitor, such as chondroitin sulphate, in order to provide a longer lasting filler); U.S. publication 2009/0143348 (HA combined with a steroid); and U.S. publication 2009/0155314 (HA combined with a botulinum toxin). Additionally, U.S. publications 2009/0148527, 2009/0093755, and 2009/0022808 disclose HA in microspheres, cross-linked with collagen, and coated with a protein, respectively. Further disclosures of HA include: WO 2009/034559 (a process for aesthetic and/or reparative treatment of the skin with compositions that contain at least one C-glycoside derivative); WO 2009/024719 (cosmetic and pharmaceutical compositions that contain HA and a C-glycoside derivative useful for filling recesses/depressions in the skin, restore volume of the body or the face, and to reduce the sign of aging); WO 2007/128923 (a method for preparing a biocompatible gel with controlled release of one or more active lipophilic and/or amphiphilic ingredients); U.S. publication 2009/0018102 (compositions containing HA and at least one retinoid or salt/derivative thereof in combination with an oligosaccharide and a HA degradation inhibitor, to treat wrinkles, lines fibroblast depletions and scars); U.S. Pat. No. 3,763,009 (a process for improving the oxidation resistance of ascorbic acid by subjecting a mixture of ascorbic acid, maltose and/or oligosaccharides to an enzyme derived from genera *Aspergillus, Penicillium* or others to enzymatically convert the mixture into ascorbic acid glucoside); U.S. Pat. No. 5,616,611 (a α-Glycosyl-L-ascorbic acid that exhibits no direct reducing activity, is stable, and is useful as a stabilizer, quality-improving agent, antioxidant, physiologically active agent, a UV-absorbent in pharmaceutical and cosmetic industries); U.S. Pat. No. 5,843,907 (the production and use of a crystalline 2-O-α-D-glucopyranosyl-L-ascorbic acid suitable for vitamin C enriching agents, food stuffs, pharmaceuticals, and cosmetics); and EP 0539196 (an industrial scale preparation of high purity 2-O-α-D-glucopyranosyl-L-ascorbic acid) and US publication 2002/0151711. Commercial products incorporating HA and/or vitamin C agents include: MESOGLOW® products, REVITACARE®, and NCTF® 135/135HA Mesotherapy products. Each of the above-cited references and printed publications are individually incorporated herein by reference in their entirety.

In an embodiment, the HA of the invention is a sterilized HA derived from bacterial fermentation. Hyaluronic acid can be produced by Group A and C strains of *Streptococcus* bacteria. As HA does not initiate an immune response, bacteria such as *Streptococcus zooepidemicus* synthesise HA as a means to encapsulate their cells and exhibit molecular mimicry to escape detection from the host's immune system (Boyce J D, Chung J Y, Adler B, *J Biotechnol*. 2000 Sep. 29; 83(1-2):153-60; Wessels M R, Moses A E, Goldberg J B, DiCesare T J, *Proc Natl Acad Sci USA*. 1991 Oct. 1; 88(19):8317-21). HA is also naturally produced by other pathogenic bacteria including *Streptococcus pyogenes, Streptococcus uberis, Pasteurella multocida* and *Cryptococcus neoformans* (Blank L M, Hugenholtz P, Nielsen L K J Mol Evol. 2008 July; 67(1):13-22; DeAngelis P L, Jing W, Drake R R, Achyuthan A M, J Biol Chem. 1998 Apr. 3; 273(14):8454-8; Jong A, Wu C H, Chen H M, Luo F, Kwon-Chung K J, Chang Y C, Lamunyon C W, Plaas A, Huang S H Eukaryot Cell. 2007 August; 6(8):1486-96).

Production of HA by bacterial fermentation has evolved steadily over the past two decades. In its early stage of development, Group A and C Streptococci that naturally produced HA were grown in fermenters and HA was purified. However, as these bacteria produce a number of toxins, alternative bacteria were sought. Once the genes that encode for the HA biosynthetic pathway were determined, a number of bacteria (*Bacillus, Agrobacterium, E. coli* and *Lactococcus*) were genetically modified to express these genes and produce HA. Subsequent work has focused on optimization of culture media and cultivation conditions (Mao Z, Chen R R, Biotechnol Prog. 2007 September-October; 23(5):1038-42; Wessels M R, Moses A E, Goldberg J B, DiCesare T J, Proc Natl Acad Sci USA. 1991 Oct. 1; 88(19):8317-21; Widner B, Behr R, Von Dollen S, Tang M, Heu T, Sloma A, Sternberg D, Deangelis P L, Weigel P H, Brown S, Appl Environ Microbiol. 2005 July; 71(7):3747-52; Sze, Brownlie, Love, 3 Biotech. 2016; 6(1):67. doi:10.1007/s13205-016-0379-9).

Delivery of Active Agents.

Any of the herein-described gel/hydrogel compositions may be utilized so as to contain an active agent and thereby act as an active agent delivery system when applied to a body surface (e.g., a site of tissue repair) in active agent-transmitting relation thereto. The release of active agents "loaded" into the present hydrogel compositions of the invention typically involves both absorption of water and desorption of the agent via a swelling-controlled diffusion mechanism. Active agent-containing hydrogel compositions may be employed, by way of example, in transdermal drug delivery systems, in wound dressings, in topical pharmaceutical formulations, in implanted drug delivery systems, in oral dosage forms, and the like.

Suitable active agents that may be incorporated into the present hydrogel compositions and delivered systemically (e.g., with a transdermal, oral, or other dosage form suitable for systemic administration of a drug) include, but are not limited to: analeptic agents; analgesic agents; anesthetic agents; antiarthritic agents; respiratory drugs, including antiasthmatic agents; anticancer agents, including antineoplastic drugs; anticholinergics; anticonvulsants; antidepressants; antidiabetic agents; antidiarrheals; anthelminthics; antihistamines; antihyperlipidemic agents; antihypertensive agents; anti-infective agents such as antibiotics and antiviral agents; antiinflammatory agents; antimigraine preparations; antinauseants; antiparkinsonism drugs; antipruritics; antipsychotics; antipyretics; antispasmodics; antitubercular agents; antiulcer agents; antiviral agents; anxiolytics; appetite suppressants; attention deficit disorder (ADD) and attention deficit hyperactivity disorder (ADHD) drugs; cardiovascular preparations including calcium channel blockers, antianginal agents, central nervous system (CNS) agents, beta-blockers and antiarrhythmic agents; central nervous system stimulants; cough and cold preparations, including decongestants; diuretics; genetic materials; herbal remedies; hormonolytics; hypnotics; hypoglycemic agents; immunosuppressive agents; leukotriene inhibitors; mitotic inhibitors; muscle relaxants; narcotic antagonists; nicotine; nutritional agents, such as vitamins, essential amino acids and fatty acids; ophthalmic drugs such as antiglaucoma agents; parasympatholytics; peptide drugs; psychostimulants; sedatives; steroids, including progestogens, estrogens, corticosteroids, androgens and anabolic agents; smoking cessation agents; sympathomimetics; tranquilizers; and vasodilators including general coronary, peripheral and cerebral. Specific active agents with which the present adhesive compositions are useful include, without limitation, anabasine, capsaicin, isosorbide dinitrate, aminostigmine, nitroglycerine, verapamil, propranolol, silabolin, foridone, clonidine, cytisine, phenazepam, nifedipine, fluacizin, and salbutamol.

For topical drug administration and/or medicated cushions (e.g., medicated footpads), suitable active agents include, by way of example, the following:

Bacteriostatic and bactericidal agents: Suitable bacteriostatic and bactericidal agents include, by way of example: halogen compounds such as iodine, iodopovidone complexes (i.e., complexes of PVP and iodine, also referred to as "povidine" and available under the tradename Betadine from Purdue Frederick), iodide salts, chloramine, chlorohexidine, and sodium hypochlorite; silver and silver-containing compounds such as sulfadiazine, silver protein acetyltannate, silver nitrate, silver acetate, silver lactate, silver sulfate and silver chloride; organotin compounds such as tri-n-butyltin benzoate; zinc and zinc salts; oxidants, such as hydrogen peroxide and potassium permanganate; aryl mercury compounds, such as phenylmercury borate or merbromin; alkyl mercury compounds, such as thiomersal; phenols, such as thymol, o-phenyl phenol, 2-benzyl-4-chlorophenol, hexachlorophen and hexylresorcinol; and organic nitrogen compounds such as 8-hydroxyquinoline, chloroquinaldol, clioquinol, ethacridine, hexetidine, chlorhexidine, and ambazone.

Antibiotic agents: Suitable antibiotic agents include, but are not limited to, antibiotics of the lincomycin family (referring to a class of antibiotic agents originally recovered from *Streptomyces lincolnensis*), antibiotics of the tetracycline family (referring to a class of antibiotic agents originally recovered from *Streptomyces aureofaciens*), and sulfur-based antibiotics, i.e., sulfonamides. Exemplary antibiotics of the lincomycin family include lincomycin, clindamycin, related compounds as described, for example, in U.S. Pat. Nos. 3,475,407, 3,509,127, 3,544,551 and 3,513,155, and pharmacologically acceptable salts and esters thereof. Exemplary antibiotics of the tetracycline family include tetracycline itself, chlortetracycline, oxytetracycline, tetracycline, demeclocycline, rolitetracycline, methacycline and doxycycline and their pharmaceutically acceptable salts and esters, particularly acid addition salts such as the hydrochloride salt. Exemplary sulfur-based antibiotics include, but are not limited to, the sulfonamides sulfacetamide, sulfobenzimide, sulfadiazine, sulfadoxine, sulfamerazine, sulfamethazine, sulfamethizole, sulfamethoxazole, and pharmacologically acceptable salts and esters thereof, e.g., sulfacetamide sodium.

Pain relieving agents: Suitable pain relieving agents are local anesthetics, including, but not limited to, acetamidoeugenol, alphadolone acetate, alfaxalone, ambucaine, amolanone, amylocaine, benoxinate, butoxycaine, biphenamine, bupivacaine, butethamine, butacaine, butaben, butanilicaine, buthalital, butoxycaine, carticaine, 2-chloroprocaine, cinchocaine, cocaethylene, cocaine, cyclomethycaine, dibucaine, dimethisoquin, dimethocaine, diperadon, dyclonine, ecgonidine, ecgonine, ethyl aminobenzoate, ethyl chloride, etidocaine, etoxadrol, .beta.-eucaine, euprocin, fenalcomine, fomocaine, hexobarbital, hexylcaine, hydroxydione, hydroxyprocaine, hydroxytetracaine, isobutyl p-aminobenzoate, kentamine, leucinocaine mesylate, levoxadrol, lidocaine, mepivacaine, meprylcaine, metabutoxycaine, methohexital, methyl chloride, midazolam, myrtecaine, naepaine, octacaine, orthocaine, oxethazaine, parethoxycaine, phenacaine, phencyclidine, phenol, piperocaine, piridocaine, polidocanol, pramoxine, prilocaine, procaine, propanidid, propanocaine, proparacaine, propipocaine, propofol, propoxycaine, pseudococaine, pyrrocaine, risocaine, salicyl alcohol, tetracaine, thialbarbital, thimylal, thiobutabarbital, thiopental, tolycaine, trimecaine, zolamine, and combinations thereof. Tetracaine, lidocaine and prilocaine are referred pain relieving agents herein.

Other topical agents that may be delivered using the present hydrogel compositions as drug delivery systems include the following: antifungal agents such as undecylenic acid, tolnaftate, miconazole, griseofulvin, ketoconazole, ciclopirox, clotrimazole and chloroxylenol; keratolytic agents, such as salicylic acid, lactic acid and urea; vesicants such as cantharidin; anti-acne agents such as organic peroxides (e.g., benzoyl peroxide), retinoids (e.g., retinoic acid, adapalene, and tazarotene), sulfonamides (e.g., sodium sulfacetamide), resorcinol, corticosteroids (e.g., triamcinolone), alpha-hydroxy acids (e.g., lactic acid and glycolic acid), alpha-keto acids (e.g., glyoxylic acid), and antibacterial agents specifically indicated for the treatment of acne, including azelaic acid, clindamycin, erythromycin, meclocycline, minocycline, nadifloxacin, cephalexin, doxycycline, and ofloxacin; skin-lightening and bleaching agents, such as hydroquinone, kojic acid, glycolic acid and other alpha-hydroxy acids, artocarpin, and certain organic peroxides; agents for treating warts, including salicylic acid, imiquimod, dinitrochlorobenzene, dibutyl squaric acid, podophyllin, podophyllotoxin, cantharidin, trichloroacetic acid, bleomycin, cidofovir, adefovir, and analogs thereof; and anti-inflammatory agents such as corticosteroids and nonsteroidal anti-inflammatory drugs (NSAIDs), where the NSAIDS include ketoprofen, flurbiprofen, ibuprofen, naproxen, fenoprofen, benoxaprofen, indoprofen, pirprofen, carprofen, oxaprozin, pranoprofen, suprofen, alminoprofen, butibufen, fenbufen, and tiaprofenic acid.

For wound dressings, suitable active agents are those useful for the treatment of wounds, and include, but are not limited to bacteriostatic and bactericidal compounds, antibiotic agents, pain relieving agents, vasodilators, tissue-healing enhancing agents, amino acids, proteins, proteolytic enzymes, cytokines, and polypeptide growth factors.

For topical and transdermal administration of some active agents, and in wound dressings, it may be necessary or desirable to incorporate a permeation enhancer into the hydrogel composition in order to enhance the rate of penetration of the agent into or through the skin. Suitable enhancers include, for example, the following: sulfoxides such as dimethylsulfoxide (DMSO) and decylmethylsulfoxide; ethers such as diethylene glycol monoethyl ether (available commercially as Transcutol) and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80) and lecithin (U.S. Pat. No. 4,783,450); the 1-substituted azacycloheptan-2-ones, particularly 1-n-dodecylcyclaza-cycloheptan-2-one (available under the trademark Azone from Nelson Research & Development Co., Irvine, Calif.; see U.S. Pat. Nos. 3,989,816, 4,316,893, 4,405,616 and 4,557,934); alcohols such as ethanol, propanol, octanol, decanol, benzyl alcohol, and the like; fatty acids such as lauric acid, oleic acid and valeric acid; fatty acid esters such as isopropyl myristate, isopropyl palmitate, methylpropionate, and ethyl oleate; polyols and esters thereof such as propylene glycol, ethylene glycol, glycerol, butanediol, polyethylene glycol, and polyethylene glycol monolaurate (PEGML; see, e.g., U.S. Pat. No. 4,568,343); amides and other nitrogenous compounds such as urea, dimethylacetamide (DMA), dimethylformamide (DMF), 2-pyrrolidone, 1-methyl-2-pyrrolidone, ethanolamine, diethanolamine and triethanolamine; terpenes; alkanones; and organic acids, particularly salicylic acid and salicylates, citric acid and succinic acid. Mixtures of two or more enhancers may also be used.

In certain other embodiments, the composite compositions of the invention comprising a gel (e.g., a hydrogel component) and a nanostructure may also comprise additional optional additive components. Such components are known in the art and can include, for example, fillers, preservatives, pH regulators, softeners, thickeners, pigments, dyes, refractive particles, stabilizers, toughening agents, detackifiers, pharmaceutical agents (e.g., antibiotics, angiogenesis promoters, antifungal agents, immunosuppressing agents, antibodies, and the like), and permeation enhancers. These additives, and amounts thereof, are selected in such a way that they do not significantly interfere with the desired chemical and physical properties of the hydrogel composition.

Absorbent fillers may be advantageously incorporated to control the degree of hydration when the adhesive is on the skin or other body surface. Such fillers can include microcrystalline cellulose, talc, lactose, kaolin, mannitol, colloidal silica, alumina, zinc oxide, titanium oxide, magnesium silicate, magnesium aluminum silicate, hydrophobic starch, calcium sulfate, calcium stearate, calcium phosphate, calcium phosphate dihydrate, woven and non-woven paper and cotton materials. Other suitable fillers are inert, i.e., substantially non-adsorbent, and include, for example, polyethylenes, polypropylenes, polyurethane polyether amide copolymers, polyesters and polyester copolymers, nylon and rayon.

The compositions can also include one or more preservatives. Preservatives include, by way of example, p-chloro-m-cresol, phenylethyl alcohol, phenoxyethyl alcohol, chlorobutanol, 4-hydroxybenzoic acid methylester, 4-hydroxybenzoic acid propylester, benzalkonium chloride, cetylpyridinium chloride, chlorohexidine diacetate or gluconate, ethanol, and propylene glycol.

The compositions may also include pH regulating compounds. Compounds useful as pH regulators include, but are not limited to, glycerol buffers, citrate buffers, borate buffers, phosphate buffers, or citric acid-phosphate buffers may also be included so as to ensure that the pH of the hydrogel composition is compatible with that of an individual's body surface.

The compositions may also include suitable softening agents. Suitable softeners include citric acid esters, such as triethylcitrate or acetyl triethylcitrate, tartaric acid esters such as dibutyltartrate, glycerol esters such as glycerol diacetate and glycerol triacetate; phthalic acid esters, such as dibutyl phthalate and diethyl phthalate; and/or hydrophilic surfactants, preferably hydrophilic non-ionic surfactants, such as, for example, partial fatty acid esters of sugars, polyethylene glycol fatty acid esters, polyethylene glycol fatty alcohol ethers, and polyethylene glycol sorbitan-fatty acid esters.

The compositions may also include thickening agents. Preferred thickeners herein are naturally occurring compounds or derivatives thereof, and include, by way of example: collagen; galactomannans; starches; starch derivatives and hydrolysates; cellulose derivatives such as methyl cellulose, hydroxypropylcellulose, hydroxyethyl cellulose, and hydroxypropyl methyl cellulose; colloidal silicic acids; and sugars such as lactose, saccharose, fructose and glucose. Synthetic thickeners such as polyvinyl alcohol, vinylpyrrolidone-vinylacetate-copolymers, polyethylene glycols, and polypropylene glycols may also be used.

In certain embodiments, the hydrogel composite of the invention comprising a hydrogel and a nanostructure further comprises a component that promotes angiogenesis. A challenge to achieving clinically relevant soft tissue regeneration prior to the present invention is that the regenerated tissue preferably should be re-vascularized. Therefore, any material that promotes soft tissue regeneration preferably should also encourage angiogenesis. One way to achieve this is through the use of heparin-containing hydrogel components, which can serve as growth factor binding sites to enrich and retain growth factors promoting angiogenesis and tissue formation.

In an embodiment, the composition further comprises and delivers an antibody. The term "antibody" is used herein in its broadest sense and includes certain types of immunoglobulin molecules comprising one or more antigen-binding domains that specifically bind to an antigen or epitope. An antibody specifically includes intact antibodies (e.g., intact immunoglobulins), antibody fragments, and multi-specific antibodies.

In some embodiments, the antibody comprises an antibody. In some aspects, the antibody is a monoclonal antibody. In some aspects, the antibody is a chimeric antibody. In some aspects, the antibody is a humanized antibody. In some aspects, the antibody is a human antibody. In some aspects, the antibody comprises an antibody fragment. In some embodiments, the antibody comprises an alternative scaffold.

The terms "full length antibody," "intact antibody," and "whole antibody" are used herein interchangeably to refer to an antibody having a structure substantially similar to a naturally occurring antibody structure and having heavy chains that comprise an Fc region. For example, when used to refer to an IgG molecule, a "full length antibody" is an antibody that comprises two heavy chains and two light chains.

The term "Fc region" means the C-terminal region of an immunoglobulin heavy chain that, in naturally occurring antibodies, interacts with Fc receptors and certain proteins of the complement system. The structures of the Fc regions of various immunoglobulins, and the glycosylation sites contained therein, are known in the art. See Schroeder and Cavacini, J. Allergy Clin. Immunol., 2010, 125:S41-52, incorporated by reference in its entirety. The Fc region may be a naturally occurring Fc region, or an Fc region modified as described in the art or elsewhere in this disclosure.

The VH and VL regions may be further subdivided into regions of hypervariability ("hypervariable regions (HVRs);" also called "complementarity determining regions" (CDRs)) interspersed with regions that are more conserved. The more conserved regions are called framework regions (FRs). Each VH and VL generally comprises three CDRs and four FRs, arranged in the following order (from N-terminus to C-terminus): FR1-CDR1-FR2-CDR2-FR3-CDR3-FR4. The CDRs are involved in antigen binding, and influence antigen specificity and binding affinity of the antibody. See Kabat et al., Sequences of Proteins of Immunological Interest 5th ed. (1991) Public Health Service, National Institutes of Health, Bethesda, Md., incorporated by reference in its entirety.

The light chain from any vertebrate species can be assigned to one of two types, called kappa (κ) and lambda (λ), based on the sequence of its constant domain.

The heavy chain from any vertebrate species can be assigned to one of five different classes (or isotypes): IgA, IgD, IgE, IgG, and IgM. These classes are also designated α, δ, ε, γ, and μ, respectively. The IgG and IgA classes are further divided into subclasses on the basis of differences in sequence and function. Humans express the following subclasses: IgG1, IgG2, IgG3, IgG4, IgA1, and IgA2.

The amino acid sequence boundaries of a CDR can be determined by one of skill in the art using any of a number of known numbering schemes, including those described by Kabat et al., supra ("Kabat" numbering scheme); Al-Lazikani et al., 1997, J. Mol. Biol., 273:927-948 ("Chothia" numbering scheme); MacCallum et al., 1996, J. Mol. Biol. 262:732-745 ("Contact" numbering scheme); Lefranc et al., Dev. Comp. Immunol., 2003, 27:55-77 ("IMGT" numbering scheme); and Honegge and Plückthun, J. Mol. Biol., 2001, 309:657-70 ("AHo" numbering scheme); each of which is incorporated by reference in its entirety.

An "antibody fragment" comprises a portion of an intact antibody, such as the antigen-binding or variable region of an intact antibody. Antibody fragments include, for example, Fv fragments, Fab fragments, F(ab')2 fragments, Fab' fragments, scFv (sFv) fragments, and scFv-Fc fragments.

"Fv" fragments comprise a non-covalently-linked dimer of one heavy chain variable domain and one light chain variable domain.

"Fab" fragments comprise, in addition to the heavy and light chain variable domains, the constant domain of the light chain and the first constant domain (CH1) of the heavy chain. Fab fragments may be generated, for example, by recombinant methods or by papain digestion of a full-length antibody.

"F(ab')2" fragments contain two Fab' fragments joined, near the hinge region, by disulfide bonds. F(ab')2 fragments may be generated, for example, by recombinant methods or by pepsin digestion of an intact antibody. The F(ab') fragments can be dissociated, for example, by treatment with 1-mercaptoethanol.

"Single-chain Fv" or "sFv" or "scFv" antibody fragments comprise a VH domain and a VL domain in a single polypeptide chain. The VH and VL are generally linked by a peptide linker. See Plückthun A. (1994). Any suitable linker may be used. In some embodiments, the linker is a (GGGGS)n (SEQ ID NO: 127). In some embodiments, n=1, 2, 3, 4, 5, or 6. See Antibodies from *Escherichia coli*. In Rosenberg M. & Moore G. P. (Eds.), The Pharmacology of Monoclonal Antibodies vol. 113 (pp. 269-315). Springer-Verlag, New York, incorporated by reference in its entirety.

"scFv-Fc" fragments comprise an scFv attached to an Fc domain. For example, an Fc domain may be attached to the C-terminal of the scFv. The Fc domain may follow the VH or VL, depending on the orientation of the variable domains in the scFv (i.e., VH-VL or VL-VH). Any suitable Fc domain known in the art or described herein may be used. In some cases, the Fc domain comprises an IgG4 Fc domain.

The term "single domain antibody" refers to a molecule in which one variable domain of an antibody specifically binds to an antigen without the presence of the other variable domain. Single domain antibodies, and fragments thereof, are described in Arabi Ghahroudi et al., FEBS Letters, 1998, 414:521-526 and Muyldermans et al., Trends in Biochem. Sci., 2001, 26:230-245, each of which is incorporated by reference in its entirety. Single domain antibodies are also known as sdAbs or nanobodies.

A "multispecific antibody" is an antibody that comprises two or more different antigen-binding domains that collectively specifically bind two or more different epitopes. The two or more different epitopes may be epitopes on the same antigen (e.g., a single TIGIT molecule expressed by a cell) or on different antigens (e.g., different TIGIT molecules expressed by the same cell, or a TIGIT molecule and a non-TIGIT molecule). In some aspects, a multi-specific antibody binds two different epitopes (i.e., a "bispecific antibody"). In some aspects, a multi-specific antibody binds three different epitopes (i.e., a "trispecific antibody"). In some aspects, a multi-specific antibody binds four different epitopes (i.e., a "quadspecific antibody"). In some aspects, a multi-specific antibody binds five different epitopes (i.e., a "quintspecific antibody"). In some aspects, a multi-specific antibody binds 6, 7, 8, or more different epitopes. Each binding specificity may be present in any suitable valency.

A "monospecific antibody" is an antibody that comprises one or more binding sites that specifically bind to a single epitope. An example of a monospecific antibody is a naturally occurring IgG molecule which, while divalent (i.e., having two antigen-binding domains), recognizes the same epitope at each of the two antigen-binding domains. The binding specificity may be present in any suitable valency.

The term "monoclonal antibody" refers to an antibody from a population of substantially homogeneous antibodies. A population of substantially homogeneous antibodies comprises antibodies that are substantially similar and that bind the same epitope(s), except for variants that may normally arise during production of the monoclonal antibody. Such variants are generally present in only minor amounts. A monoclonal antibody is typically obtained by a process that includes the selection of a single antibody from a plurality of antibodies. For example, the selection process can be the selection of a unique clone from a plurality of clones, such as a pool of hybridoma clones, phage clones, yeast clones, bacterial clones, or other recombinant DNA clones. The selected antibody can be further altered, for example, to improve affinity for the target ("affinity maturation"), to humanize the antibody, to improve its production in cell culture, and/or to reduce its immunogenicity in a subject.

The term "chimeric antibody" refers to an antibody in which a portion of the heavy and/or light chain is derived from a particular source or species, while the remainder of the heavy and/or light chain is derived from a different source or species.

"Humanized" forms of non-human antibodies are chimeric antibodies that contain minimal sequence derived from the non-human antibody. A humanized antibody is generally a human antibody (recipient antibody) in which residues from one or more CDRs are replaced by residues from one or more CDRs of a non-human antibody (donor antibody). The donor antibody can be any suitable non-human antibody, such as a mouse, rat, rabbit, chicken, or non-human primate antibody having a desired specificity, affinity, or biological effect. In some instances, selected framework region residues of the recipient antibody are replaced by the corresponding framework region residues from the donor antibody. Humanized antibodies may also comprise residues that are not found in either the recipient antibody or the donor antibody. Such modifications may be made to further refine antibody function. For further details, see Jones et al., Nature, 1986, 321:522-525; Riechmann et al., Nature, 1988, 332:323-329; and Presta, Curr. Op. Struct. Biol., 1992, 2:593-596, each of which is incorporated by reference in its entirety.

A "human antibody" is one which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies.

In an embodiment, the antibody or antigen-binding protein provided with the compositions described herein targets a particular host cell type. In an embodiment, the antibody or antibody binds to a non-host cell, such as a bacterial or fungal cell. In an embodiment, the antibody or ADP is at least bispecific and binds to at least two host targets. In an embodiment, the antibody or ADC is at least bispecific and binds to at least one host target and one non-host target. In an embodiment, the antibody or ADP is monospecific or bispecific. In an embodiment, the antibody is trispecific or tetraspecific.

In an embodiment, the antibody agonizes a receptor. In an embodiment, the antibody antagonizes a receptor.

In an embodiment, the compositions provided herein further comprise cells for delivery. In some embodiments, the cells are derived from the subject to whom they are administered. In some aspects, the cells are derived from a source other than the subject to whom they are administered. In some aspects, the cells are derived from a cell line. In some aspects, the cells are derived from a human source. In some aspects, the cells are derived from a humanized animal source.

In some aspects, the cells provided are stem cells.

In some aspects, the cells provided are fat cells (adipocytes). In some aspects, the cells provided are muscle cells, nerve cells, skin cells, or organ cells. In some aspects, the cells provided are liver cells, pancreatic cells, cardiac cells, lung cells, esophageal cells, endothelial cells, or epithelial cells.

In some aspects, the cells provided are immune cells. Immune cells provided in some embodiments are T cells or B cells. In some embodiments, the cells provided are CD-8+ T cells. In some embodiments, the cells provided are CD-4+ T cells. In some aspects, the cells provided produce a useful substance, such as insulin, collagen, or an antibody. In some embodiments, this ability is introduced via recombinant DNA.

In some embodiments, compositions provided herein further comprise small molecules for delivery, wherein the small molecule is a biologically active material. In some embodiments, the small molecule can cause pharmacological activity or anther direct effect in the diagnosis, cure, mitigation, treatment or prevention of disease or can affect the structure or function of the body.

The gel/hydrogel/nanostructure composites of the invention can also include tissue-repairing agents, such as, a number of growth factors, including epidermal growth factor (EDF), PDGF, and nerve growth factors (NGF's). For example, the compositions may include EGF. Epidermal Growth Factor (EGF) was discovered after the observation that cutaneous wounds in laboratory mice seemed to heal more rapidly when the mice were allowed to lick them. This was not simply due to some antiseptic agent in saliva (such as lysozyme). A specific growth factor, now known as EGF, was shown to be responsible. EGF is identical to urogastrone and has angiogenic properties. Transforming growth factor-alpha (TGFα) is very similar, binding to the same receptor and is even more effective in stimulating epithelial cell regeneration (epithelisation).

Thus, hydrogels of the present invention comprising EGF/TGF may advantageously be used in the acceleration of wound healing and burns, reduction in keloid scar formation (especially for burns), skin engraftment dressings, and the treatment of chronic leg ulcers.

Tissue-repairing agents useful in the present invention include a number of growth factors, including epidermal growth factor (EDF), PDGF, and nerve growth factors (NGF's). Generally, growth-promoting hormones will affect between one and four tissues. Many of the products developed from such proteins are targeted towards wound repairs of one kind or another, although there are other indications. Some of the most important tissue growth factors are described further below.

The gel/nanostructure compositions of the invention may also include one or more growth factors that may be useful in the tissue repair methods and other applications of the invention.

For example, the invention contemplates include PDGF in the compositions of the invention. Platelet-Derived Growth Factor (PDGF) is a mitogen for almost all mesenchymally-derived cells, i.e. blood, muscle, bone, cartilage, and connective tissue cells. It is a dimeric glycoprotein existing as AA or BB homodimers, or as the AB heterodimer. As with many growth factors, PDGF is now considered to be a member of a larger family of factors. In addition to PDGF, this family includes the homodimeric factors vascular endothelial growth factor (VEGF) and placental growth factor (PIGF), VEGF/PIGF heterodimers, and connective tissue growth factor (CTGF), a PDGF-like factor secreted by human vascular endothelial cells and fibroblasts. Along with NGF, TGFβ and glycoprotein hormones such as human chorionic gonadotropic hormone (hCG), PDGF is now classified as a member of the cysteine-knot growth factor superfamily. All of these factors may be used in conjunction with hydrogels of the present invention.

PDGF is produced by platelets and released in the course of blood clotting. It is just one of the growth factors that derive from these cells. PDGF attracts fibroblasts and white blood cells to the site of the injury, as well as stimulating the growth of replacement connective tissue (mainly fibroblasts and smooth muscle cells). It stimulates cell division in various cells, including those that produce collagen, so encouraging angiogenesis. It also stimulates mitogenesis, vasoconstriction, chemotaxis, enzyme activity and calcium mobilization.

Blood platelet derived growth factors may be used to restore bone and soft tissue regrowth during certain treatments using the compositions of the invention and to accelerate the healing process of chronic and acute wounds. Accordingly, hydrogel/nanostructure compositions of the present invention may advantageously comprise a platelet derived growth factor cocktail.

Hydrogel/nanostructure compositions of the present invention may be used in gene therapy for local delivery of the PDGF gene, for example. Plasmid DNA encoding PDGF is incorporated into the hydrogel matrix and granulation tissue fibroblasts, which originate in viable tissue surrounding the wound, proliferate and migrate into the matrix, acting as targets for plasmid gene transfer and expression.

The hydrogel/nanostructure compositions of the invention may also include VEGF to promote angiogenesis. Vascular Endothelial Growth Factor (VEGF—also known as vascular permeability factor) is another vascular growth factor that is a multifunctional angiogenic cytokine. It contributes to angiogenesis (blood vessel growth) both indirectly and directly by stimulating proliferation of endothelial cells at the microvessel level, causing them to migrate and to alter their generic expression. VEGF also makes theses endothelial cells hyperpermeable, causing them to release plasma proteins outside the vascular space, which causes changes in the area, contributing to angiogenesis.

The compositions of the invention may also include FGF. Fibroblast Growth Factor (FGF) is actually a family of at least 19 14 18 kD peptides belonging to the heparin-binding growth factors family and are mitogenic for cultured fibroblasts and vascular endothelial cells. They are also angiogenic in vivo and this angiogenicity is enhanced by TNF. FGF's may be used in a similar manner to EGF. bFGF, also known as FGF-2, is involved in controlling human megakaryocytopoiesis and FGFs have been shown to be effective in stimulating endothelial cell formation, and in assisting in connective tissue repair.

Hydrogel/nanostructure compositions may also comprise Keratinocyte Growth Factor (KGF), also known as FGF-7, for use in wound healing and other disorders involving epithelial cell destruction.

Transforming Growth Factors (TGF's) have the ability to transform various cell lines, and can confer, for example, the ability to grow in culture for more than a limited number of generations, growth in multiple layers rather than monolayers, and the acquisition of an abnormal karyotype. There are at least five members of the TGF family, the two most widely studied being TGF-alpha and TGF-beta. The former is mitogenic for fibroblasts and endothelial cells, angiogenic, and promotes bone resorption. Compositions also may include TGF. TGF-beta is a general mediator of cell regulation, a powerful inhibitor of cell growth, and inhibits the proliferation of many cell types. TGF-beta can antagonize the mitogenic effects of other peptide growth factors and can also inhibit the growth of many tumour cell lines. TGF-beta also has angiogenic effects and promotes collagen formation in fibroblasts. Indications for hydrogels of the present invention include chronic skin ulcers, such as neurotrophic foot ulcers in diabetic patients. Other areas include wound healing, bone repair and immunosuppressive diseases.

Hydrogel/nanostructure compositions of the present invention may be used to carry suitable cells, for example. These may be incorporated into the gel just prior to application to a wound, or other suitable area, to maximize efficacy. Suitable cells include autologous fibroblasts and keratinocytes, which are mainly responsible for dermis and epidermis formation. Separate gels each comprising one cell type may be applied consecutively or together, or one gel may comprise both cell types, but this is generally less preferred.

Hydrogel/nanostructure compositions of the present invention may usefully comprise collagen, for example. Although collagen, in this form, is unlikely to serve a useful structural function, it primarily serves as a sacrificial protein where proteolytic activity is undesirably high, thereby helping to prevent maceration of healthy tissue, for example.

Hydrogel/nanostructure compositions can also include certain enzymes. Enzymes are used in the debridement of both acute and chronic wounds. Debridement is the removal of nonviable tissue and foreign matter from a wound and is a naturally occurring event in the wound-repair process. During the inflammatory phase, neutrophils and macrophages digest and remove "used" platelets, cellular debris, and avascular injured tissue from the wound area. However, with the accumulation of significant amounts of damaged tissue, this natural process becomes overwhelmed and insufficient. Build-up of necrotic tissue then places considerable phagocytic demand on the wound and retards wound healing. Consequently, debridement of necrotic tissue is a particular objective of topical therapy and an important component of optimal wound management.

Enzymes, for example, may be incorporated into hydrogels of the present invention for topical application to provide a selective method of debridement. Suitable enzymes may be derived from various sources, such as krill, crab, papaya, bovine extract, and bacteria Commercially available, suitable enzymes include collagenase, papain/urea, and a fibrinolysin and deoxyribonuclease combination.

Enzymes for use in the present invention generally work in one of two ways: by directly digesting the components of slough (e.g., fibrin, bacteria, leukocytes, cell debris, serous exudate, DNA); or, by dissolving the collagen "anchors" that secure the avascular tissue to the underlying wound bed.

Hydrogels of the present invention may comprise Dakin's solution, if desired, generally to exert antimicrobial effects and odor control. As a debridement agent, Dakin's solution is non-selective because of its cytotoxic properties. Dakin's solution denatures protein, rendering it more easily removed from the wound. Loosening of the slough also facilitates debridement by other methods. Hydrogels comprising Dakin's solution may be changed twice daily if the goal is debridement. Periwound skin protection should generally be provided with ointments, liquid skin barrier film dressings, or solid skin barrier wafers, for example.

The gel of the present invention may be delivered by any suitable method, such as via a syringe or bellows pack (single dose delivery systems) or a multidose system, such as a pressurized delivery system or delivery via a 'bag in the can' type system (such as that published in WO98/32675). An example of a bellows pack is shown in published UK design number 2082665.

As such, the present invention also extends to a single dose delivery system comprising a gel according to the present invention, for the treatment of wounds. The invention also extends to a pressurized delivery system comprising a gel according to the present invention, and a pressurized hydrogel according to the present invention in an aerosol container capable of forming a spray upon release of pressure therefrom. Use of such delivery means allows the gel to be delivered to areas on a patient which are otherwise difficult to reach by direct application, such as on the back of a patient when the patient is lying down.

In certain embodiment, it may be advantageous to render the hydrogel compositions of the invention electrically conductive for use in biomedical electrodes and other electrotherapy contexts, i.e., to attach an electrode or other electrically conductive member to the body surface. For example, the hydrogel composition may be used to attach a transcutaneous nerve stimulation electrode, an electrosurgical return electrode, or an EKG electrode to a patient's skin or mucosal tissue. These applications involve modification of the hydrogel composition so as to contain a conductive species. Suitable conductive species are ionically conductive electrolytes, particularly those that are normally used in the manufacture of conductive adhesives used for application to the skin or other body surface, and include ionizable inorganic salts, organic compounds, or combinations of both. Examples of ionically conductive electrolytes include, but are not limited to, ammonium sulfate, ammonium acetate, monoethanolamine acetate, diethanolamine acetate, sodium lactate, sodium citrate, magnesium acetate, magnesium sulfate, sodium acetate, calcium chloride, magnesium chloride, calcium sulfate, lithium chloride, lithium perchlorate, sodium citrate and potassium chloride, and redox couples such as a mixture of ferric and ferrous salts such as sulfates and gluconates. Preferred salts are potassium chloride, sodium chloride, magnesium sulfate, and magnesium acetate, and potassium chloride is most preferred for EKG applications. Although virtually any amount of electrolyte may be present in the adhesive compositions of the invention, it is preferable that any electrolyte present be at a concentration in the range of about 0.1 to about 15 wt. % of the hydrogel composition. The procedure described in U.S. Pat. No. 5,846,558 to Nielsen et al. for fabricating biomedical electrodes may be adapted for use with the hydrogel compositions of the invention, and the disclosure of that patent is incorporated by reference with respect to manufacturing details. Other suitable fabrication procedures may be used as well, as will be appreciated by those skilled in the art.

Crosslinking

For certain applications, particularly when high cohesive strength is desired, the polymers of the gel/hydrogels of the invention may be covalently crosslinked. The disclosure contemplates that crosslinking may be desired as between the polymers of the gel/hydrogel component, but also crosslinking may be desired as between the polymers of the gel/hydrogel and the nanostructure components of the composite materials of the invention. The invention contemplates any suitable means for crosslinking polymers to one another, and crosslinking the gel/hydrogel polymers with the nanostructure components of the invention. The gel/hydrogel polymers may be covalently crosslinked to other polymers or to the nanostructures, either intramolecularly or intermolecularly or through covalent bonds. In the former case, there are no covalent bonds linking the polymers to one another or to the nanostructures, while in the latter case, there are covalent crosslinks binding the polymers to one another or to the nanostructures. The crosslinks may be formed using any suitable means, including using heat, radiation, or a chemical curing (crosslinking) agent. The degree of crosslinking should be sufficient to eliminate or at least minimize cold flow under compression. Crosslinking also includes the use of a third molecule, a "cross-linker" utilized in the cross-linking process.

"Cross-linkers" or "Cross-linking agents" may be suitably chosen from the group of poly(ethylene glycol) PEG, e.g. thiolated poly(ethylene glycol), poly(ethylene glycol) diacrylate (PEGDA), or derivatives thereof.

For thermal crosslinking, a free radical polymerization initiator is used, and can be any of the known free radical-generating initiators conventionally used in vinyl polymerization. Preferred initiators are organic peroxides and azo compounds, generally used in an amount from about 0.01 wt. % to 15 wt. %, preferably 0.05 wt. % to 10 wt. %, more preferably from about 0.1 wt. % to about 5% and most preferably from about 0.5 wt. % to about 4 wt. % of the polymerizable material. Suitable organic peroxides include dialkyl peroxides such as t-butyl peroxide and 2,2bis(t-butylperoxy)propane, diacyl peroxides such as benzoyl peroxide and acetyl peroxide, peresters such as t-butyl perbenzoate and t-butyl per-2-ethylhexanoate, perdicarbonates such as dicetyl peroxy dicarbonate and dicyclohexyl peroxy dicarbonate, ketone peroxides such as cyclohexanone peroxide and methylethylketone peroxide, and hydroperoxides such as cumene hydroperoxide and tert-butyl hydroperoxide. Suitable azo compounds include azo bis (isobutyronitrile) and azo bis (2,4-dimethylvaleronitrile). The temperature for thermally crosslinking will depend on the actual components and may be readily deduced by one of ordinary skill in the art, but typically ranges from about 80° C. to about 200° C.

Crosslinking may also be accomplished with radiation, typically in the presence of a photoinitiator. The radiation may be ultraviolet, alpha, beta, gamma, electron beam, and x-ray radiation, although ultraviolet radiation is preferred. Useful photosensitizers are triplet sensitizers of the "hydrogen abstraction" type, and include benzophenone and substituted benzophenone and acetophenones such as benzyl dimethyl ketal, 4-acryloxybenzophenone (ABP), 1-hydroxy-cyclohexyl phenyl ketone, 2,2-diethoxyacetophenone and 2,2-dimethoxy-2-phenylaceto-phenone, substituted alpha-ketols such as 2-methyl-2-hydroxypropiophenone, benzoin ethers such as benzoin methyl ether and benzoin isopropyl ether, substituted benzoin ethers such as anisoin methyl ether, aromatic sulfonyl chlorides such as 2-naphthalene sulfonyl chloride, photoactive oximes such as 1-phenyl-1,2-propanedione-2-(O-ethoxy-carbonyl)-oxime, thioxanthones including alkyl- and halogen-substituted thioxanthones such as 2-isopropylthioxanthone, 2-chlorothioxanthone, 2,4 dimethyl thioxanone, 2,4 dichlorothioxanone, and 2,4-diethyl thioxanone, and acyl phosphine oxides. Radiation having a wavelength of 200 to 800 nm, preferably, 200 to 500 nm, is preferred for use herein, and low intensity ultraviolet light is sufficient to induce crosslinking in most cases. However, with photosensitizers of the hydrogen abstraction type, higher intensity UV exposure may be necessary to achieve sufficient crosslinking. Such exposure can be provided by a mercury lamp processor such as those available from PPG, Fusion, Xenon, and others. Crosslinking may also be induced by irradiating with gamma radiation or an electron beam. Appropriate irradiation parameters, i.e., the type and dose of radiation used to effect crosslinking, will be apparent to those skilled in the art.

Suitable chemical curing agents, also referred to as chemical cross-linking "promoters," include, without limitation, polymercaptans such as 2,2-dimercapto diethylether, dipentaerythritol hexa(3-mercaptopropionate), ethylene bis(3-mercaptoacetate), pentaerythritol tetra(3-mercaptopropionate), pentaerythritol tetrathioglycolate, polyethylene glycol dimercaptoacetate, polyethylene glycol di(3-mercaptopropionate), trimethylolethane tri(3-mercaptopropionate), trimethylolethane trithioglycolate, trimethylolpropane tri(3- mercaptopropionate), trimethylolpropane trithioglycolate, dithioethane, di- or trithiopropane and 1,6-hexane dithiol. The crosslinking promoter is added to the uncrosslinked hydrophilic polymer to promote covalent crosslinking thereof, or to a blend of the uncrosslinked hydrophilic polymer and the complementary oligomer, to provide crosslinking between the two components.

The polymers and/or nanostructures may also be crosslinked prior to admixture with the complementary oligomer. In such a case, it may be preferred to synthesize the polymer in crosslinked form, by admixing a monomeric precursor to the polymer with multifunctional comonomer and copolymerizing. Examples of monomeric precursors and corresponding polymeric products are as follows: N-vinyl amide precursors for a poly(N-vinyl amide) product; N-alkylacrylamides for a poly(N-alkylacrylamide) product; acrylic acid for a polyacrylic acid product; methacrylic acid for a polymethacrylic acid product; acrylonitrile for a poly(acrylonitrile) product; and N-vinyl pyrrolidone (NVP) for a poly(vinylpyrrolidone) (PVP) product. Polymerization may be carried out in bulk, in suspension, in solution, or in an emulsion. Solution polymerization is preferred, and polar organic solvents such as ethyl acetate and lower alkanols (e.g., ethanol, isopropyl alcohol, etc.) are particularly preferred. For preparation of hydrophilic vinyl polymers, synthesis will typically take place via a free radical polymerization process in the presence of a free radical initiator as described above. The multifunctional comonomer include, for example, bisacrylamide, acrylic or methacrylic esters of diols such as butanediol and hexanediol (1,6-hexane diol diacrylate is preferred), other acrylates such as pentaerythritol tetraacrylate, and 1,2-ethylene glycol diacrylate, and 1,12-dodecanediol diacrylate. Other useful multifunctional crosslinking monomers include oligomeric and polymeric multifunctional (meth)acrylates, e.g., poly(ethylene oxide) diacrylate or poly(ethylene oxide) dimethacrylate; polyvinylic crosslinking agents such as substituted and unsubstituted divinylbenzene; and difunctional urethane acrylates such as EBECRYL 270 and EBECRYL 230 (1500 weight average molecular weight and 5000 weight average molecular weight acrylated urethanes, respectively—both available from UCB of Smyrna, Ga.), and combinations thereof. If a chemical crosslinking agent is employed, the amount used will preferably be such that the weight ratio of crosslinking agent to hydrophilic polymer is in the range of about 1:100 to 1:5. To achieve a higher crosslink density, if desired, chemical crosslinking is combined with radiation curing.

Nanostructures

The nanostructure components of the invention may be in any suitable form including fibers, filaments, mesh sections, branched filaments or networks, sheets, or shaped particles. The nanostructures may also comprise any suitable chemical functional groups to facilitate the covalent or noncovalent crosslinking between the nanostructures and the polymers of the hydrogels of the invention. Method, techniques, and materials are well known in the art for making and functionalizing nano structures.

In certain embodiments, microfabrication methods are used to make the nanostructures of the invention. In various embodiments, the disclosed devices can be assembled and/or manufactured using any suitable microfabrication technique. Such methods and techniques are widely known in the art.

Microfabrication processes that can be used in making the nanostructures disclosed herein include lithography; etching techniques, such as lasers, plasma etching, photolithography, or chemical etching such as wet chemical, dry and photoresist removal; or by solid free form techniques, including three-dimensional printing (3DP), stereolithography (SLA), selective laser sintering (SLS), ballistic particle manufacturing (BPM) and fusion deposition modeling (FDM); by micromachining; thermal oxidation of silicon; electroplating and electroless plating; diffusion processes, such as boron, phosphorus, arsenic, and antimony diffusion; ion implantation; film deposition, such as evaporation (filament, electron beam, flash, and shadowing and step coverage), sputtering, chemical vapor deposition (CVD), epitaxy (vapor phase, liquid phase, and molecular beam), electroplating, screen printing, lamination or by combinations thereof. See Jaeger, Introduction to Microelectronic Fabrication (Addison-Wesley Publishing Co., Reading Mass. 1988); Runyan, et al., Semiconductor Integrated Circuit Processing Technology (Addison-Wesley Publishing Co., Reading Mass. 1990); Proceedings of the IEEE Micro Electro Mechanical Systems Conference 1987-1998; Rai-Choudhury, ed., Handbook of Microlithography, Micromachining & Microfabrication (SPIE Optical Engineering Press, Bellingham, Wash. 1997). The selection of the material that is used as the mold determines how the surface is configured to form the branching structure.

For example, state of the art processes for fabrication of Micro Electro Mechanical Systems (MEMS) utilizing photolithographic processes and methods derived from the semiconductor industry may be used. More recently developed methods include "soft lithography" (Whitesides et al, Angew chem. Int ed, 37; 550-575, (1998)) and microfluidic tectonics (U.S. Pat. No. 6,488,872, Beebe et al., Nature; 404:588-59 (2000)). Reviews and other discussions of polymer microdevice fabrication include Madou, M. J. Fundamentals of Microfabrication: The Science of Miniaturization; 2nd ed.; CRC Press: Boca Raton, 1997; Becker, H., and Locascio, L. E. "Polymer microfluidic devices." Talanta, 56(2):267-287, 2002; Quake, S. R., and Scherer, A. "From micro- to nanofabrication with soft materials." Science, 290(5496):1536-1540, 2000; and Whitesides, G. M., and Stroock, A. D. "Flexible methods for microfluidics." Physics Today, 54(6):42-48, 2001, each of which are incorporated herein by reference.

The nanostructures of the invention may also be fabricated by electrostatic spinning (also referred to as electrospinning). The technique of electrospinning of liquids and/or solutions capable of forming fibers, is well known and has been described in a number of patents, such as, for example, U.S. Pat. Nos. 4,043,331 and 5,522,879. The process of electrospinning generally involves the introduction of a liquid into an electric field, so that the liquid is caused to produce fibers. These fibers are generally drawn to a conductor at an attractive electrical potential for collection. During the conversion of the liquid into fibers, the fibers harden and/or dry. This hardening and/or drying may be caused by cooling of the liquid, i.e., where the liquid is normally a solid at room temperature; by evaporation of a solvent, e.g., by dehydration (physically induced hardening); or by a curing mechanism (chemically induced hardening).

The process of electrostatic spinning has typically been directed toward the use of the fibers to create a mat or other non-woven material, as disclosed, for example, in U.S. Pat. No. 4,043,331. Nanofibers ranging from 50 nm to 5 micrometers in diameter can be electrospun into a nonwoven or an aligned nanofiber mesh. Due to the small fiber diameters, electrospun textiles inherently possess a very high surface area and a small pore size. These properties make electrospun fabrics potential candidates for a number of applications including: membranes, tissue scaffolding, and other biomedical applications.

Electrostatically spun fibers can be produced having very thin diameters. Parameters that influence the diameter, consistency, and uniformity of the electrospun fibers include the polymeric material and cross-linker concentration (loading) in the fiber-forming combination, the applied voltage, and needle collector distance. According to one embodiment of the present invention, a nanofiber has a diameter ranging from about 1 nm to about 100 mm. In other embodiments, the nanofiber has a diameter in a range of about 1 nm to about 1000 nm. Further, the nanofiber may have an aspect ratio in a range of at least about 10 to about at least 100. It will be appreciated that, because of the very small diameter of the fibers, the fibers have a high surface area per unit of mass. This high surface area to mass ratio permits fiber-forming solutions or liquids to be transformed from liquid or solvated fiber-forming materials to solid nanofibers in fractions of a second.

The polymeric material used to form the nanofibers/nanostructures of the invention may be selected from any fiber forming material which is compatible with the cross-linking agents. Depending upon the intended application, the fiber-forming polymeric material may be hydrophilic, hydrophobic or amphiphilic. Additionally, the fiber-forming polymeric material may be a thermally responsive polymeric material.

Synthetic or natural, biodegradable or non-biodegradable polymers may form the nanofibers/nanostructures of the invention. A "synthetic polymer" refers to a polymer that is synthetically prepared and that includes non-naturally occurring monomeric units. For example, a synthetic polymer can include non-natural monomeric units such as acrylate or acrylamide units. Synthetic polymers are typically formed by traditional polymerization reactions, such as addition, condensation, or free-radical polymerizations. Synthetic polymers can also include those having natural monomeric units, such as naturally-occurring peptide, nucleotide, and saccharide monomeric units in combination with non-natural monomeric units (for example synthetic peptide, nucleotide, and saccharide derivatives). These types of synthetic polymers can be produced by standard synthetic techniques, such as by solid phase synthesis, or recombinantly, when allowed.

A "natural polymer" refers to a polymer that is either naturally, recombinantly, or synthetically prepared and that consists of naturally occurring monomeric units in the polymeric backbone. In some cases, the natural polymer may be modified, processed, derivatized, or otherwise treated to change the chemical and/or physical properties of the natural polymer. In these instances, the term "natural polymer" will be modified to reflect the change to the natural polymer (for example, a "derivatized natural polymer", or a "deglycosylated natural polymer").

Nanofiber materials, for example, may include both addition polymer and condensation polymer materials such as polyolefin, polyacetal, polyamide, polyester, cellulose ether and ester, polyalkylene sulfide, polyarylene oxide, polysulfone, modified polysulfone polymers and mixtures thereof. Exemplary materials within these generic classes include polyethylene, poly(ε-caprolactone), poly(lactate), poly(glycolate), polypropylene, poly(vinylchloride), polymethylmethacrylate (and other acrylic resins), polystyrene, and copolymers thereof (including ABA type block copolymers), poly(vinylidene fluoride), poly(vinylidene chloride), polyvinyl alcohol in various degrees of hydrolysis (87% to 99.5%) in crosslinked and non-crosslinked forms. Exemplary addition polymers tend to be glassy (a Tg greater than room temperature). This is the case for polyvinylchloride and polymethylmethacrylate, polystyrene polymer compositions, or alloys or low in crystallinity for polyvinylidene fluoride and polyvinyl alcohol materials.

In some embodiments of the invention the nanofiber/nanostructure materials are polyamide condensation polymers. In more specific embodiments, the polyamide condensation polymer is a nylon polymer. The term "nylon" is a generic name for all long chain synthetic polyamides. Another nylon can be made by the polycondensation of epsilon caprolactam in the presence of a small amount of water. This reaction forms a nylon-6 (made from a cyclic lactam—also known as epsilon-aminocaproic acid) that is a linear polyamide. Further, nylon copolymers are also contemplated. Copolymers can be made by combining various diamine compounds, various diacid compounds and various cyclic lactam structures in a reaction mixture and then forming the nylon with randomly positioned monomeric materials in a polyamide structure. For example, a nylon 6,6-6,10 material is a nylon manufactured from hexamethylene diamine and a C6 and a C10 blend of diacids. A nylon 6-6,6-6,10 is a nylon manufactured by copolymerization of epsilon aminocaproic acid, hexamethylene diamine and a blend of a C6 and a C10 diacid material.

Block copolymers can also be used as nanofiber materials. In preparing a composition for the preparation of nanofibers, a solvent system can be chosen such that both blocks are soluble in the solvent. One example is an ABA (styrene-EP-styrene) or AB (styrene-EP) polymer in methylene chloride solvent. Examples of such block copolymers are a Kraton-type of AB and ABA block polymers including styrene/butadiene and styrene/hydrogenated butadiene(ethylene propylene), a Pebax-type of epsilon-caprolactam/ethylene oxide and a Sympatex-type of polyester/ethylene oxide and polyurethanes of ethylene oxide and isocyanates.

Addition polymers such as polyvinylidene fluoride, syndiotactic polystyrene, copolymers of vinylidene fluoride and hexafluoropropylene, polyvinyl alcohol, polyvinyl acetate, amorphous addition polymers, such as poly(acrylonitrile) and its copolymers with acrylic acid and methacrylates, polystyrene, poly(vinyl chloride) and its various copolymers, poly(methyl methacrylate) and its various copolymers, can be solution spun with relative ease because they are soluble at low pressures and temperatures. Highly crystalline polymer like polyethylene and polypropylene generally require higher temperature and high-pressure solvents if they are to be solution spun.

Nanofibers can also be formed from polymeric compositions comprising two or more polymeric materials in polymer admixture, alloy format, or in a crosslinked chemically bonded structure. Two related polymer materials can be blended to provide the nanofiber with beneficial properties. For example, a high molecular weight polyvinylchloride can be blended with a low molecular weight polyvinylchloride. Similarly, a high molecular weight nylon material can be blended with a low molecular weight nylon material. Further, differing species of a general polymeric genus can be blended. For example, a high molecular weight styrene material can be blended with a low molecular weight, high impact polystyrene. A Nylon-6 material can be blended with a nylon copolymer such as a Nylon-6; 6,6; 6,10 copolymer. Further, a polyvinyl alcohol having a low degree of hydrolysis such as a 87% hydrolyzed polyvinyl alcohol can be blended with a fully or super hydrolyzed polyvinyl alcohol having a degree of hydrolysis between 98 and 99.9% and higher. All of these materials in admixture can be crosslinked using appropriate crosslinking mechanisms. Nylons can be crosslinked using crosslinking agents that are reactive with the nitrogen atom in the amide linkage. Polyvinyl alcohol materials can be crosslinked using hydroxyl reactive materials such as monoaldehydes, such as formaldehyde, ureas, melamine-formaldehyde resin and its analogues, boric acids, and other inorganic compounds, dialdehydes, diacids, urethanes, epoxies, and other known crosslinking agents. Crosslinking reagent reacts and forms covalent bonds between polymer chains to substantially improve molecular weight, chemical resistance, overall strength and resistance to mechanical degradation.

Biodegradable polymers can also be used in the preparation of the nanostructures of the invention. Examples of classes of synthetic polymers that have been studied as biodegradable materials include polyesters, polyamides, polyurethanes, polyorthoesters, polycaprolactone (PCL), polyiminocarbonates, aliphatic carbonates, polyphosphazenes, polyanhydrides, and copolymers thereof. Specific examples of biodegradable materials that can be used in connection with, for example, implantable medical devices include polylactide, polyglycolide, polydioxanone, poly(lactide-co-glycolide), poly(glycolide-co-polydioxanone), polyanhydrides, poly(glycolide-co-trimethylene carbonate), and poly(glycolide-co-caprolactone). Blends of these polymers with other biodegradable polymers can also be used.

In some embodiments, the nanofibers are non-biodegradable polymers. Non-biodegradable refers to polymers that are generally not able to be non-enzymatically, hydrolytically or enzymatically degraded. For example, the non-biodegradable polymer is resistant to degradation that may be caused by proteases. Non-biodegradable polymers may include either natural or synthetic polymers.

The inclusion of cross-linking agents within the composition forming the nanofiber, allows the nanofiber to be compatible with a wide range of support surfaces. The cross-linking agents can be used alone or in combination with other materials to provide a desired surface characteristic.

Suitable cross-linking agents include either monomeric (small molecule materials) or polymeric materials having at least two latent reactive activatable groups that are capable of forming covalent bonds with other materials when subjected to a source of energy such as radiation, electrical or thermal energy. In general, latent reactive activatable groups are chemical entities that respond to specific applied external energy or stimuli to generate active species with resultant covalent bonding to an adjacent chemical structure. Latent reactive groups are those groups that retain their covalent bonds under storage conditions but that form covalent bonds with other molecules upon activation by an external energy source. In some embodiments, latent reactive groups form active species such as free radicals. These free radicals may include nitrenes, carbine or excited states of ketones upon absorption of externally applied electric, electrochemical or thermal energy. Various examples of known or commercially available latent reactive groups are reported in U.S. Pat. Nos. 4,973,493; 5,258,041; 5,563,056; 5,637,460; or 6,278,018.

For example, the commercially available multifunctional photocrosslinkers based on trichloromethyl triazine available either from Aldrich Chemicals, Produits Chimiques Auxiliaires et de Syntheses, (Longjumeau, France), Shin-Nakamara Chemical, Midori Chemicals Co., Ltd. or Panchim S. A. (France) can be used. The eight compounds include 2,4,6-tris(trichloromethyl)-1,3,5 triazine, 2-(methyl)-4,6-bis(trichloromethyl)-1,3,5-triazine, 2-(4-methoxynaphthyl)-4,6-bis(trichloromethyl)-1,3,5-triazine, 2-(4-ethoxynaphthyl)-4,6-bis(trichloromethyl)-1,3,5-triazine, 4-(4-carboxylphenyl)-2,6-bis(trichloromethyl)-1,3,5-triazine, 2-(4-methoxyphenyl)-4,6-bis(trichloromethyl)-1,3,5-triazine, 2-(1-ethen-2-2'-furyl)-4,6-bis(trichloromethyl)-1,3,5-triazine and 2-(4-methoxystyryl)-4,6-bis(trichloromethyl)-1,3,5-triazine.

Methods of Use and Exemplary Embodiments

The gel/hydrogel/nanostructure compositions disclosed herein can be used advantageously in numerous tissue repair situations, as well as in other applications, such as providing coatings on catheters and other surgical devices and implants. The gel/hydrogel/nanostructure compositions of the invention can also be used to deliver active agents described herein, such as antibiotics, growth factors, and immunosuppressive agents.

In certain embodiments, the invention provides a method for healing a soft tissue defect comprising applying a composite material to a soft tissue defect, wherein the composite material includes a gel and a nanostructure disposed within the gel.

It will be appreciated that advantageous properties of the hydrogels/nanostructure compositions described herein include the ability to: 1) provide easy characterization and quality control; 2) integrate with existing tissue matrices; 3) directly incorporate into newly formed matrices; 4) directly include cells and bioactive factors; 5) maintain biocompatibility; 6) control bioresorption; 7) cast easily into complicated anatomical shapes due to greater structural rigidity owing to the nanostructures; and 8) exhibit the mechanical properties of native tissues such as articular cartilage.

In one application, the hydrogel/nanostructure composite compositions of the invention can be used to repair cartilage tissue. Current biologically-based surgical procedures for cartilage repair include autologous chondrocyte implantation, drilling, abrasion chondroplasty, microfracture, and mosaic arthroplasty. All these procedures treat only focal articular cartilage injuries, and not cartilage denuded joint surfaces such as seen in severe osteoarthritis and rheumatoid arthritis. Also, they use either cartilage tissue plugs or expanded chondrocytes harvested from the patient to fill cartilage defects. These tissues or chondrocytes are expected to fill the defect by synthesizing entirely de novo material, such as newly synthesized hyaline cartilage, that has integrated with existing cartilage matrices and has the biomechanical properties of normal cartilage. However, such procedures all promote the formation of a reparative tissue (fibrocartilage) rather than true hyaline cartilage with further mechanical damage to fibrocartilage thought to predispose the joint to osteoarthritis. Furthermore, the availability of endogenous cartilage as a repair material is quite limited with its acquisition presenting its own risks and morbidity to the patient. As evident from the foregoing discussion, the resulting hydrogel/nanostructure compositions disclosed herein present practical materials for promising new therapies in patients suffering from cartilage degenerative diseases.

As described herein, the present hydrogel/nanostructure compositions can be prepared having widely varying properties that are suitable for any number of synthetic tissue implantation or augmentation, as well as other clinical applications. As already described, the present materials can be used to repair cartilage defects produced as a result of either injury or disease. Defects due to injury that can be so repaired can be sports- or accident-related, and may involve only the superficial cartilage layer, or may include the underlying subchondral bone. Defects due to disease which can be repaired using the compositions described herein include those resulting from osteoarthritis and rheumatoid arthritis. Whether from injury or disease, such defects may be in either mature or growth plate cartilage. Formulations for hydrogels for synthetic growth plate cartilage may require the inclusion of unsubstituted scaffold material to allow for controlled bioresorption of the biomaterial during growth.

Another field where the hydrogel/nanostructure compositions described herein can be useful is the repair, reconstruction or augmentation of cartilaginous as well as soft tissues of the head and neck. The availability of biomaterials for soft tissue augmentation and head and neck reconstruction has remained a fundamental challenge in the field of plastic and reconstructive surgery. Significant research and investment has been undertaken for the development of a material with appropriate biological compatibility and life span. The outcomes of this research have not been promising. When placed in immunocompetent animals the structural integrity of currently proposed materials has been shown to fail as the framework is absorbed. Furthermore, though conventional synthetic materials offer excellent lifespan, they present certain unavoidable pitfalls. For example, silicones have been fraught with concerns of safety and long-term immune related effects. Synthetic polymers PTFE (gortex) and silastic offer less tissue reactivity but do not offer tissue integration and can represent long term risks of foreign body infections and extrusion. The materials described in this application will be useful to prepare a synthetic soft-tissue scaffold material for the augmentation or repair of soft-tissue defects of the head and neck. In particular, the hydrogel/nanostructure compositions, which are non-inflammatory, non-immunogenic, and which can be prepared having the appropriate degree of viscoelasticity (see description herein), could be used as an effective implantable scaffold material.

In addition, the present hydrogel/nanostructure compositions can be used, for example, as a novel, biocompatible and biocompliant materials to prepare cartilage implants which are frequently used in reconstructive procedures of the head and neck to repair cartilaginous or bony defects secondary to trauma or congenital abnormalities. Applications specific to the ear include otoplasty and auricular reconstruction, which are often undertaken to repair cartilaginous defects due to trauma, neoplasm (i.e., squamous cell carcinoma, basal cell carcinoma, and melanoma), and congenital defects such as microtia. Applications specific to the nose include cosmetic and reconstructive procedures of the nose and nasal septum. Dorsal hump augmentation, tip, shield and spreader grafts are frequently used in cosmetic rhinoplasty. Nasal reconstruction following trauma, neoplasm, autoimmune diseases such as Wegeners granulomatosis, or congenital defects require cartilage for repair. Septal perforations are difficult to manage and often fail treatment. Cartilage grafts would be ideal for these applications, as autologous or donor cartilage is often unavailable. Applications specific to the throat include laryngotracheal reconstruction, which in children usually requires harvesting costal cartilage, which is not without morbidity. Auricular and septal cartilage is often inadequate for this application. Synthetic cartilaginous materials prepared from hydrogels disclosed herein can be synthesized to suit each of the foregoing applications, based on tuning parameters of hydrogel synthesis such as reagent concentration, substitution and cross-linking rates. Laryngotracheal reconstruction is usually performed for airway narrowing due to subglottic or tracheal stenosis. The etiology may be traumatic (i.e., intubation trauma, or tracheotomy) or idiopathic. Other possibilities include chin and cheek augmentation, and use in ectropion repair of the lower eyelid, in addition to numerous craniofacial applications. It should be noted that these applications may not need cartilage with the exacting mechanical properties of articular cartilage. Inclusion of a cell population or bioactive agents may also be desirable.

The hydrogel/nanostructure compositions described herein also can be used for repair and narrowing of the nasal cavity, normally following overly aggressive surgical resection, to prevent the chronic pooling of fluid in the nasal passages that leads to infection and encrustation. Another promising application is in laryngotracheal reconstruction in both children and adults, as a result of laryngotracheal injury due for example to intubation during a surgical procedure such as cardiovascular surgery. Hydrogel/nanostructure compositions as herein described also can be used to provide cricoid ring replacements to protect the carotid artery following neck resection for cancer—the composition of the invention can be placed between the carotid artery and the skin as a protective barrier for the carotid artery against loss of the skin barrier. As a protective coating during neuronal repopulation of a resected nerve—often fibrous tissue forms faster than the neuronal repopulation preventing its eventual formation. Placement of the nerve ends within a hydrogel/nanostructure composition of the invention pre-cast tube could exclude fibrous tissue formation from the site of repopulation.

The hydrogel/nanostructure compositions of the invention can also be used for repair of soft tissue defects of any internal or external organs. For example, the materials of the invention can be used to for chin and cheek augmentation, and use in ectropion repair of the lower eyelid, in addition to numerous craniofacial applications. For cosmetic and reconstructive purposes in sites other than the head and neck, for example use as breast implants for breast augmentation, as a wound sealant, for example to fill the void left after removal of lymph nodes (i.e. due to cancer) in the breast or neck, to seal the lymphatics and abate uncontrolled fluid drainage into the resection site that may lead to infection and other complications.

In addition to the above uses, the hydrogel/nanostructure compositions described herein can be used in other tissue engineering applications to produce synthetic orthopaedic tissues, including, but not limited to, bone, tendon, ligament, meniscus and intervertebral disc, using similar strategies and methodologies as described above for the synthesis of artificial forms of cartilage. The hydrogel/nanostructure compositions also can be used to make synthetic non-orthopaedic tissues including but not limited to vocal cord, vitreous, heart valves, liver, pancreas and kidney, using similar strategies and methodologies as described above for the synthesis of artificial forms of cartilage.

Another field where the hydrogel/nanostructure compositions disclosed herein can be used is in gastrointestinal applications where it is necessary to treat or prevent the formation of scar tissue or strictures in abdominal or gastrointestinal organs. There already are a number of products at various stages of clinical and FDA approval, which generally are termed "hydrogels," that are designed or intended to be useful in the treatment and prevention of scarring and/or stricture formation. The materials of the present invention are superior to other known hydrogels in that the ones disclosed here can include a nanostructure which can provide support, shape, and strength to hydrogel materials. The hydrogel/nanostructure compositions disclosed herein can be used in similar applications as the already known hydrogels are used or intended to be used, including the following: for treatment of strictures or scarring of the gastrointestinal tract. The treatment involves injection of the hydrogel material at the site of an anticipated stricture to prevent scarring, or at a site of existing stricture after therapy to enlarge the narrowed GI tract to prevent the stricture from reoccurring.

The materials of the invention can also be used for the treatment of esophageal strictures. Esophageal strictures are a common complication of gastroesophageal reflux disease (GERD). GERD is caused by acid, bile and other injurious gastric contents refluxing into the esophagus and injuring the esophageal lining cells. Approximately 7-23% of GERD patients develop an esophageal stricture, or fibrous scarring of the esophagus. Esophageal scarring also can be caused by ablative therapies used to treat Barrett's esophagus. The major complication of such ablative therapies is that the ablative injury extends too deeply into the esophageal wall and results in an esophageal scar or stricture. Esophageal strictures prevent normal swallowing and are a major cause of patient morbidity. The materials described herein may be used to treat or prevent esophageal strictures resulting from GERD, Barrett's esophagus, and esophageal ablative therapies.

The composite materials of the invention may also be used for treatment of Crohn's disease. Crohn's disease causes strictures or scars that block off or narrow the lumen of the bowel, preventing normal bowel function. The present materials may be useful to treat or prevent such strictures.

The composite materials can also be used in methods for treating primary sclerosing cholangitis (PSC). PSC is a rare disease of the bile ducts of the liver. The bile ducts form a branching network within the liver and exit the liver via two main branches that are combined into the common bile duct which drains the liver and gallbladder of bile into the duodenum. The bile ducts are very narrow in diameter, measuring only up to 2 mm normally at their largest most distal portions, and yet they must normally drain liters of bile every day from the liver into the duodenum. Any blockage of these ducts can result in a serious condition known as jaundice, which allows many toxins and especially hemoglobin breakdown products to accumulate in the body. PSC is a scarring or structuring disease of the bile ducts within the liver and in the extrahepatic bile ducts described above that connect the liver to the small intestine. The bile duct strictures of PSC may be treated or prevented with the present hydrogel/nanostructure compositions.

The composite materials of the invention can also be used to treat chronic pancreatitis. Chronic pancreatitis is a chronic inflammatory disease of the pancreas that may be complicated by scars or strictures of the pancreatic ducts. These strictures block the drainage of pancreatic juice, which normally must exit the pancreas through a system of ducts or drainage conduits into the small intestine. The pancreatic juice contains many digestive enzymes and other elements important to normal digestion and nutrient absorption. Blockage or narrowing of the pancreatic ducts by chronic pancreatitis can results in severe complications in which the pancreas autodigests and forms life-threatening abdominal infections and or abscesses. The pancreatic strictures of chronic pancreatitis may be treated or prevented with the present hydrogels.

The presently described compositions may also be used for treatment of gallstone-induced bile duct and pancreatic duct strictures. Gallstones are a very common disorder, a principal complication of which is the formation of bile duct and pancreatic duct strictures, which may be treated or prevented with the hydrogels. for treatment of ischemic bowel disease. The intestines are prone to the formation of scars or strictures when their blood supply is compromised. Compromised blood flow is called ischemia, and can be caused by many pathologies, including cardiovascular disease, atherosclerosis, hypotension, hypovolemia, renal or hepatic disease-induced hypoalbuminemia, vasculitis, drug-induced disease, and many others. The end stage result of all of these etiologies can result in intestinal strictures that block off the bowel and prevent its normal function. The present hydrogel/nanostructure composites may be used to treat or prevent ischemic bowel strictures.

The compositions of the invention may also be used for treatment of radiation-induced intestinal strictures. Radiation therapy for cancer is associated with numerous morbidities, important among which is intestinal stricture formation. The present hydrogel composites may be used to treat or prevent radiation-induced intestinal strictures.

In addition to making synthetic tissues or repairing native tissues, the hydrogel/nanostructure composites disclosed here also can be used to provide a coating for non-biological structures or devices to be used in surgery or otherwise for in vivo implantation, such as surgical instruments, or ceramic or metal prostheses. Such a coating would provide a barrier between the non-biologic device material and living tissue. The role of hydrogels as a barrier for non-biologic devices includes, but is not limited to: 1) prevention of absorption of macromolecules and/or cells on the surfaces of non-biologic devices, which can lead to protein fouling or thrombosis at the device surface; 2) presentation of a non-toxic, non-inflammatory, non-immunogenic, biologically compatible surface for devices made from otherwise non-biologically compatible materials; 3) compatibility with device function such as diffusion of glucose for a glucose sensor, transmission of mechanical force for a pressure sensor, or endothelization of a vascular graft or stent; 4) enhancement of device function, such as providing a charge barrier to an existing size barrier in a MEMS based artificial nephron; 5) incorporation into non-biologic devices of a viable cell population entrapped within an aqueous, physiologically compatible environment; and 6) inclusion of drugs or bioactive factors such as growth factors, anti-viral agents, antibiotics, or adhesion molecules designed to encourage vascularization, epithelization or endothelization of the device.

Based on the foregoing, the hydrogel/nanostructure composites of the present invention may be used to provide a non-allergenic coating for a variety of implantable devices including an implantable glucose sensor for management of diabetes. In addition, the hydrogel/nanostructure composites may be used to provide: a charge barrier for the development of MEMS-based artificial nephrons; an aqueous, physiologically compatible environment in which embedded kidney cells such as podocytes can be incorporated into a MEMS-based artificial nephron design; and a coating for implantable MEMS devices designed for a variety of purposes including, but not limited to, drug delivery, mechanical sensing, and as a bio-detection system.

The disclosed hydrogel/nanostructure composites, and particularly a hyaluronan-based hydrogel, also may be covalently attached to silicon-based devices, e.g. through first covalent attachment of the primary amine of tyramine to the silicon surface to provide a hydroxyphenyl coated surface chemistry. This may use the same chemistry used to bind DNA that has been modified with a free amine to silicon surfaces. The HA-based hydrogel then is covalently coupled to the hydroxyphenyl coated surface by the same peroxidase driven chemistry used in its preferred cross-linking mode described above.

The hydrogel/nanostructure composites also can be used for coating non-biologic cardiovascular devices such as catheters, stents and vascular grafts. These would include devices made from materials conventionally not used because of their biological incompatibility, but which have superior design characteristics to those devices currently in use. Bioactive factors could be incorporated into the hydrogels to promote endothelization or epithelization of the hydrogel, and thus of the implanted device.

Although particular examples and uses for the hydrogel/nanostructure composites of the invention have been described herein, such specific uses are not meant to be limiting. The hydrogel/nanostructure composites of the invention can be used for any application generally used for known hydrogels, and in particular, are useful for the repair and/or regeneration of soft tissue anywhere in the body.

EXAMPLES

Example 1. In Situ Forming Composite with Reduced Inflammation Profiles

An in situ-forming composite was developed comprising 5 mg/mL of thiolated HA (HA-SH), 10 mg/mL of polycaprolactone (PCL) fibers and the concentration of PEGDA set to match the thiol concentration 1:1 with the combined acrylate and maleimide concentrations (5 mg/mL). The components were mixed together to react approximately 30 minutes before surgery in order to begin gelation, with the bulk of the gelation being completed in situ.

While gelation success was achieved in vitro and in animals (rodents and rabbits by subcutaneous (s.c.) injection), the chemistry preparation utilizing the thiolated-HA caused short-term moderate inflammation when injected in the subcutaneous rabbit model. In order to produce a composite formulation with reduced inflammation, the reactive groups between the HA and PEG were reversed, keeping an earlier formulation comprising a fiber-maleimide component.

As shown in FIG. 1A, the upward arrows indicate the injection site of the gel containing HA-SH and PEGDA; while the downward arrow indicates injection site of an alternative composition containing HA-Ac and PEGSH.

Similar inflammation profiles were observed when the chemistries were again tested in a porcine model. The gels and composites were injected subdermally into the pig inner thigh at volumes of 400 μL per injection. The tissues were imaged over the subsequent 48 hours then harvested. The skin inflammation for all groups appeared benign to the naked eye (FIG. 1B).

Under histological analysis (Masson's Trichrome staining), however, a strong acute (48 hour) immune response in thiolated-HA groups was shown as the injection site is encapsulated with definitive border between host tissue and injection, as visualized by the monocyte activation on the periphery of the injection site, red color (FIG. 1C). The HA acrylate (HA-Ac) group was more similar to the HA commercial negative control group, showing little encapsulation at the host-implant interface.

The new formulation used 5 mg/mL HA-Ac and 6 mg/mL PEGSH (PEG thiol; 4-arm 10k MW PEGSH, with twice the amount of thiol to acrylate+maleimide since that ratio gave the greatest mechanical strength). The HA-Ac had a molecular weight of 731k Da and a 10-12.5% acrylation degree. In addition, 200k HA-Ac was also tried, but the resulting gels were much weaker.

To further reduce the inflammation profile in rabbits, a 2-arm PEGSH crosslinker was used at a 1:1 stoichiometry of thiol to acrylate+maleimide. To achieve the desired storage modulus, a slightly higher initial concentration of 7 mg/mL of HA-Ac was used. The fiber component was kept at 8-10 mg/mL and set the 2-arm PEGSH to have the 1:1 stoichiometry, that with the 5k PEGSH equated to 6.9 mg/mL. The 3.4 kDa and 8 kDa molecular weights of PEGSH samples were also tested, but they were weaker gels at the same stoichiometry, the 5 kDa MW was selected as the in situ gelling formulation.

Figure 1D:
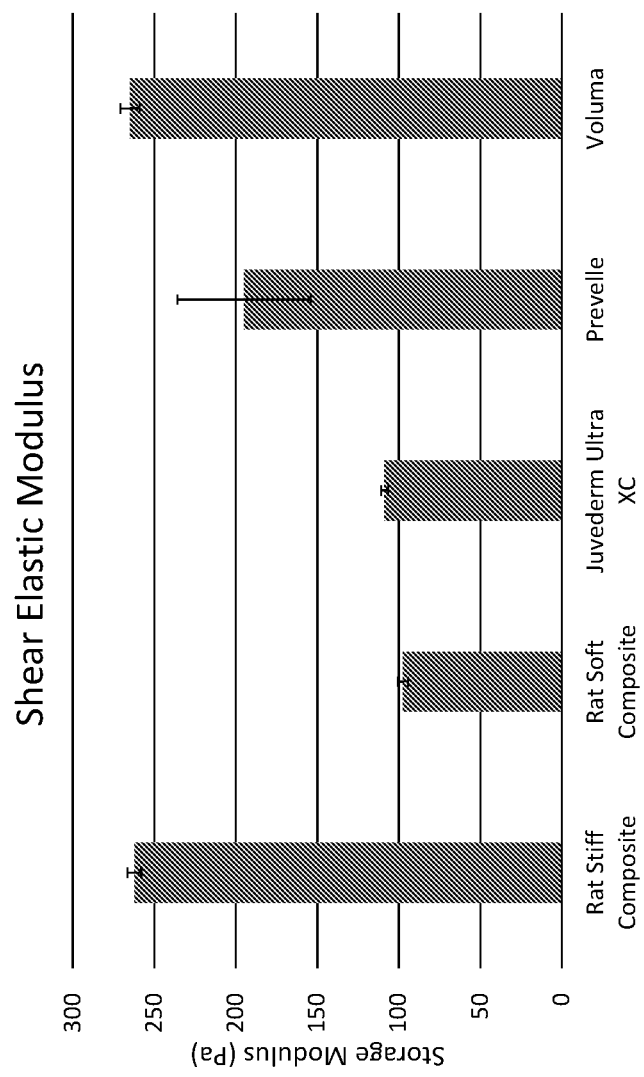

Magnetic resonance imaging (MRI) was used to evaluate two variants of this formulation (a softer formulation based on 5.5 mg/mL HA-Ac, and a stiffer formulation based upon 7.5 mg/mL; FIG. 1D, Table 2). As seen in the Figure, little post-procedural swelling was observed compared to commercial Juvederm® controls. The two composites tested were formulated at both ends of the stiffness regime of interest (Table 1). These formulations are similar in stiffness to the two tested variations of Juvederm®: Ultra XC® and Voluma®, demonstrating the tunability of the composite disclosed herein.

TABLE 2

Formulation details for the two composites tested in the rat study disclosed.

|  | Composite - Stiff-1 | Composite - Soft-1 |
| --- | --- | --- |
| HA-Ac | 7.50 mg/ml | 5.50 mg/ml |
| Fibers | 10.4 mg/ml | 11.0 mg/ml |
| PEG-SH | 4.02 mg/ml | 3.15 mg/ml |
| Resultant Shear Modulus | 255 Pa | 100 Pa |

As seen in FIG. 1E, volume retention for the composites compared to commercial controls was also assessed by MRI quantification, showing the decreased inflammation of the composites of the invention compared to the commercial control.

A

B. Example 2. Pre-Reacted Composite Beads with New Composition

To improve storage stability and make the gel simpler and more consistent for the end-user, a gel was formed comprising a pre-reacted, beaded formulation, wherein the formulation (7 mg/mL HA-Ac, 8 to 10 mg/mL of fibers with maleimide, and 6.9 m/mL of PEGSH) is fully reacted in bulk at 37° C. By pre-reacting the gel during manufacturing, the labile functional groups did not need to be protected, and the need for extensive mixing and curing by the end-user was removed.

Figure 2A:
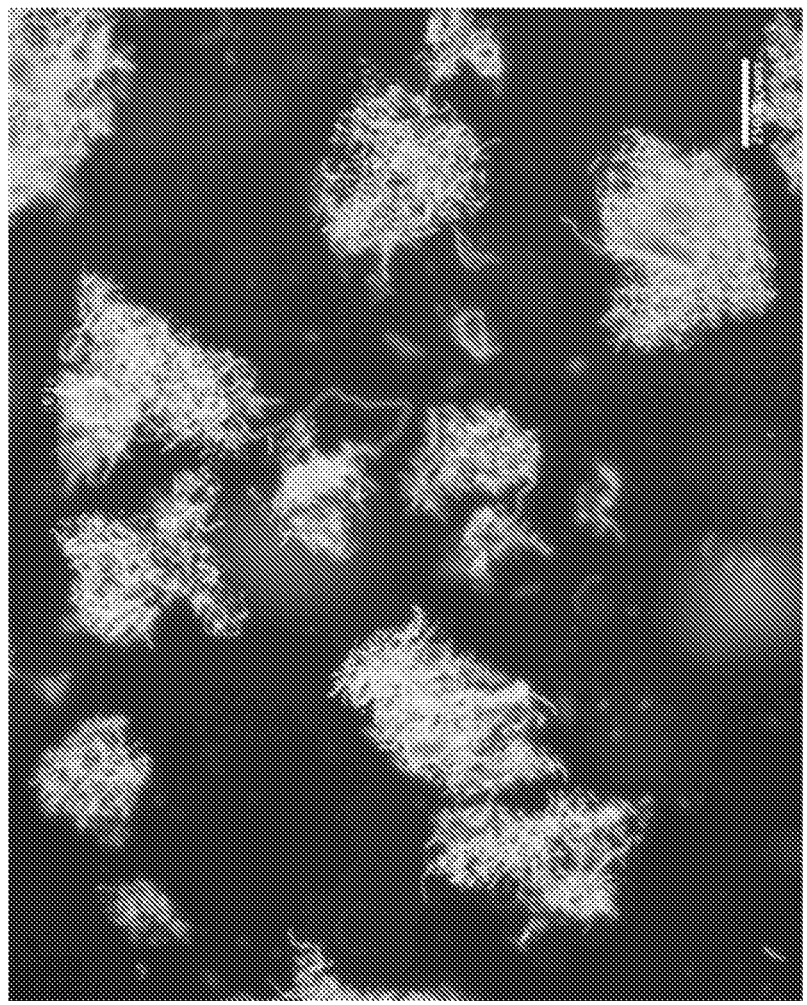
FIGS. 2A-2K are four optical microscopy images of the LS beaded composite after 100× dilution to image individual beads.
Figure 2B:
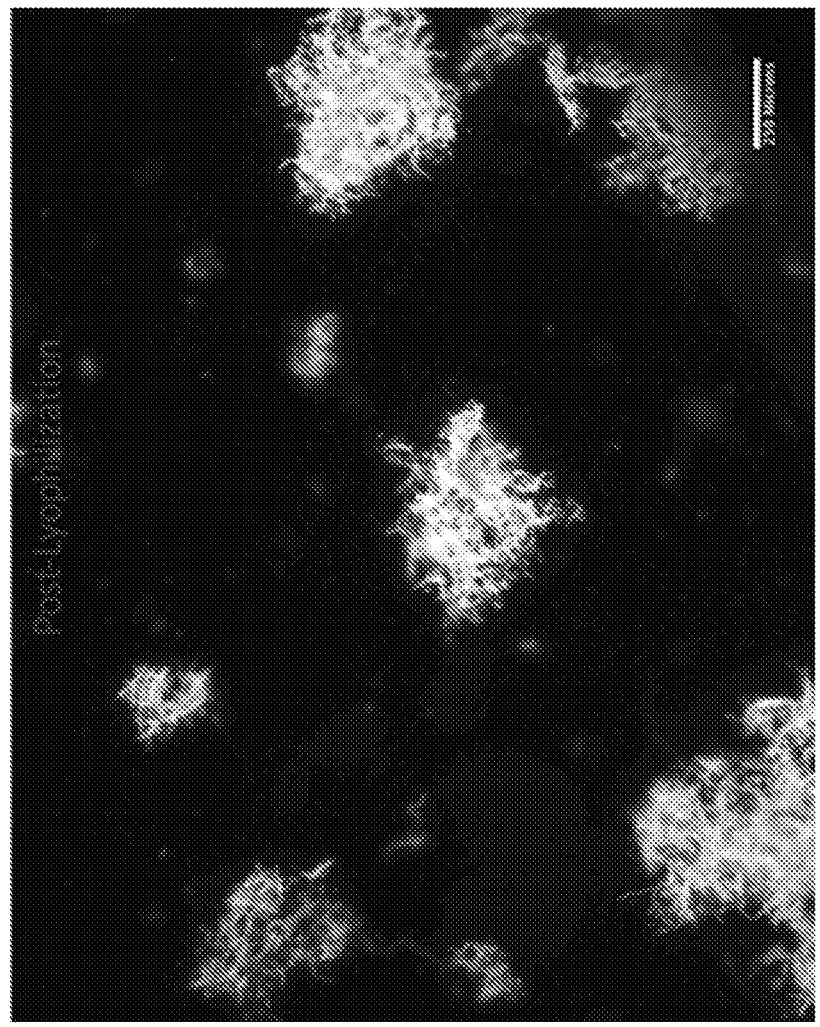
Figure 2C:
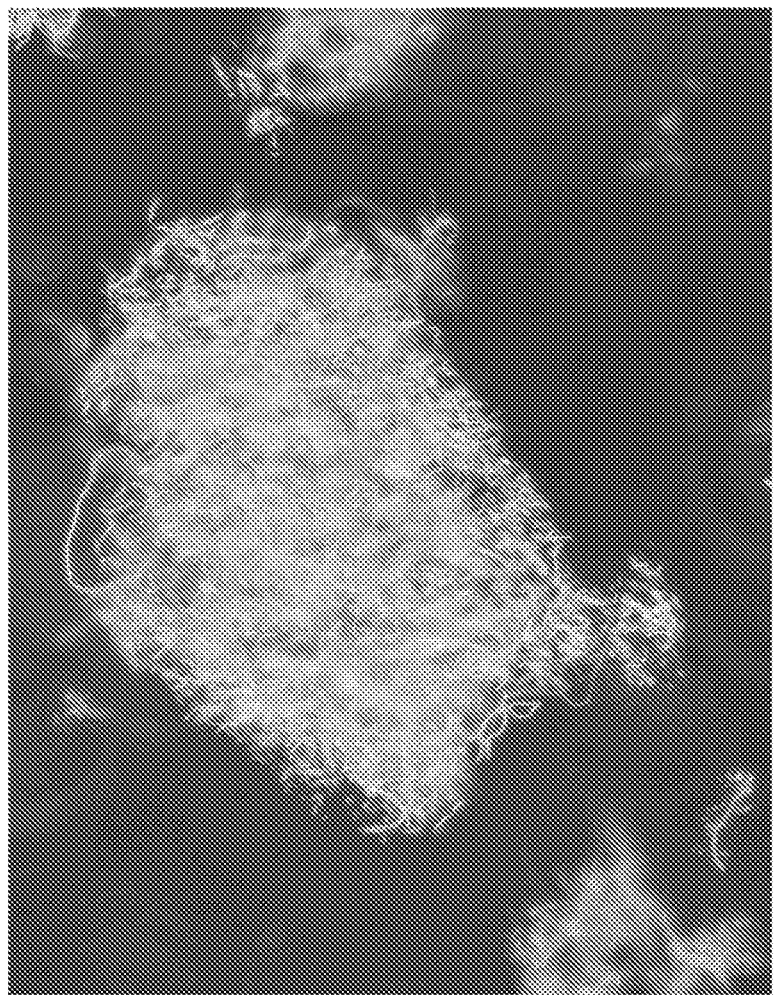
Figure 2D:
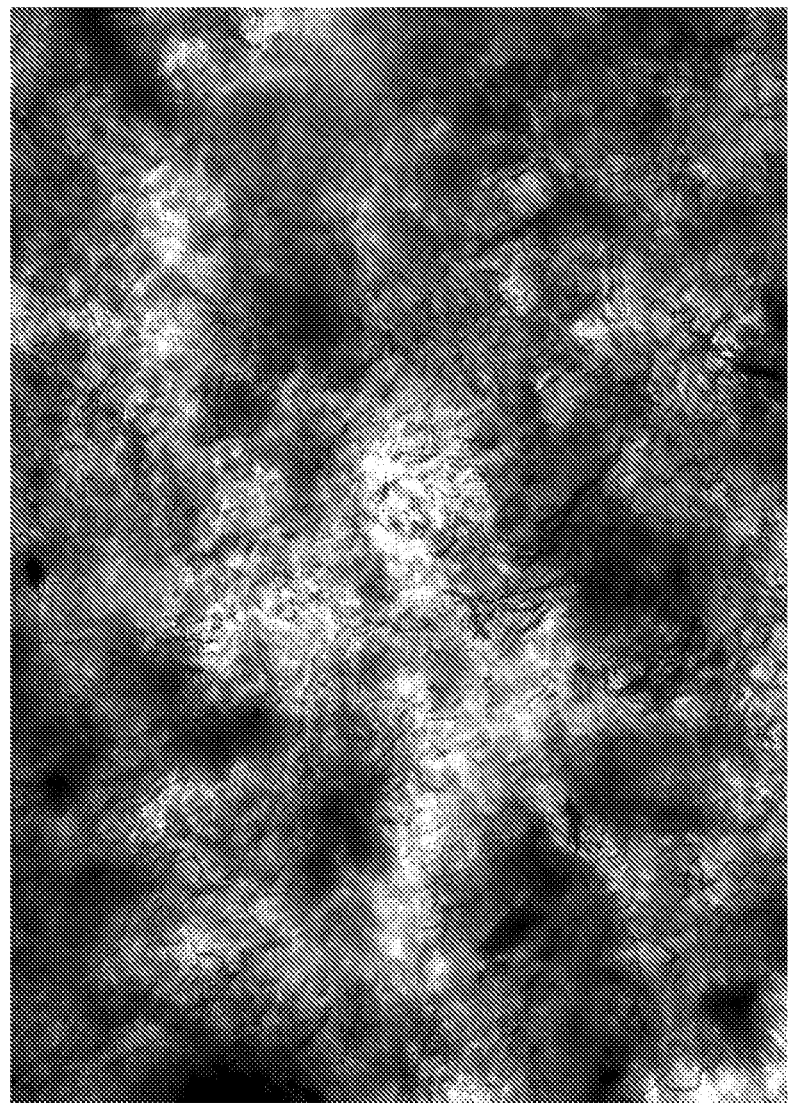
Figure 2E:
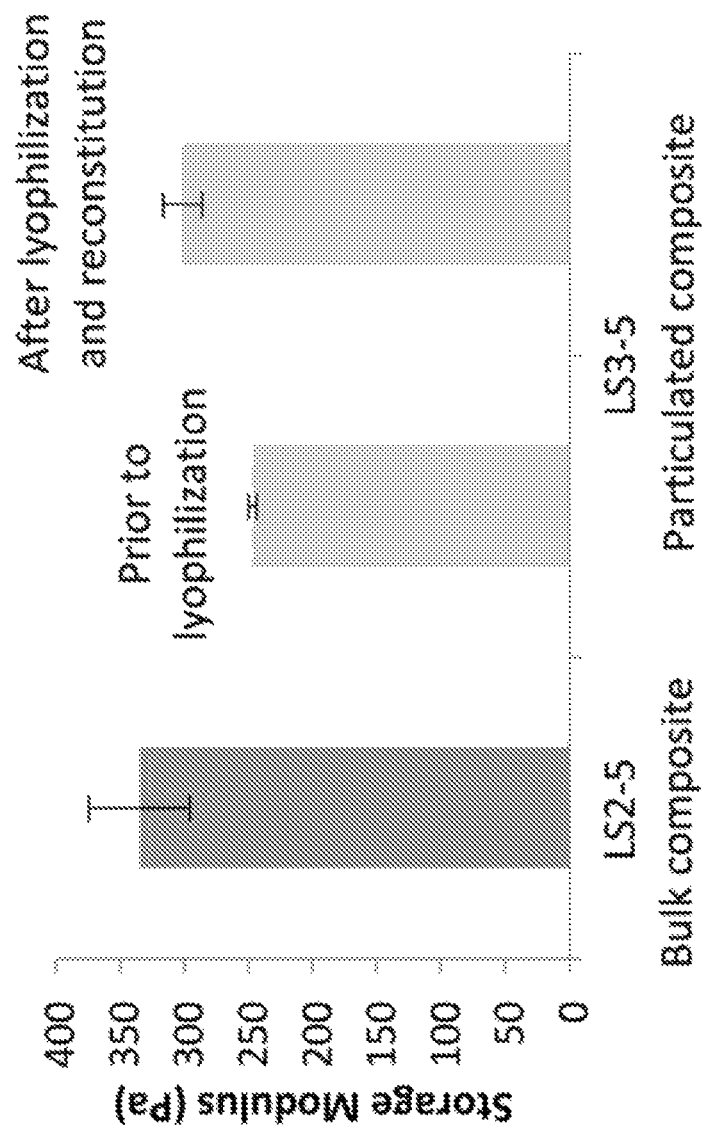
Figure 2F:
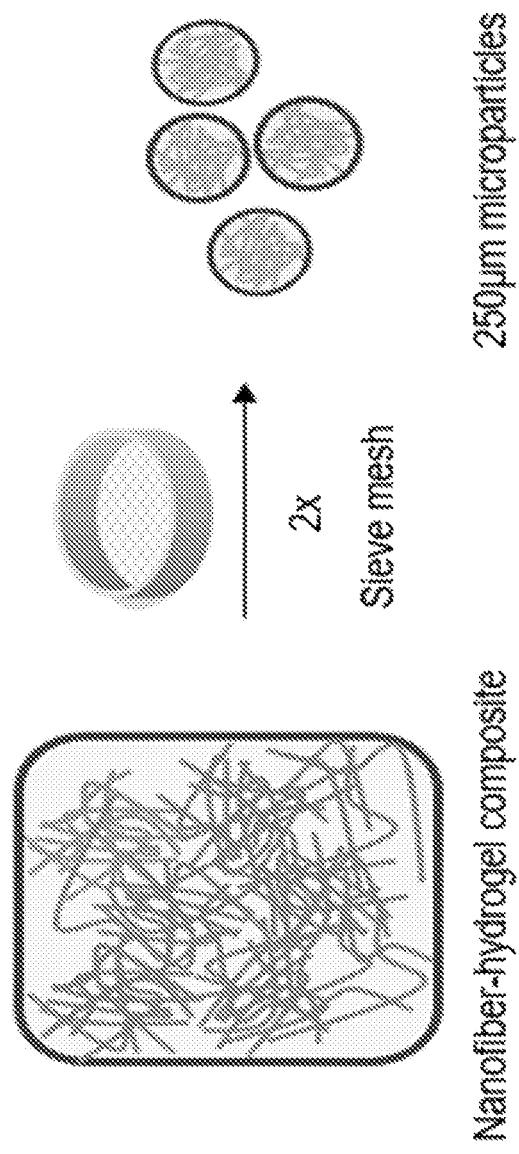
Figure 2G:
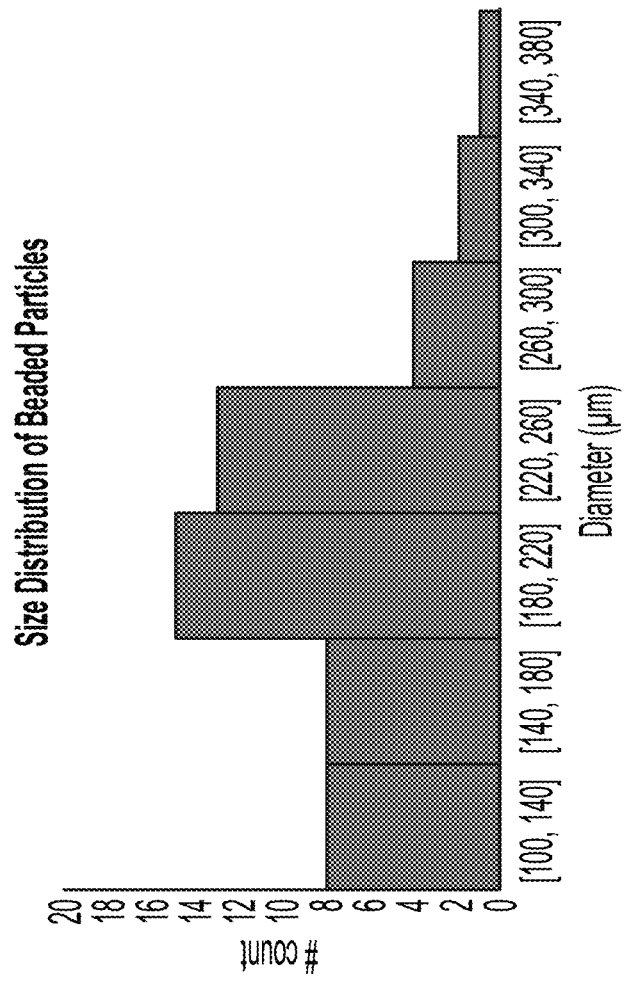
Figure 2H:
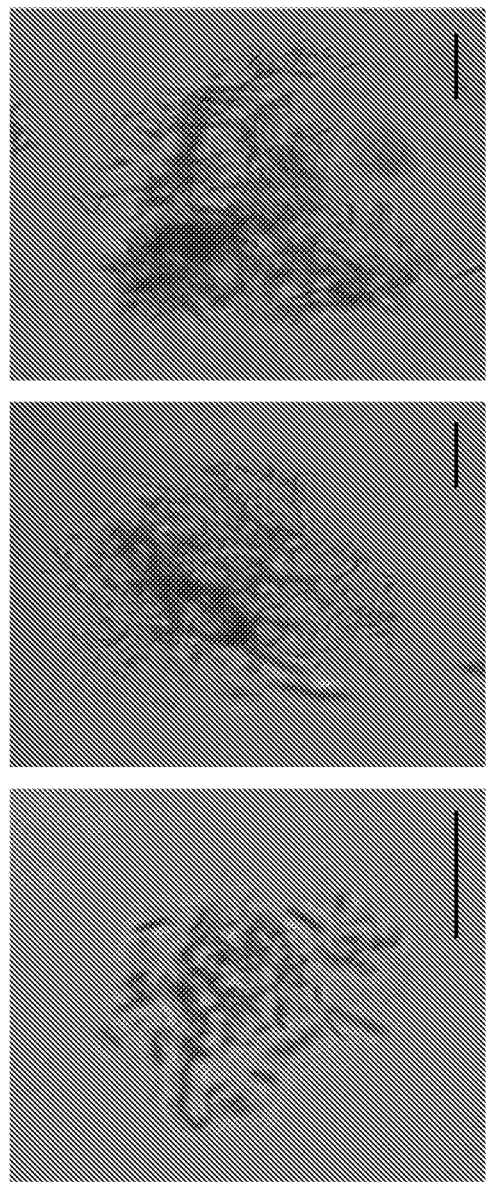

The bulk gel is formed into 150 or 250 μm beads, then lyophilized in an isotonic solution of sucrose, trehalose, and sodium chloride (to protect the microstructure during the drying process and extend the product's shelf life). The gel beads are then reconstituted with water and within seconds are ready for injection, with the same storage modulus as prior to lyophilization. Optical microscopy images of the beaded composite are shown in FIG. 2. FIG. 2A shows the composite after being particularized into 250-μm diameter beads; FIG. 2B shows the composite after being further lyophilized and rehydrated, illustrating that the composite retains its original appearance; FIG. 2C is a 10× image depicting nanofiber and hydrogel components of the beaded formulation; and FIG. 2D is an optical microscopy image of the beaded formulation in a non-diluted state.

Note the beads pictured in FIG. 2 are diluted at 100× to make visualization of the beads possible. In a non-diluted state, the resultant gel looks macroscopically identical to the pre-beaded state where individual beads are not discernable (FIG. 2D). This clarification is important for the proposed mechanism of action. The infiltrate cells from the host interact with the composite material in a similar manner to native extracellular matrix (ECM). The lyophilized beads can then be rehydrated within seconds and have a consistent gel property with a long working time for the end user. Bead sizes, lyophilization processes, and lyophilization formulations have been assessed to best maintain consistency to initial properties after being broken up into beads, lyophilized, then rehydrated. The lyophilization formulation was an important variable, as formulations dried in PBS had much larger changes to its storage modulus, indicating changes on the microstructural level. The primary drying phase required a shelf temperature maintained at −30° C. or under in order to keep the beads as individual particles—higher lyophilization temperatures resulted in a solid plug of material that could no longer be aspirated into a syringe. The non-effect of beading and lyophilization on the storage modulus for the composites described above is depicted in FIG. 2E.

Example 3. Physicochemical Characterization of Composite Beads

Determination of Size Distribution

Diameters of composite beads were measured along the longest axis of the particles under a confocal microscope image. The analysis were performed counting 51 particles. Histogram of the particles (FIG. 2G) gives the average bead size as 209.41±62.27 FIG. 2H demonstrates confocal microscope images of beads of size ~75 μm, ~150 μm and ~200 μm by measuring the longest axis within the particle.

Further characterized bead size distribution is performed using image analysis program that will use edge detection for more consistent measurements.

In some embodiments, different mesh size sieves used to process the bulk composite can yield to different histograms for the bead sizes.

In an alternative embodiment, SEM (Scanning Electron Microscopy) is used to image composite beads. Staining of the hydrogel or fibers may be required during the imaging process.

Assessing Injectability Based on Size of the Composite Beads

Figure 2I:
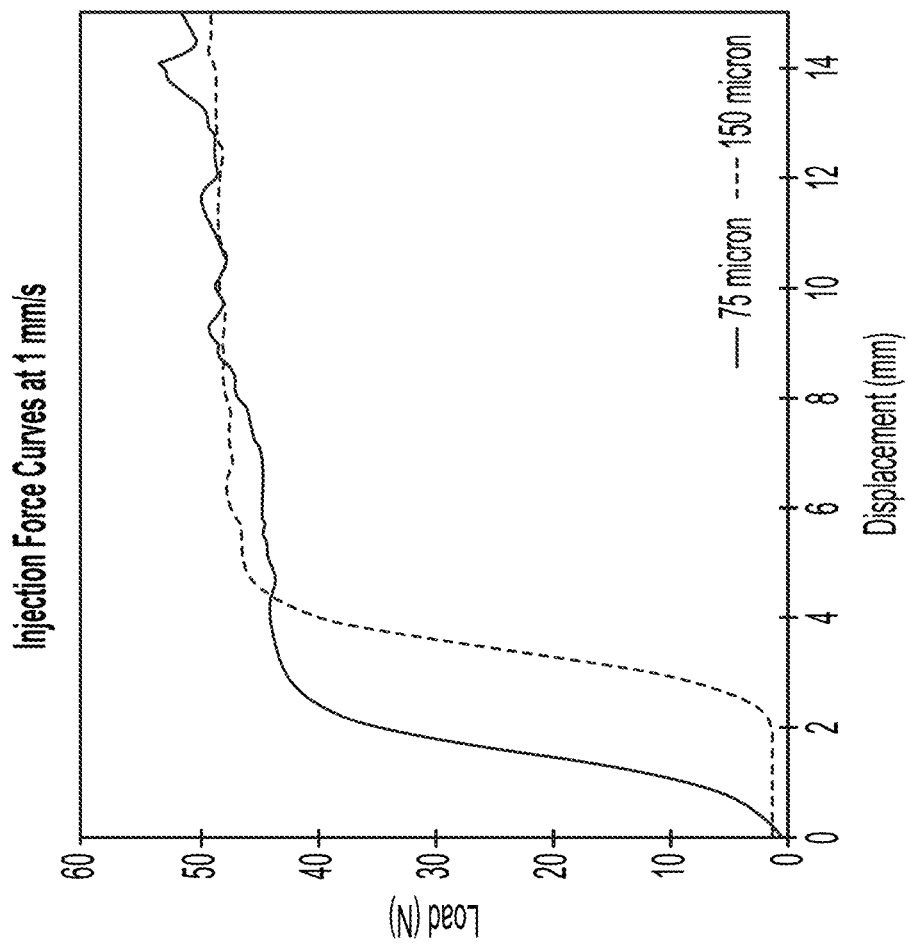

Excess gel from the Good Manufacturing Practice (GMP) lot was reprocessed to assess injectability depending on bead size. Briefly, the gel was filled into 10 cc syringes and particulated by forcing the gel through stainless steel mesh screens with defined mesh opening dimensions (25 mmm stainless steel mesh from McMaster Carr, placed in 25 min Sartorius filter holder). The gel was forced through a 250 μm then 150 μm screen. This gel was then loaded into Ice BD polycarbonate syringes to compose the "150 μm" group. The rest of the lot was then passed through an additional 75 mesh screen three times and was loaded into 1 cc BD polycarbonate syringes to form the "75 μm" group. The loaded syringes were then loaded into a syringe fixture (Instron) attached to a MTS Criterion 43 mechanical tester. The gel was injected out of the syringe through a 27 gauge needle (½" length, BD) at a crosshead speed of 1 mm/sec. Representative displacement curves are shown in FIG. 2I. The 150 μm and 75 μm groups both resulted in acceptable injection profiles. The profiles are similar as both groups produce gel beads smaller than the 210 μm inner diameter of the 27 gauge needle.

Determination of Fiber Length Distribution

Figure 2J:
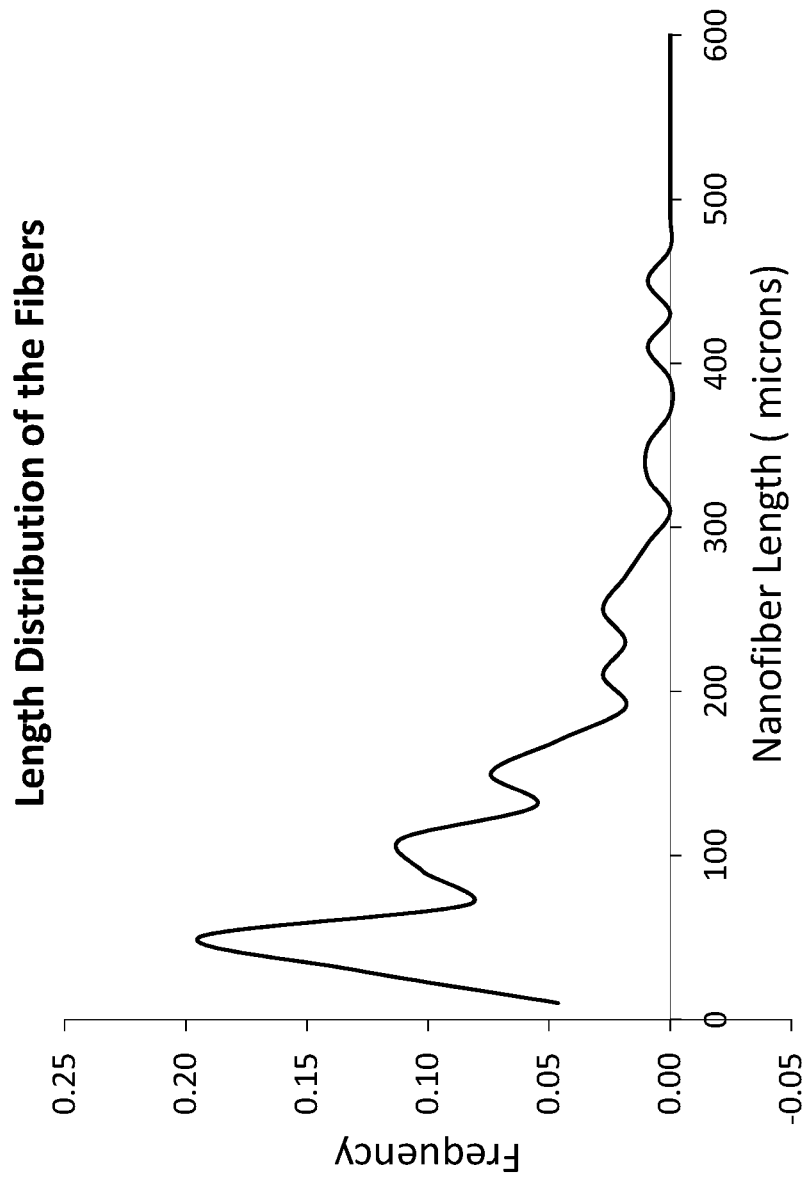
Figure 2K:
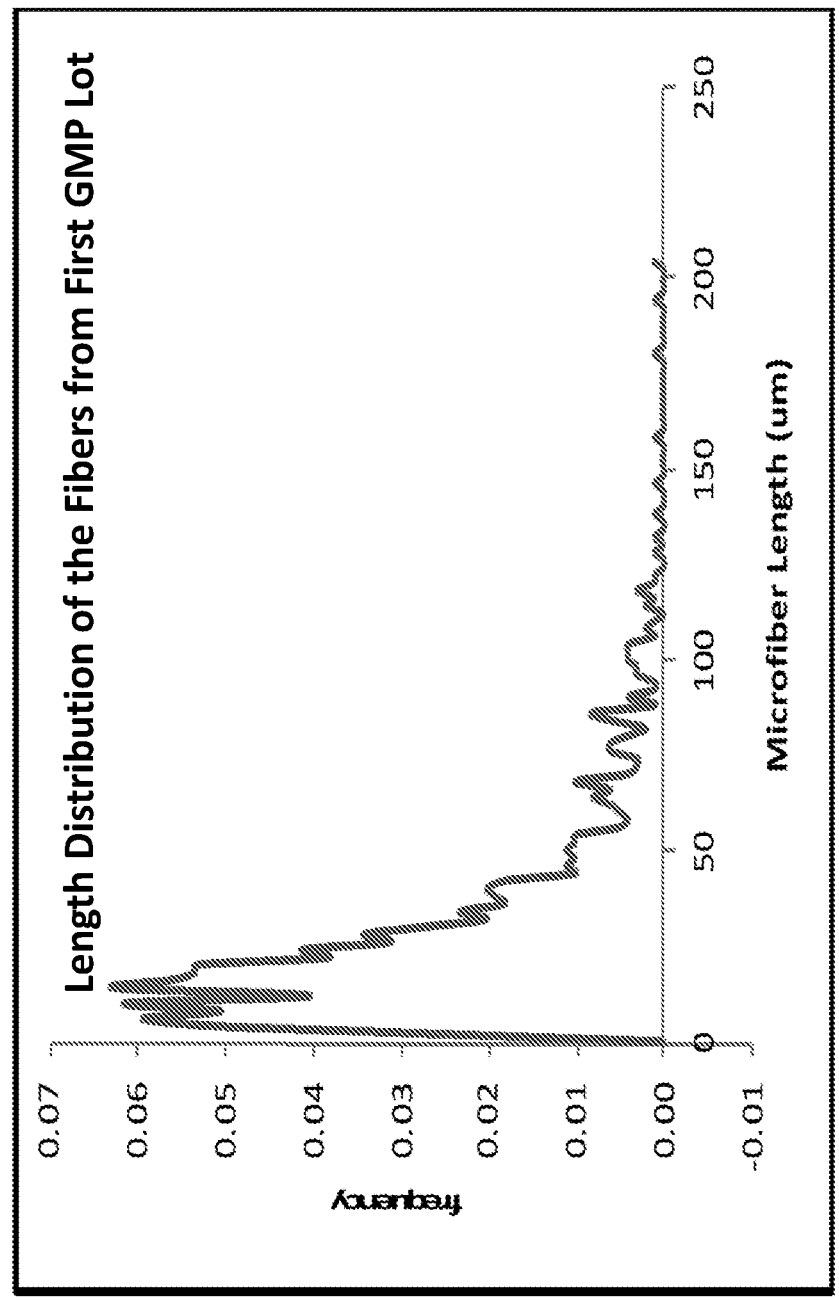

Length distribution of the fibers dispersed throughout the hydrogel material were determined through measurement of fibers seen in contrast light microscopy images using ImageJ (FIG. 2J, K). As an alternative method, SEM (Scanning Electron Microscopy) can be used to determine length distribution of the fibers.

Qualitative and Quantitative Characterization of Functional Groups (Chemical Functionalities) on Fibers and on Hydrogel The characterization of —COOH groups on fibers after plasma treatment was performed using a Toluidine Blue (TBO) assay. Microplate reader: BioTeck Synergy 2 was used to evaluate the assay. The steps of the protocol that was followed is described below:

Punch four pieces of acrylic acid-modified fiber sheet using a 0.8 cm diameter punch Place the punched fiber sheets into a 24-well plate Wash the fiber sheets with 1 mL of 0.1 mM. NaOH twice Prepare 0.5 mM toluidine blue 0 (TBO) solution in 0.1 mM NaOH Add 1 mL of 0.5 mM TBO solution into each well Place the plate on a shaker at 200 rpm and leave at room temperature for 12 h Suction out the reaction buffer Wash the fiber sheet with 0.1 mM NaOH Add 1 mL of 50% (v/v) acetic acid into each well Place the plate on a shaker at 200 rpm at room temperature for 30 min Transfer 100 μL of the supernatant into a 96 well plate Measure at 633 nm using a microplate reader with TBO in 50% (v/v) acetic acid as a standard. Typical values seen with the fibers used in these examples are COOH density of 70-100 nmol/cm$^2$.

After modification by EDC-NHS chemistry to add Maleimide (MAL) groups, Ellman's assay was performed to measure consumed thiol groups. Microplate reader: BioTeck Synergy 2 was used to evaluate the assay. The steps of the protocol that was followed is described below:

Prepare reaction buffer: 0.1 M sodium phosphate, pH 8.0, containing 1 mM EDTA

Prepare 4 mg/mL, of Ellman's reagent in the reaction buffer

Prepare 0.5 mM acetyl cysteine solution in the reaction buffer

Punch four pieces of maleimide-modified fiber sheet with the diameter of 0.8 cm

Put the fiber sheet into a 24-well plate

Wash the fiber sheet with 1 mL, of the reaction buffer

Add 0.5 mL of 0.5 mM acetyl cysteine solution into each well

Place the plate on a shaker at 200 rpm at room temperature for 4 h

Transfer 20 μL of the supernatant into a 96-well plate

Prepare the Ellman's reaction solution by diluting it 50 times in the reaction buffer Add 200 μL of the Ellman's reaction solution into each well of the 96-well plate Finally, place the 96-well plate on the shaker at 200 rpm for 15 min and measure at 412 nm using a microplate reader with acetyl cysteine in the reaction buffer as a standard. Then, calculate the consumed thiols and obtain MAL density. Typical values seen with the fibers used in these examples are MAL density of 70-100 nmol/cm$^2$.

Chemical qualification of acrylation and quantification of acrylation degree of modified hyaluronic acid was performed using Nuclear Magnetic Resonance (NMR) Spectroscopy. 20 mg of HA-Ac was added to 800 mg (D70) Deuterium oxide directly in a NMR tube, dissolved via sonication at 60° C. for 2 hours. Then, the spectrum taken were analyzed on Varian NMR system spectrometer by 1H NMR at 400 MHz. Resulting curve was processed using Varian software, Fourier transformation, baseline drift correction, phasing, integration for $_1$HNMR and baseline flattening.

The three peaks corresponding to at 6 ppm were integrated and divided over the integrated value at 2 ppm. The integrated value at 2 ppm was set to 3. The three peaks at 6 ppm correspond with the three hydrogens associated with the carbons on the acrylate group (3 total hydrogens expected per acrylate group present). The 2 ppm peak corresponds to the hydrogens associated with the acetyl group, present on each repeat unit of hyaluronic acid (3 per repeat unit). The degree of substitution is thus the summed integrated area of the three 6 ppm peaks divided by the integrated area of the 2 ppm peak to give the fraction of HA repeat units with an acrylate group. The acrylation degree percentage is that fraction converted to a percentage by multiplying by 100%.

C. Example 4. Determination of Rheological Properties of Composite Beads of Different Sizes The beads of different sizes were prepared using screens with mesh sizes of 1 mm, 250 µm, 150 µm, and 90 µm. The particles were assessed for injectability (assessment from plastic surgeons) and rheological properties. The 1000-µm beads were not injectable as their diameter was much larger than the bore size of a 25-gauge needle, while the 90-µm beads were heavily damaged in the beading process; therefore, both sizes were excluded from further study. Both the 250-µm and 150-µm bead groups injected smoothly through a 27-gauge needle. These bead sizes are of similar magnitude as the inner diameter of relevant needle sizes (25-gauge=250 µm, 27-gauge=210 µm, and 30-gauge needle=160 µm). The rheological properties of the 250 µm and 150-µm beads are shown in FIG. 3. The storage modulus decreases slightly when the solid plug of material is formed into beads, but the resulting beads are within our target stiffness range and can be made stiffer or softer by changing the initial formulation. The 250-µm and 150-µm beads showed similar rheological properties and both were suitable for future study.

D. Example 5. Intracutaneous Reactivity with Subcutaneous Injection in Rabbit Model The beaded formulation was next tested head-to-head against Juvederm Voluma® in a rabbit subcutaneous injection model. Following histology, a blinded assessment of the tissue slides was done [need to bring in method from CRO]. Table 2 shows the rating scale that was used to assess the excised samples for three different categories (inflammation, edema, and fibrosis). This is a similar test format that will be required in the ISO10993 testing package for grading intracutaneous reactivity. As shown in Table 3, the beaded formulation disclosed herein resulted in lower overall effects on inflammation, edema, and fibrosis compared to Juvederm Voluma.

TABLE 2

Rating scale for the semi-quantitative assessment used by (Mass Histology, Worcester, MA).

| | Each Category |
|---|---|
| None | 0 |
| Minimal | 1 |
| Mild | 2 |
| Moderate | 3 |
| Severe | 4 |

TABLE 3

Semi-quantitative intracutaneous reactivity assessment of the LS beaded formulation and Juvéderm Voluma.

| | n | Inflammation | Edema | Fibrosis | Sum |
|---|---|---|---|---|---|
| Beaded Formulation | 3 | 1.0 | 0.3 | 2.7 | 4.0 |
| Juvederm Voluma | 3 | 2.0 | 2.0 | 1.3 | 6.0 |

E. Example 6. Characterization of LS-1 Beaded Composite

MRI results for the initial beaded formulation LS-1 (7 mg/mL HA-Ac, 7.1 mg/mL PEGSH, 10 mg/mL fibers) were similar to that of the in situ gelling formulation described in Example 1, which had insufficient persistence in the rat model (FIG. 4A). In order to enhance the persistence of the beaded LS-1 formulation in vivo, the concentrations of the HA-Ac and fiber components were increased, and the molecular weight of the HA-Ac was increased to improve the persistence while maintaining an optimal biocompatibility profile. Note that these changes could only be made with the pre-formed nanofiber-HA hydrogel composite particles, not the previous bulk gel formulations. To test the effect of the increase of the MW of the HA, a composite using HA with an average MW of 731 kDa was generating. In an attempt to improve persistence, composites with higher molecular weight HA's were used from the same GMP source as was used for the original composite. As shown in FIG. 4B, the higher MW composite gels (1.55 M Da and 2.67 M Da) have slightly higher storage modulus compared to the initial lower molecular weight prototypes (731 kDa) but remain fully injectable through clinically-relevant gauge needles. In vivo MRI testing to demonstrate the enhanced persistence of the higher MW composites.

When optimizing the in situ forming composite formulation, the loading of polycaprolactone (PCL) fibers was kept to be less than 1% (w/v of the swollen composite) in order to make it easier to inject the bulk hydrogel composite through a 31-G needle. When optimizing the pre-formed composite particles, the injectability is less of a concern. Therefore, the reinforcement effect of PCL nanofibers at higher ratios of PCL fiber to HA hydrogel is investigated. The increased fiber loading may also improve cell migration through the matrix and enhance collagen deposition from the infiltrating cells. Further, the PCL fiber component is the most resistant to hydrolytic or enzymatic degradation processes.

Figure 4C:
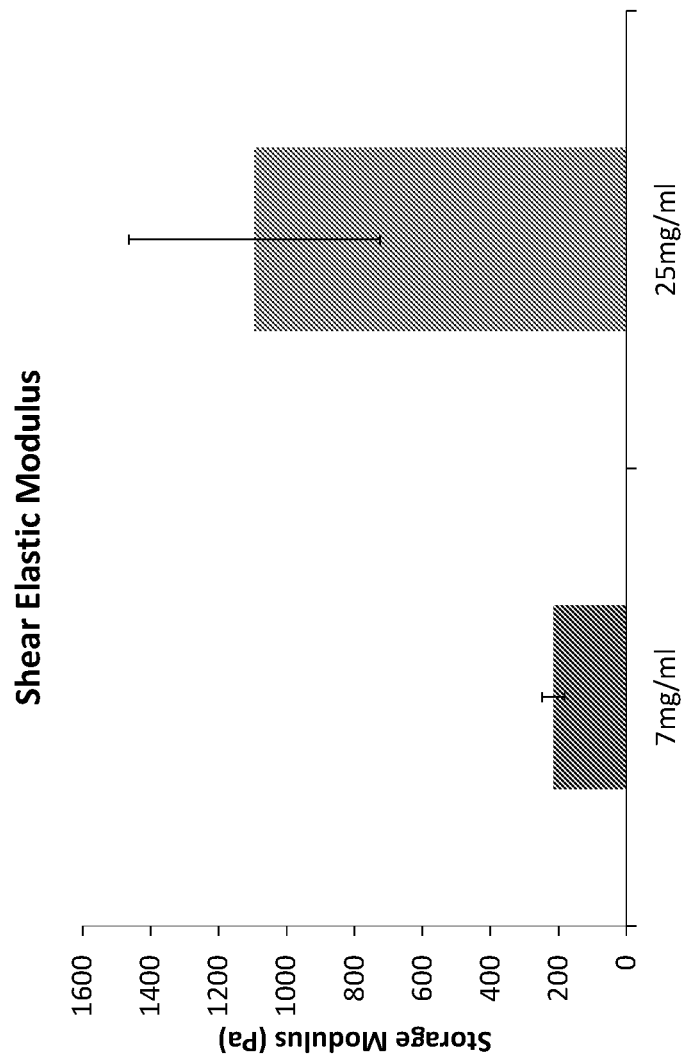
Figure 4D:
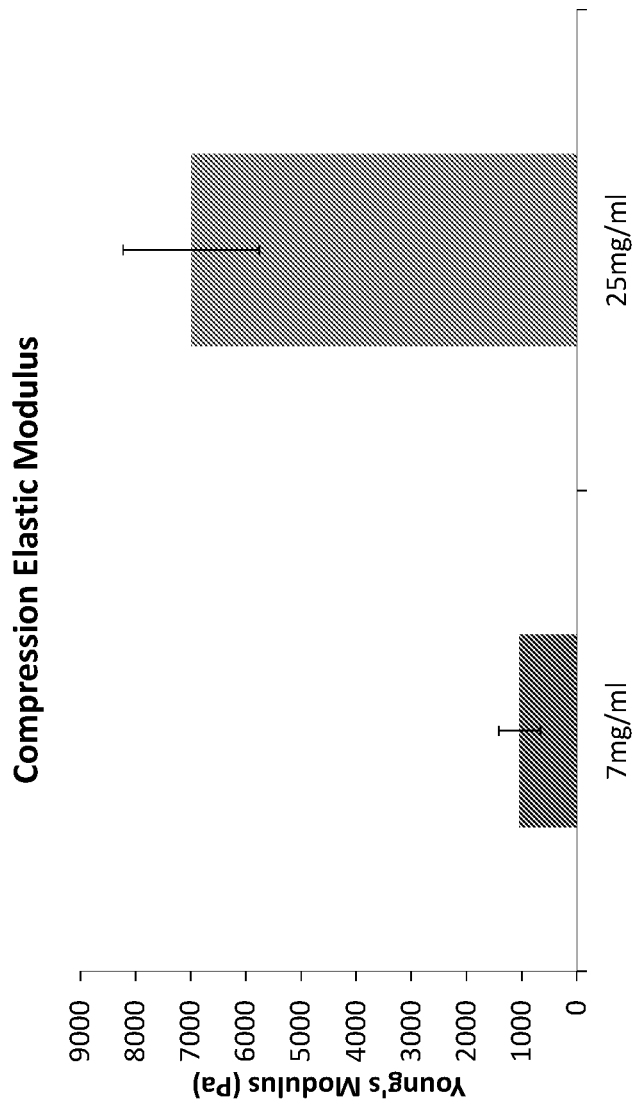

In order to test the effect of HA concentration on the shear storage modulus, a higher concentration of HA (together with a higher concentration of the PEG crosslinking agent) was used in order to increase the crosslinking density and stiffness and extend durability. This method is the first to make use of PEG crosslinkers. The crosslinking density must be optimized to allow cell infiltration. The space between the particulated composite particles may also encourage cell infiltration and migration if the stiffness is optimized. FIG. 4C shows the effect of HA concentration (mg/ml) on shear storage modulus of the composite prepared under the same HA MW and fiber loading conditions; FIG. 4D shows the effect of HA concentration (mg/ml) on compression storage modulus of the composite prepared under the same HA MW and fiber loading conditions.

In order to combine composite particles with different crosslinking density and stiffness, the pre-formed composite particles are mixed with high and low crosslinking densities (stiffness) and the advantages of both types of particles (stiffer, slower degrading, and longer lasting; vs. more porous, better cell infiltration, and vascularization) are combined. The ratio of the two types of composite particles is another novel tunable parameter.

Figure 4E:
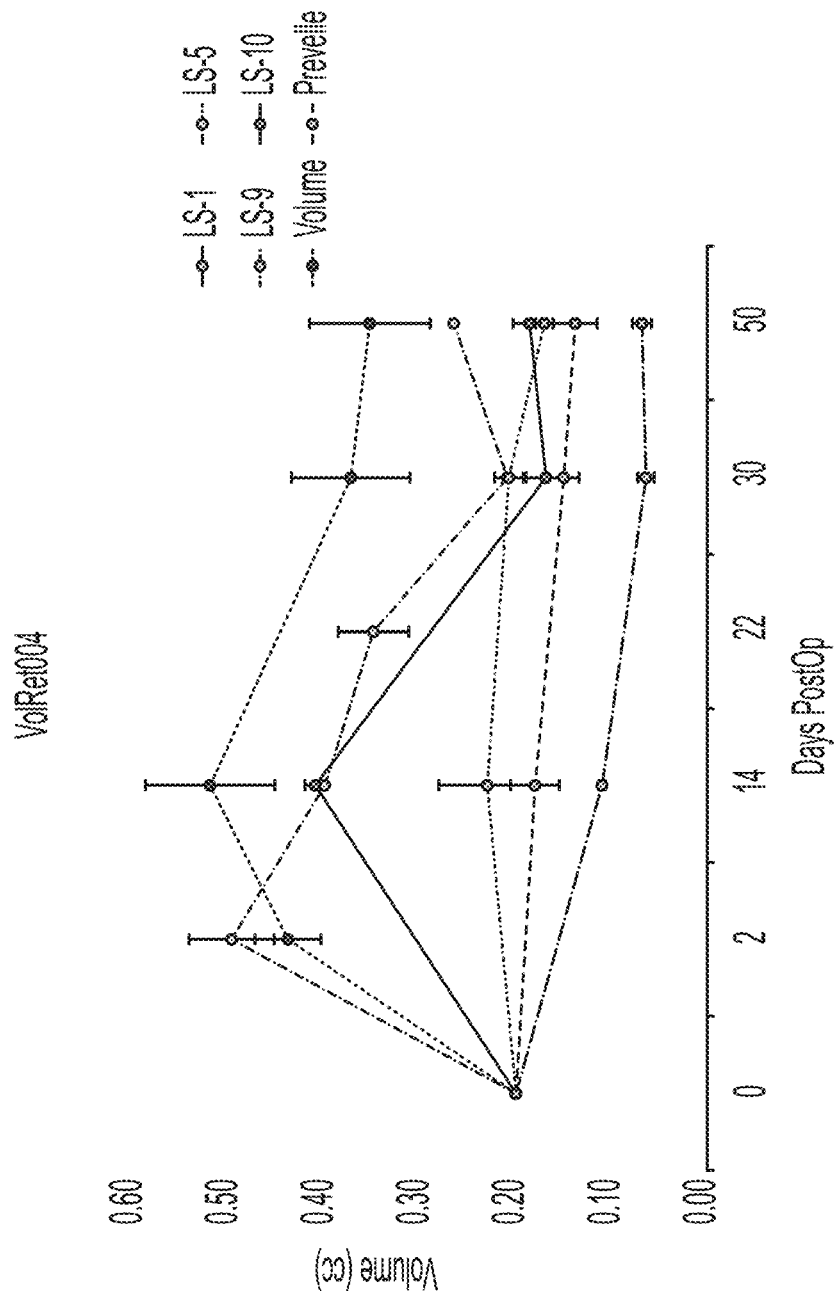
Figure 6A:
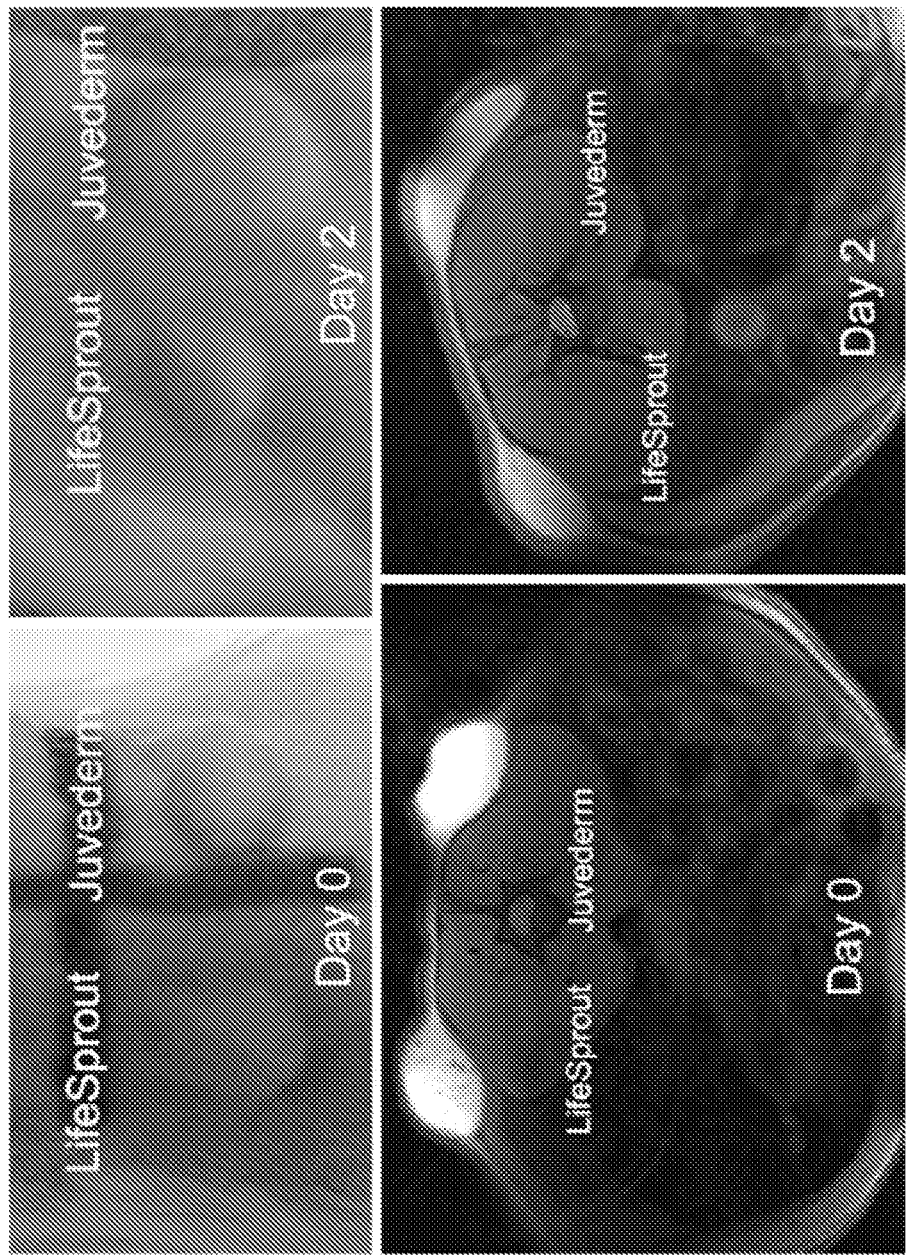
FIGS. 6A-6C show the results of swelling assessment of a pre-formed LS beaded composite compared to marketed controls.
Figure 6B:
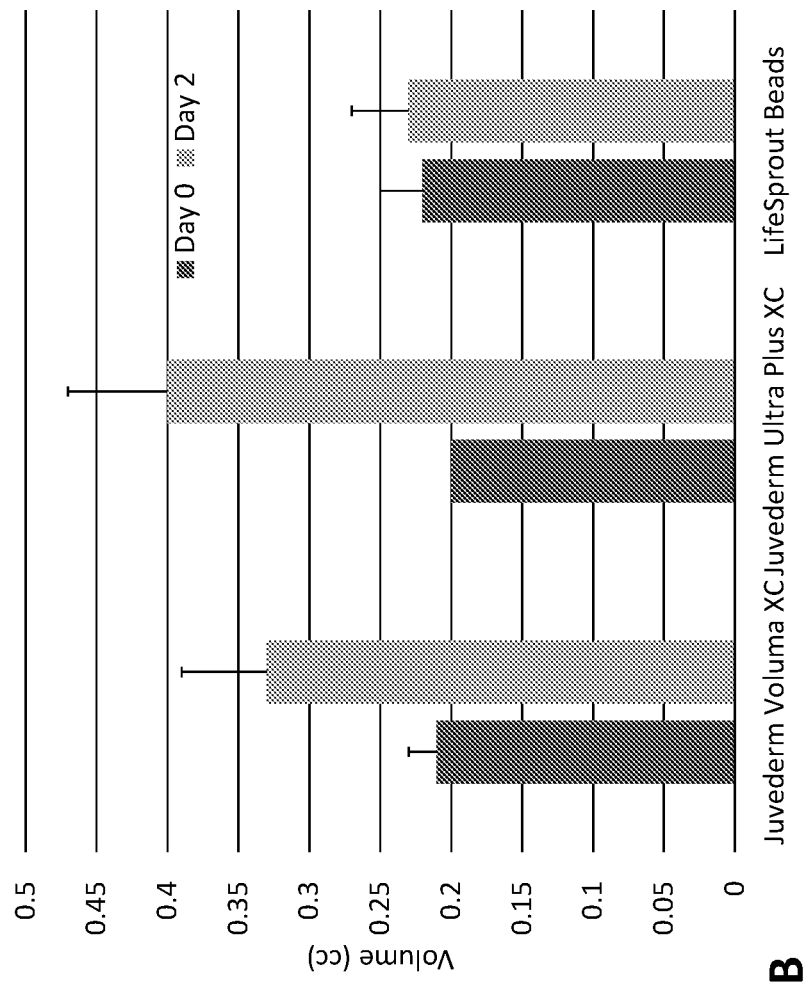
Figure 6C:
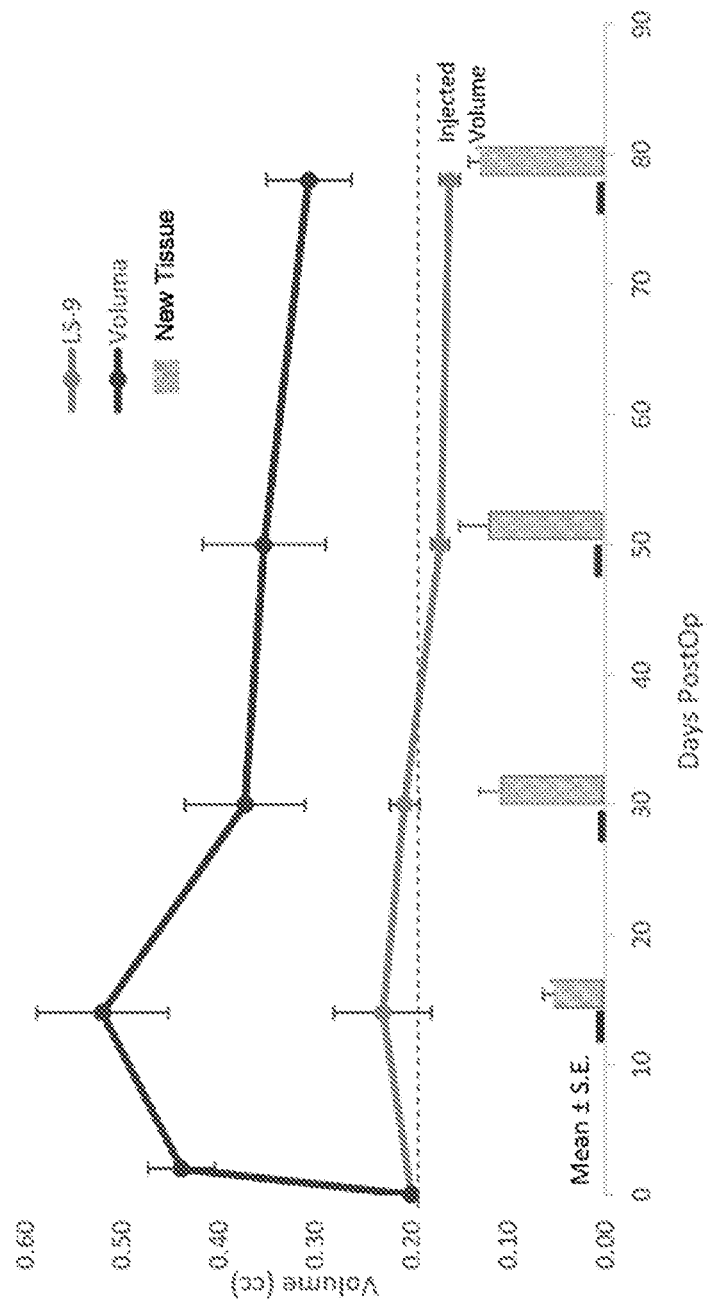

Fourteen variants of the LS formulation were made based on these optimization parameters and are being tested in an MRI volume retention model (FIG. 6A, Table 4). Through optimization of these parameters in rodent studies, we restored comparable durability to existing commercial standards while retaining enhanced tissue ingrowth and a more natural feel. Note that many of the LS-2 to LS-14 formulations were only made practical for contemplation as final formulation by the switch to the pre-beaded form and would not have been possible with the initial in-situ reaction chemistry as the gel stiffness increased (substantially in some cases) from the original LS-1 formulation as noted by storage modulus (Pa). Representative groups from this study are depicted in FIG. 4E. Juvederm® Voluma XC® served as a marketed control for the study.

the host tissue surrounding the injection site begins to infiltrate, forming new tissue. This may translate into a semi-permanent injectable, wherein the scaffold remains present for long enough for the host tissue to repair the defect site but is remodeled by native host tissue. This is in direct contrast to a traditional HA hydrogel (sans fibers) that the body encapsulates and is only present for as long as the filler is able to hold up to degradation mechanisms (FIG. 5B).

Figure 5A:
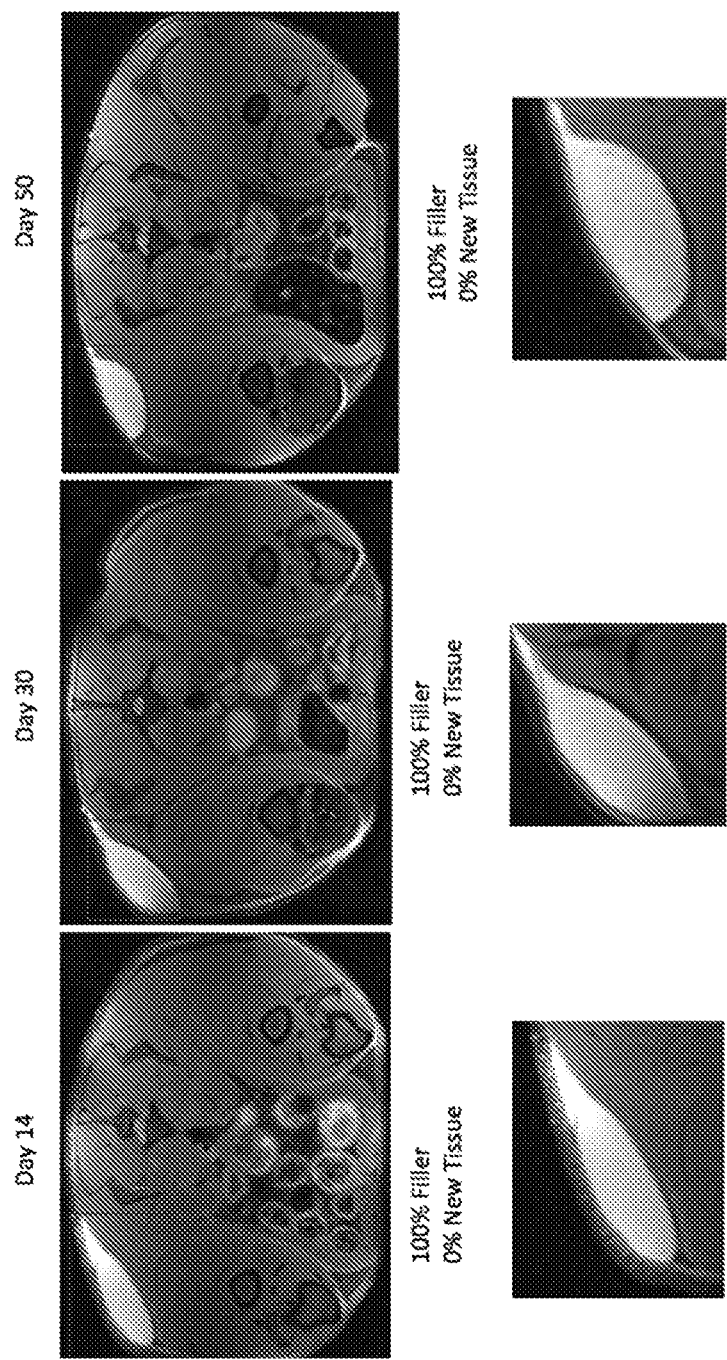
FIGS. 5A-5C are a series of MRI images showing new tissue infiltrating a LS9 scaffold injection site, as compared to a competitor product.
Figure 5B:
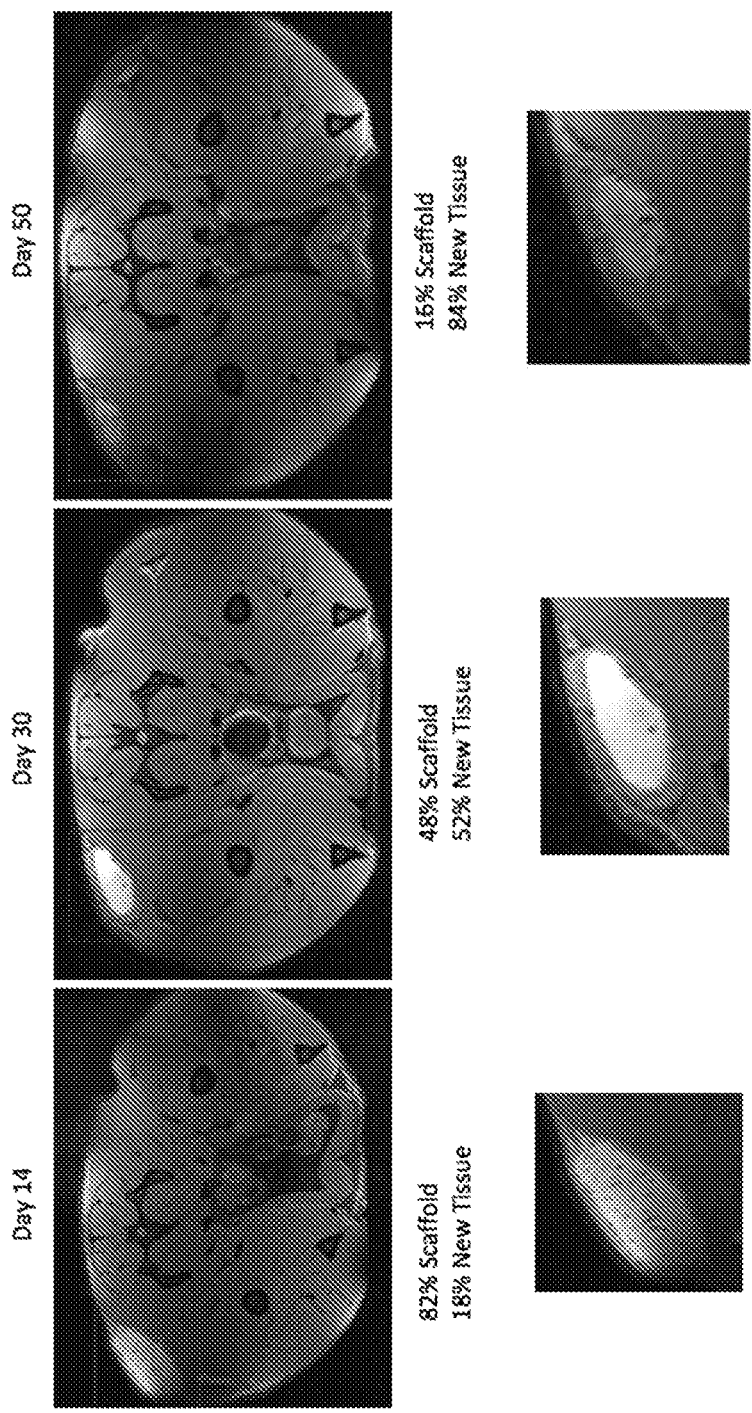
Figure 5C:
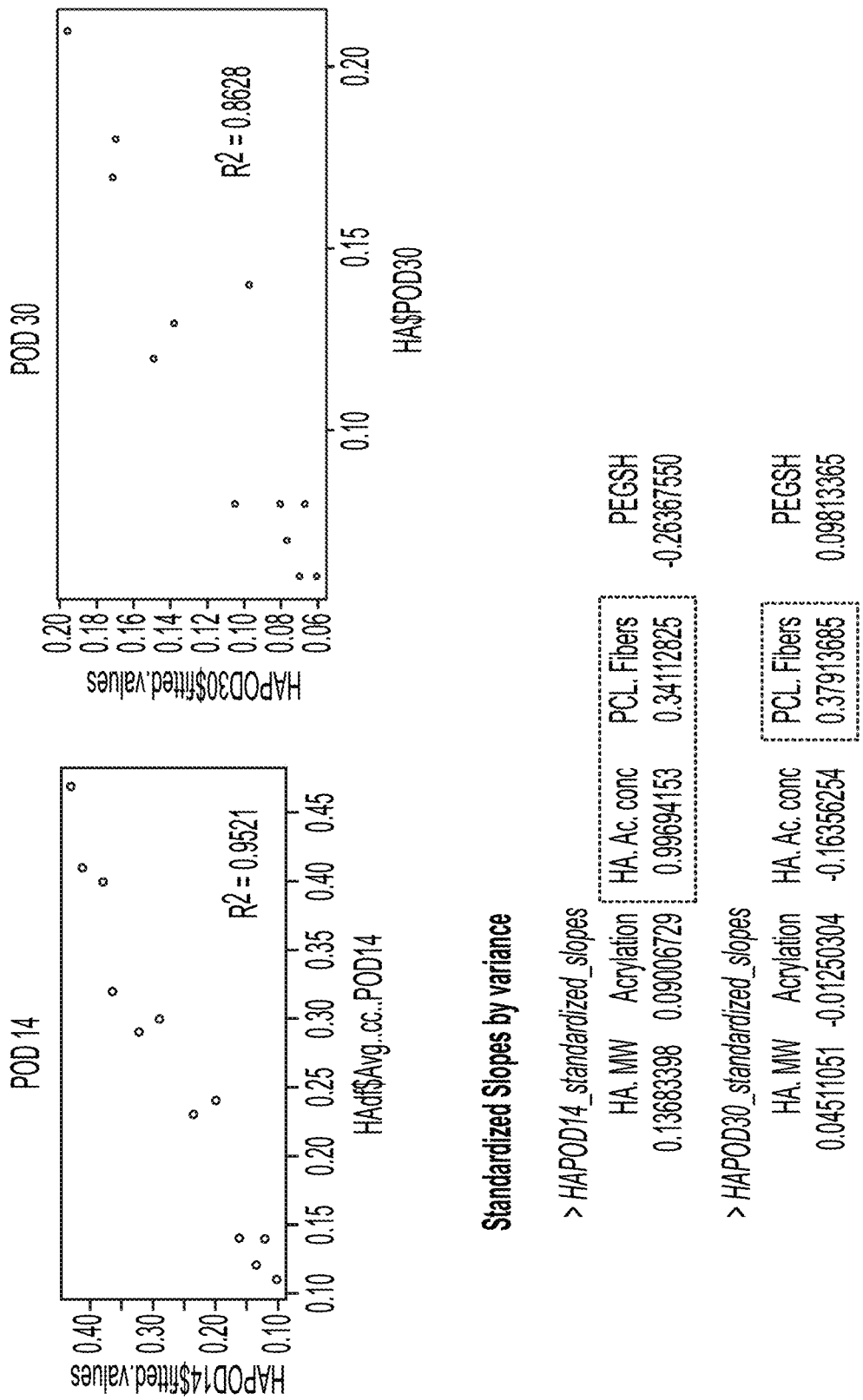

As shown in FIGS. 5A and 5B, five input parameters (hydrogel molecular weight, hydrogel modification degree, hydrogel concentration, nanofiber concentration, and crosslinking density) were altered because parameters for improvement of persistence and performance in vivo had yet to be determined. After collecting the data over a 78-day period (to date, study ongoing) the input parameters with the heaviest influence on volume retention were determined. As shown in FIG. 5C, the linear predictive capability of the linear regression models is acceptable at 14 and 30 days ($R^2$=0.95 and 0.86, respectively). The contributors to those linear models change over time. In the 14-day time frame, the hydrogel concentration was the largest input contributor. This is likely because the hydrogel swells in vivo, and thus the higher concentration gels caused more swelling than the lower concentration gels. Most interestingly, the nanofiber concentration had the biggest influence at 30 days post injection. Likely the fibers help guide the tissue ingrowth and are therefore critical for the extended volume retention seen in the best performing composite formulations.

Example 8. Swelling Assessment with MRI in Rat Model

The fully-reacted, particulated formulation of the LS series of the composite beads described above shows superior swelling properties when compared to commercial

TABLE 4

Characterization of LS-2 through LS-14 variants on the LS1 formulation

| # | HA-Ac MW (MDa) | Acrylation (%) | HA-Ac (mg/mL) | PCL Fibers (mg/mL) | PEGSH (mg/mL) | Storage Mod (Pa) |
|---|---|---|---|---|---|---|
| LS-1 | 0.7 | 10.0 | 7.0 | 10.0 | 7.2 | 121 |
| LS-2 | 0.7 | 19.0 | 7.0 | 10.0 | 7.7 | 222 |
| LS-3 | 1.5 | 23.0 | 7.0 | 10.0 | 11.7 | 191 |
| LS-4 | 1.5 | 23.0 | 15.0 | 10.0 | 24.0 | 627 |
| LS-5 | 1.5 | 23.0 | 15.0 | 30.0 | 25.7 | 2190 |
| LS-6 | 1.5 | 23.0 | 20.0 | 20.0 | 32.5 | 1259 |
| LS-7 | 2.7 | 15.3 | 7.0 | 10.0 | 6.0 | 186 |
| LS-8 | 2.7 | 15.3 | 7.0 | 20.0 | 8.9 | 281 |
| LS-9 | 2.7 | 15.3 | 7.0 | 30.0 | 12.3 | 386 |
| LS-10 | 2.7 | 15.3 | 15.0 | 30.0 | 18.0 | 1277 |
| LS-11 | 1.3 | 20.4 | 13.4 | 26.0 | 22.0 | 1273 |
| LS-12 | 1.3 | 20.4 | 17.4 | 18.0 | 27.4 | 984 |
| LS-13 | 1.3 | 20.4 | 17.4 | 18.0 | 27.4 | 984 |
| LS-14 | 1.5 | 23.0 | 10.0 | 20.0 | 16.0 | 546 |
| Voluma XC® | 2.5 | #N/A | 24.0 | #N/A | #N/A | 265 |
| Prevelle® | #N/A | #N/A | 7.0 | #N/A | #N/A | 195 |

F. Example 7. Evaluation of Tissue Ingrowth by MRI and Histological Analysis

Tissue ingrowth was characterized by MRI imaging and histological analysis (FIG. 5A-5B) in comparison with the Juvéderm Voluma filler. Due to differences in water content between the synthetic and host tissue as illustrated by the MRI analysis, the scaffold appears a bright white. Over time, subdermal fillers such as Juvéderm. Specifically, the significant post-procedure swelling observed with Juvedérm injection in the rodent MRI model is not seen with the LS composite, enabling more of a "what you see is what you get" appearance that is desired by clinicians. Continued optimization of HA concentrations, fiber loading, and crosslinking for the current particulated composite form is ongoing and are expected to restore comparable durability to existing commercial standards while retaining enhanced volumization, lessened swelling, and more natural feel. The degree of swelling has been characterized and plotted in FIG. 6A-C.

Tan δ quantifies the balance between energy loss and storage. A higher Tan δ indicates more liquid-like properties, whereas lower tan δ suggests more solid-like properties, regardless of the modulus or viscosity.

$$\text{Tan Delta}(\delta) = G''/G'$$

Figure 7A:
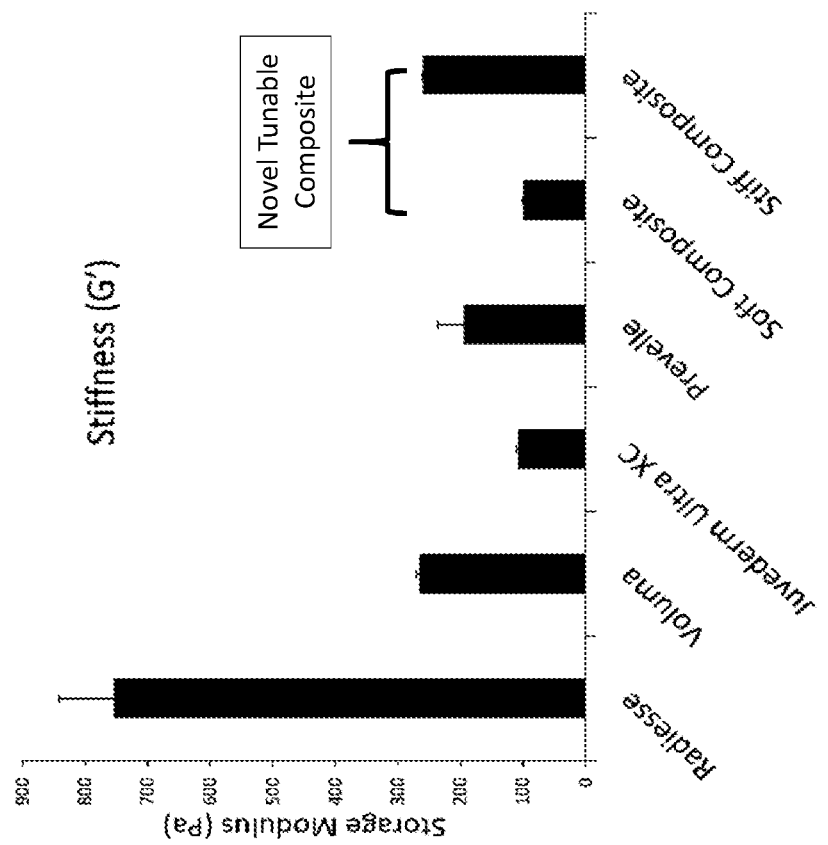
FIGS. 7A-7C are two graphs showing stiffness (FIG. 7A) and tan delta (FIG. 7B) for soft tissue injectables (quantifies the balance between energy loss and storage. A higher Tan δ indicates more liquid-like properties, whereas lower tan δ suggests more solid-like properties, regardless of the modulus or viscosity).
Figure 7B:
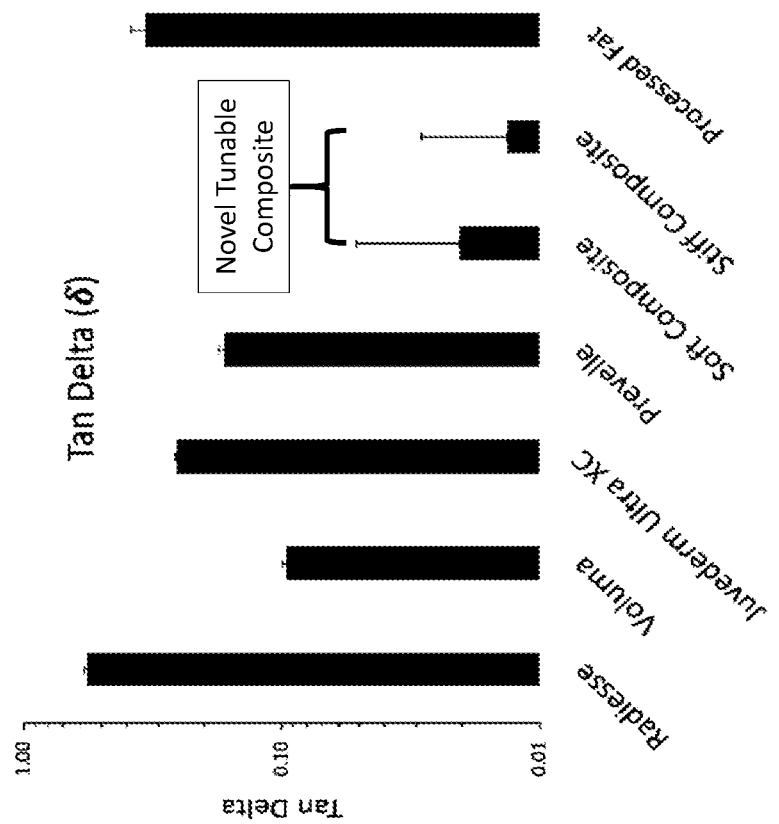
Figure 7C:
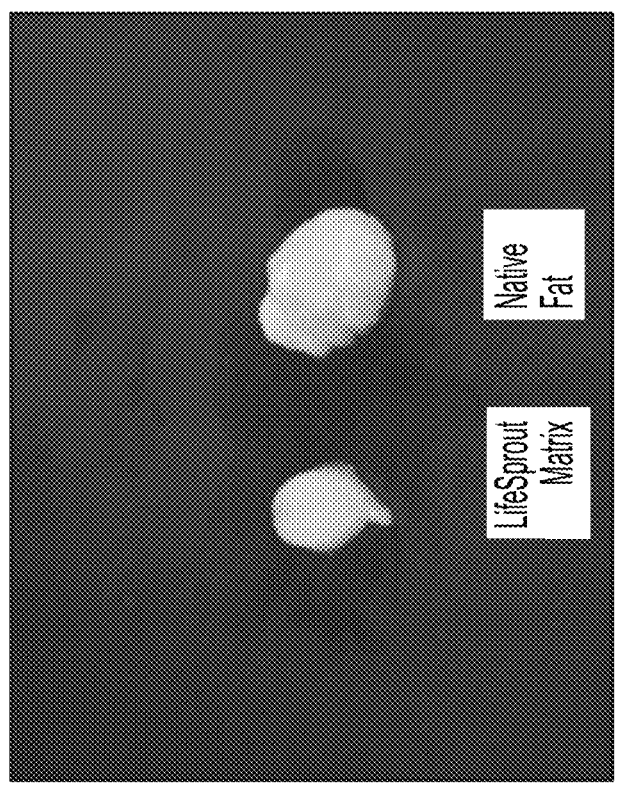
Figure 7C:
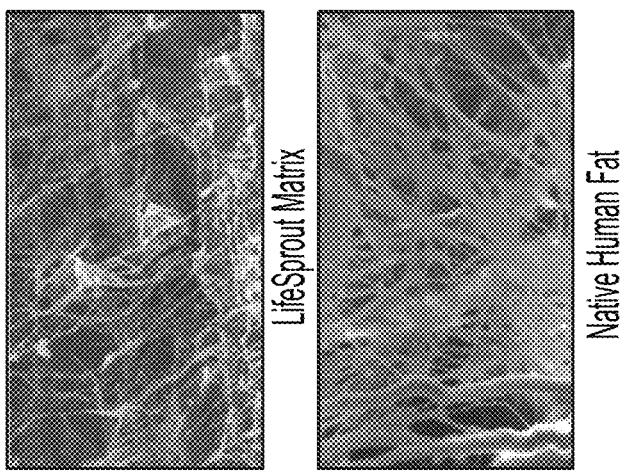

The LS beaded composite has lower tan δ measure (FIG. 7A) than marketed fillers while retaining a similar stiffness profile (FIG. 7B). The more solid-like properties reflect that of in vivo fat, the current gold standard for soft tissue reconstruction (FIG. 7C).

G

H. Example 9. Injectable Formulations Enabled by the Beaded Composite Design

Four potential injectable formulation are enabled with the beaded hydrogel design.

In one embodiment, the injectable formulation comprises vials of lyophilized powder cakes that are immediately reconstituted prior to injection. This is a workflow similar to that used in Botox injections.

In another embodiment, a two-syringe system is used to rehydrate the composite. Clinicians would connect the two syringes, rehydrate, and then immediately inject the formulation.

In another embodiment, a formulation for use with a single syringe is used, wherein the beads are rehydrated in the manufacturing facility during packaging and are ready to inject upon opening the package.

In another embodiment, a syringe containing lyophilized powder is provided along with a vial comprising reconstitution fluid. The fluid is drawn up from the vial and into the syringe to mix with the powder.

All four embodiments have shown promise in advanced development testing.

Example 10. Development of Lyophilization Method and Formulation

A major advantage of the composite structure described in the Examples above is that the mechanical properties of the nanofiber phase of the fiber-hydrogel composite changes little in the dried or frozen state, as opposed to most hydrogel components known in the art. Thus, during freezing or lyophilization, the fiber fraction can help maintain the overall composite microstructure. With the correct lyophilization cycle and formulation, the composite can be lyophilized, while still remaining as distinct beads upon rehydration.

Figure 8A:
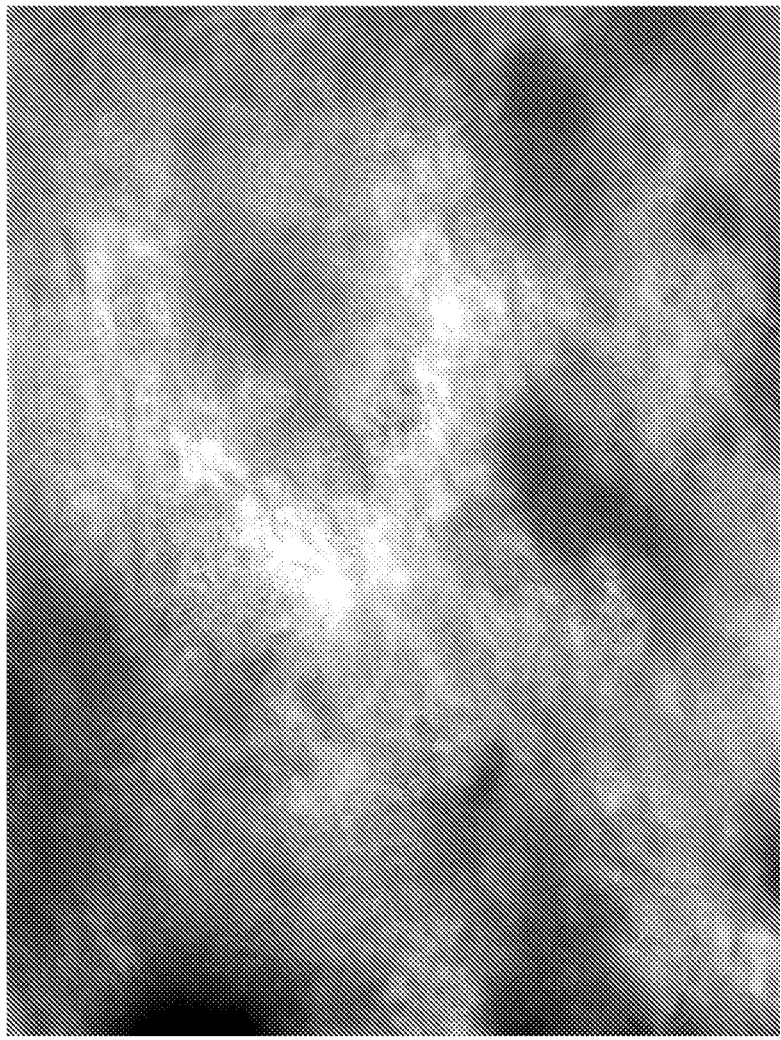
FIGS. 8A-8D depict development of a lyophilized form of the beaded composite.
Figure 8B:
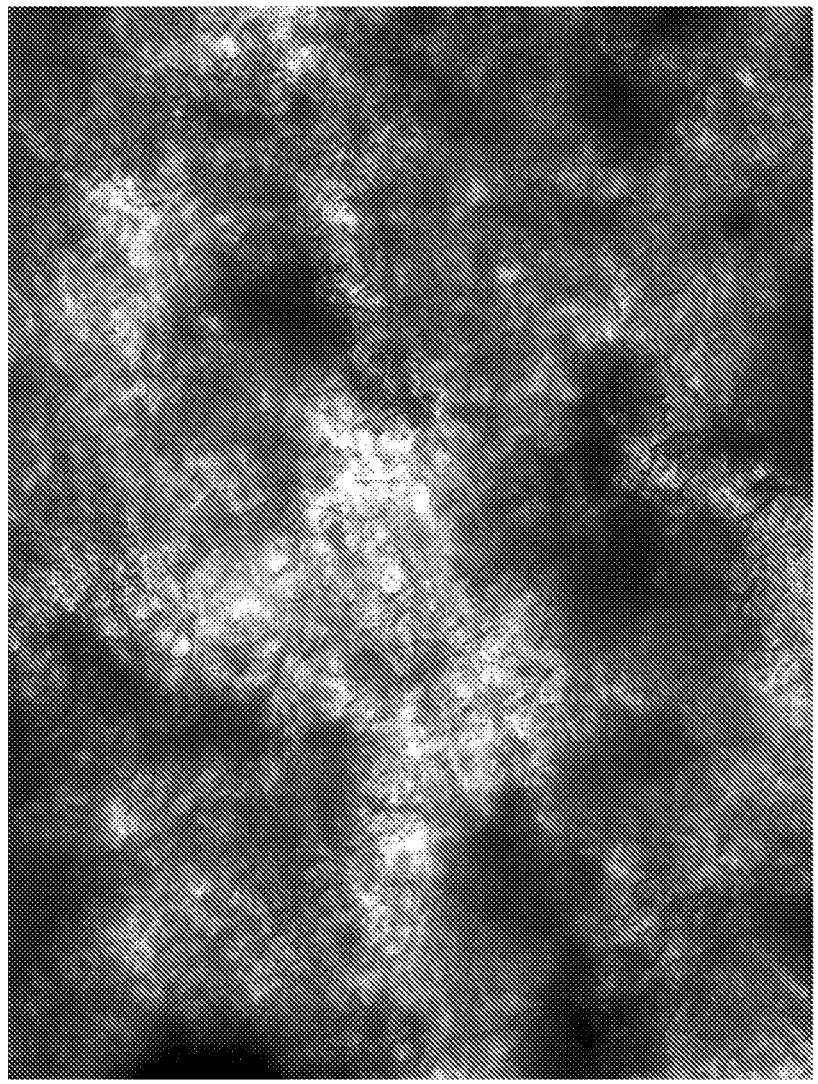
Figure 8C:
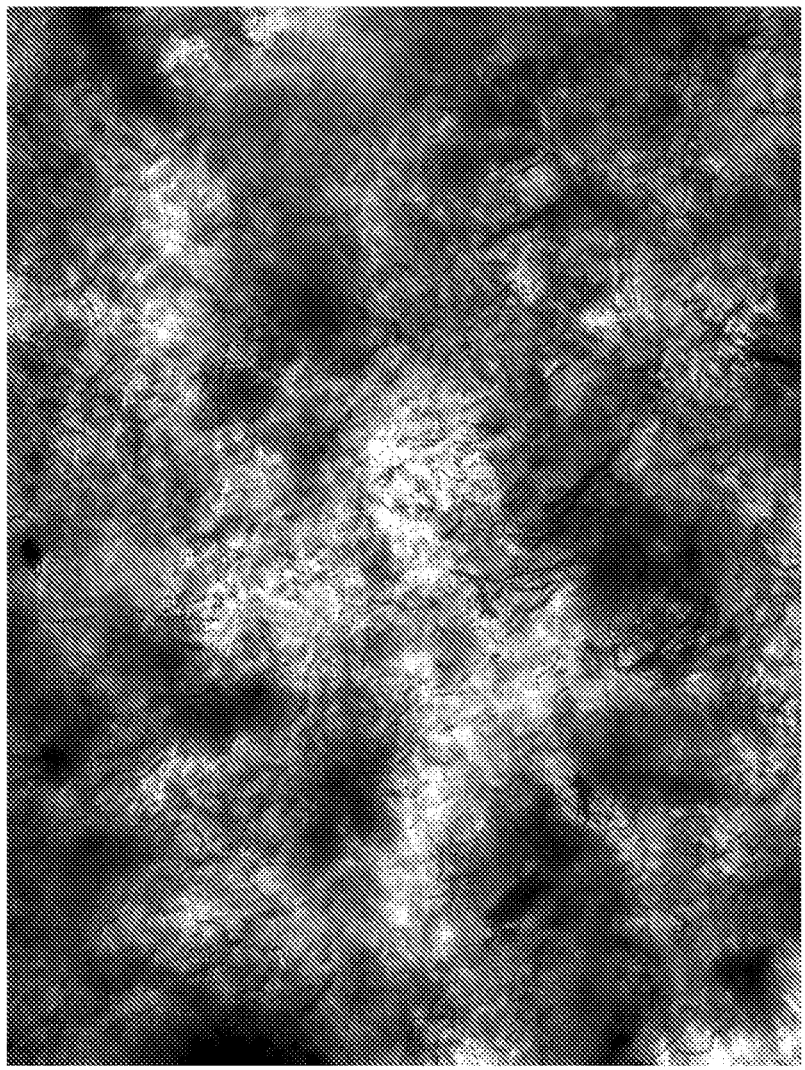
Figure 8D:
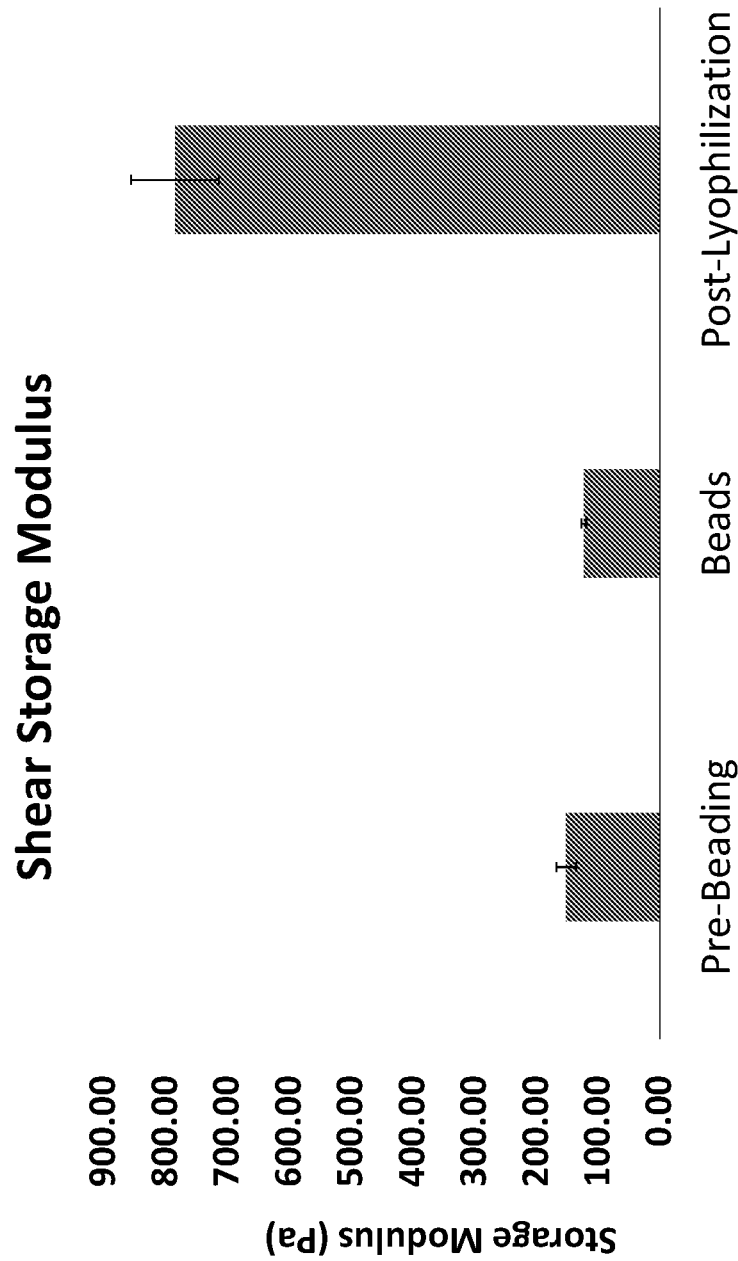

Even with the composite structure, the ideal lyophilization formulation and process need to be determined experimentally. In this Example, 7.3 mg/mL 700 kMW HA-Acrylate, 10 mg/mL nanofibers and 8.18 mg/mL PEGSH (5k 2-arm) formulated in PBS reacted overnight in a 5 cc syringe in the 37° C. incubator. 145 µL of the solution is also added to three 8 mm diameter molds for rheology testing (FIG. 8A, "Pre-beading" in FIG. 8D). After gelling, the composite gel is made into beads by forcing the gel through a 250 µm screen. The beads are injected into three 8 mm diameter molds and immediately tested for rheology (FIG. 8B, "Beads" group in FIG. 8D). The remaining bead volume were snap frozen in liquid nitrogen and lyophilized on a Labconco® flask lyophilizer (FreeZone® 6) for 48 hours. After lyophilization, the lyophilization cake was smaller than the frozen solution volume, indicating the sample did not remain frozen for the entire duration. The beads were rehydrated to exactly replace the water mass lost (as measured by weight). The resulting reconstituted gel had different properties than before lyophilization—the gel was biphasic with an excess water phase that wasn't fully absorbed by the gel phase. The gel also could not be loaded into a syringe via aspiration because the microstructural changes had fused the individual beads together. When tested for rheology (FIG. 8C, "Post-Lyophilization" group in FIG. 8D) the gels were far stiffer, with a storage modulus 5.19-times higher than the pre-beaded gel and 6.39-times higher than the beaded gel. This is caused by the diffuse hydrogel structure collapsing into a denser biphasic structure. The injectability, the physical properties, and the porosity are all affected by the lyophilization process.

Example 11. Development of Improved Lyophilization Method and Formulation

Figure 9A:
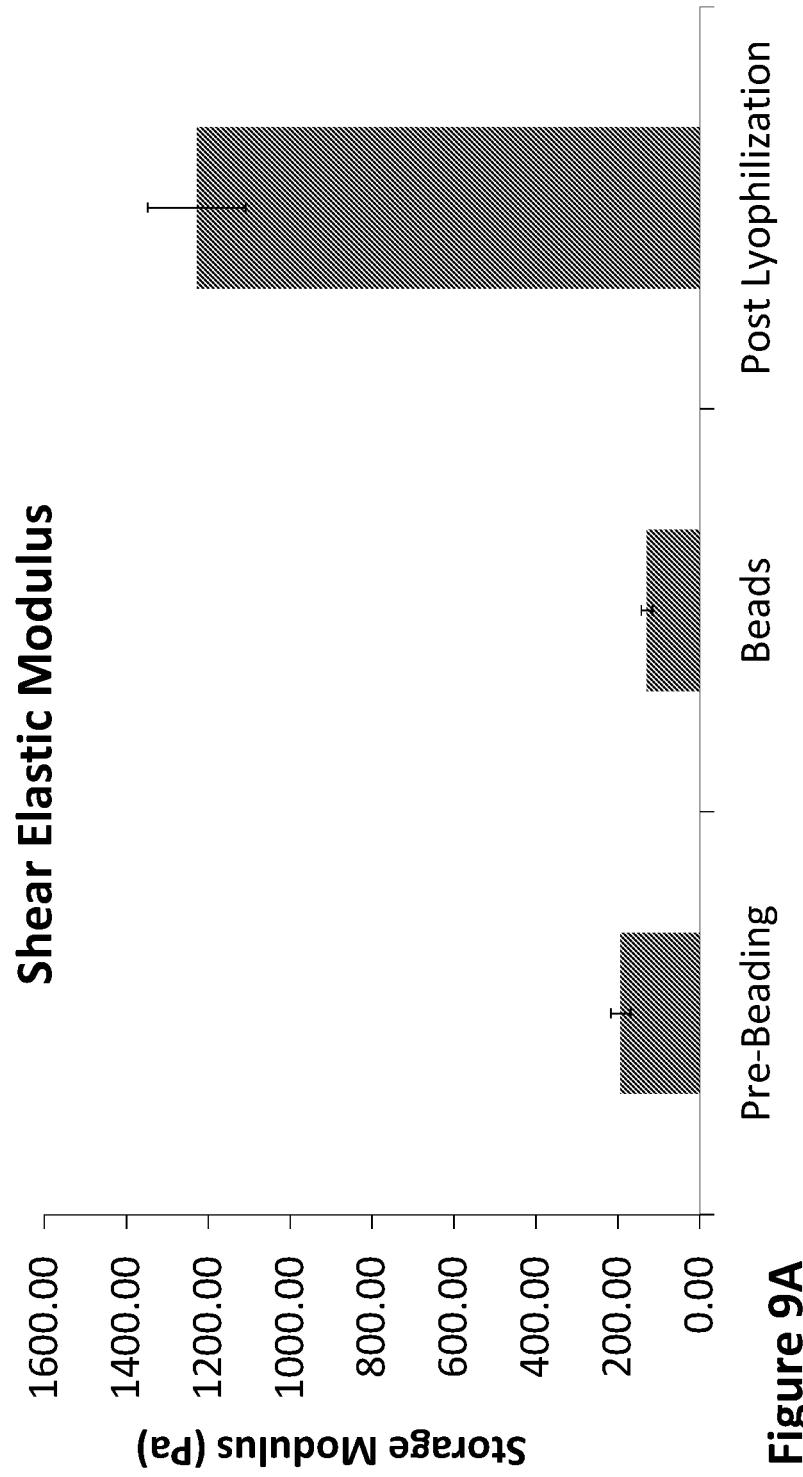
FIGS. 9A-9B are two graphs showing shear elastic moduli (FIG. 9A) and compression elastic moduli (FIG. 9B) for pre-beading, beaded, and post-lyophilization samples of the improved lyophilization process.
Figure 9B:
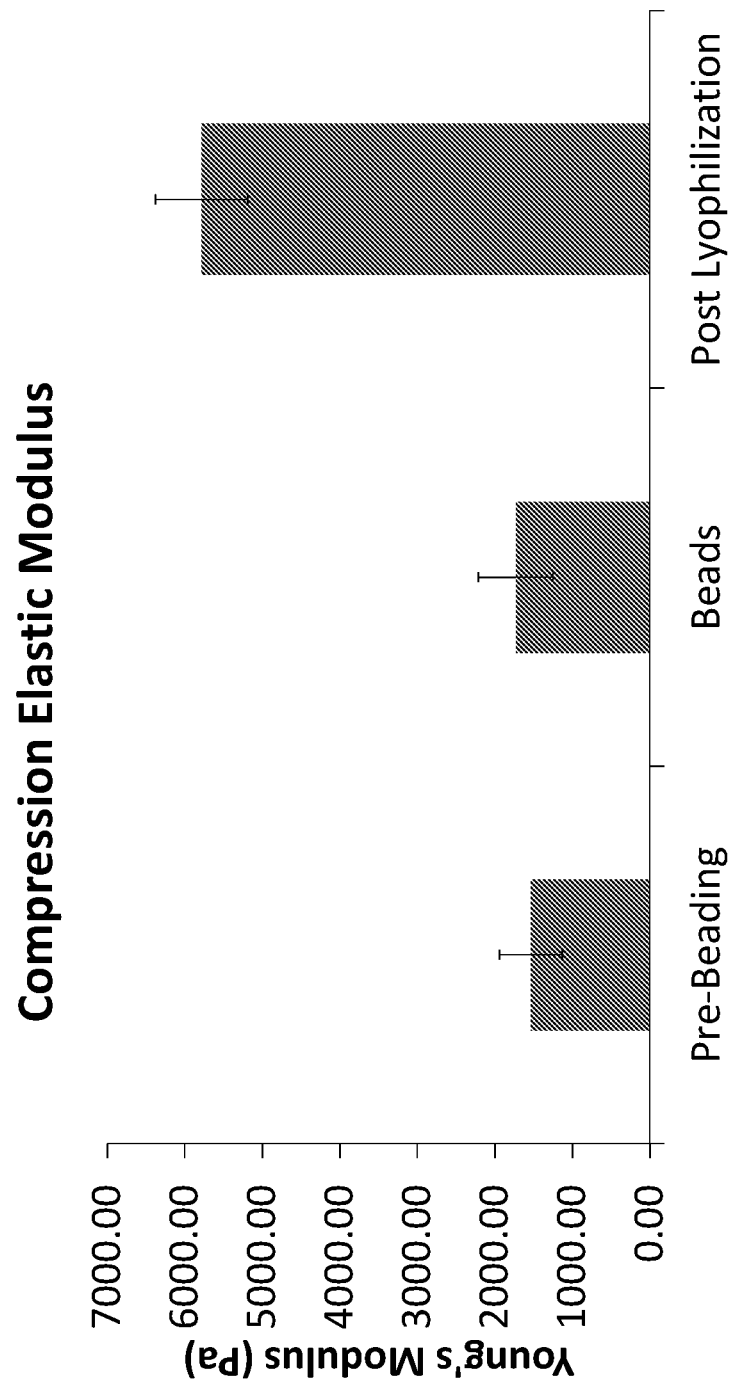

The identical procedure was followed again as described above, but with more control over lyophilization, using an in-shelf lyophilizer in order to keep the lyophilizing sample colder (below the glass transition temperature of the frozen sample) during the lyophilization process. 7.3 mg/mL 700 kMW HA-Acrylate, 10 mg/mL nanofibers and 8.18 mg/mL PEGSH (5k 2-arm) formulated in PBS reacted overnight in a 5-cc syringe in the 37° C. incubator. 145 µL of the solution is also added to three 8 mm diameter molds for rheology testing ("Pre-beading" in FIG. 9A-B). After gelling, the composite gel is made into beads by forcing the gel through a 250 µm screen. The beads are injected into three 8 mm diameter molds and immediately tested for rheology ("Beads" group in FIG. 9A-B). The remaining bead volume was frozen in a −80° C. incubator then placed in pre-cooled Labconco® Triad® lyophilizer for 24 hours at a shelf temperature of −10° C. followed by secondary drying for 24 hours at 20° C. After lyophilization, the lyophilized cake occupied the same volume in the vial as the frozen sample before lyophilization, indicating the cake did not begin to melt during lyophilization. The beads were rehydrated to exactly replace the water mass lost (as measured by weight). The reconstituted gel could not be loaded into a syringe via aspiration, but when passed between syringes with a luer-lock connector, the gel beads that were initially stuck firmly to one another were able to be dispersed into individual beads. When tested for rheology ("Post-Lyophilization" group in FIG. 9A-B), the beads were far stiffer, with greatly increased Storage Moduli and Young's Moduli. This is caused by the diffuse hydrogel structure collapsing into a denser biphasic structure. The injectability, the physical properties, and the porosity are all affected by the lyophilization process.

Example 12. Development of Lyophilization Method with Hypotonic Formulation 7.0 mg/mL 700 kMW HA-Acrylate, 10 mg/mL nanofibers and 7.18 mg/mL PEGSH (5k 2-arm) reacted overnight in a 5 cc syringe in the 37° C. incubator then beaded with a 150-µm or 250-µm screen. In this Example, the beads were formulated as hypotonic (deionized water used instead of PBS).

Figure 10A:
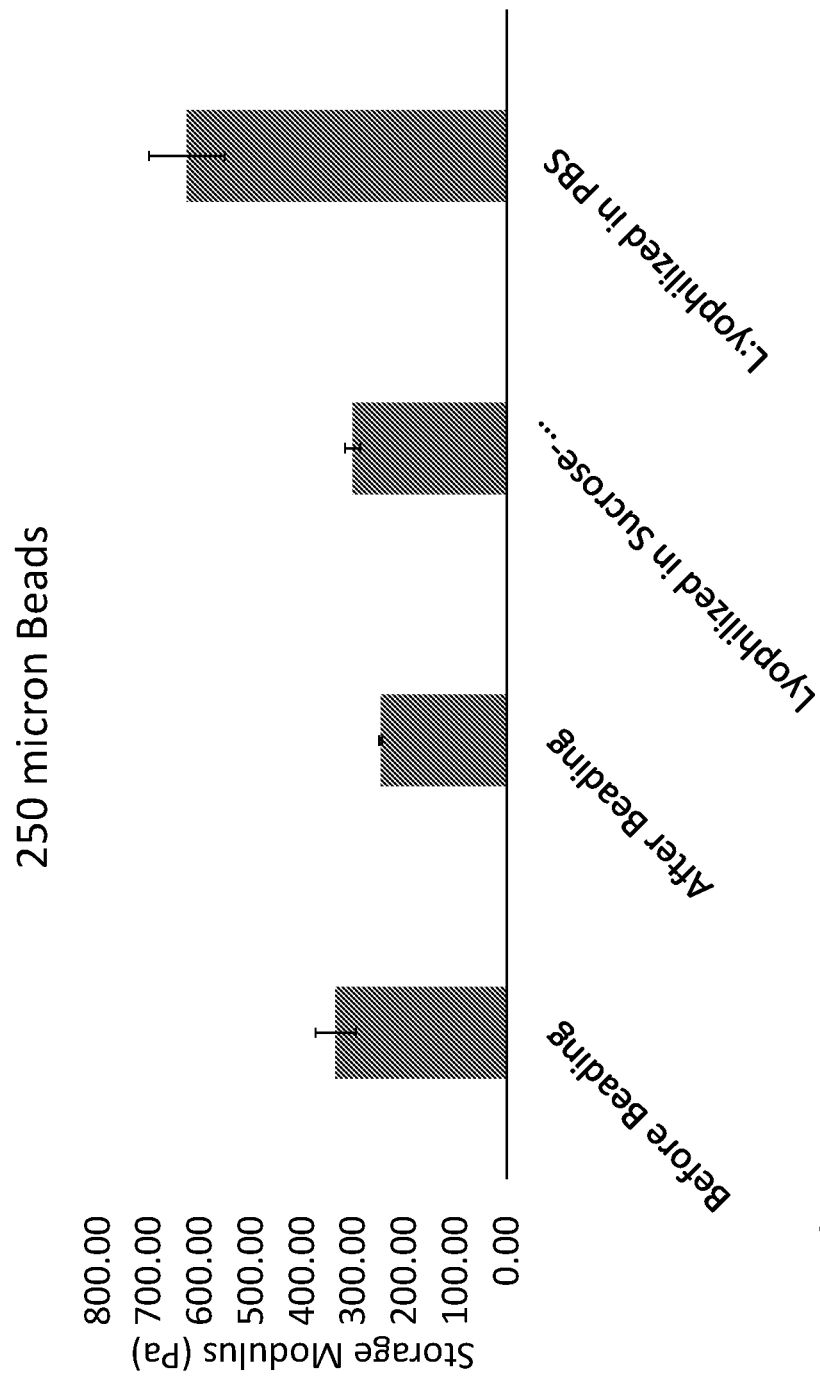
FIGS. 10A-10D are a series of graphs showing development of a lyophilization method using hypotonic formulation.

1 cc of the beads are loaded into Labconco® lyophilization vials, to which 1 cc of isotonic solution is added and further 1 cc of deionized water is added to have a total solution volume of 3 cc in the vial, with the beads dispersed throughout the volume. The isotonic solution was either A: 3% sucrose, 3% trehalose, 0.3% NaCl and 2 mg/mL free 700k HA or B: PBS with 2 mg/ml free 700k HA. The vials are snap frozen in liquid nitrogen, then lyophilized at −30° C. shelf temperature and 10 Pa vacuum pressure for 48 hours, with 24 hours of secondary drying with the temperature raised to 20° C. in a Labconco Triad in-shelf lyophilizer. After lyophilization, the beads were rehydrated to exactly replace the water mass lost (as measured by weight). The composite gel beads could be easily aspirated into a syringe, indicating that the individual bead structure was preserved, which was confirmed by optical microscope. The group lyophilized in the sucrose-trehalose solution had identical feel and handleability as the group did immediately after the beading process, before the dilution and lyophilization. The rheological properties were virtually identical as well, with the group having the storage modulus of 90% of the initial pre-beading gel, and 22% higher modulus than the beaded gel prior to lyophilization (FIG. 10A). The group diluted in PBS buffer was also easily aspirated into the syringe and behaved similarly to the sucrose-trehalose group but had a raised storage modulus that was 87% higher than the initial, pre-beaded modulus and 154% higher than the beaded gel prior to lyophilization. This indicates that some microstructure changes were still occurring in the PBS group, even if the particles remained as distinct beads.

Bead Sizing

The bead sizes were varied by varying the mesh size of the screens used in the beading process.

Figure 10B:
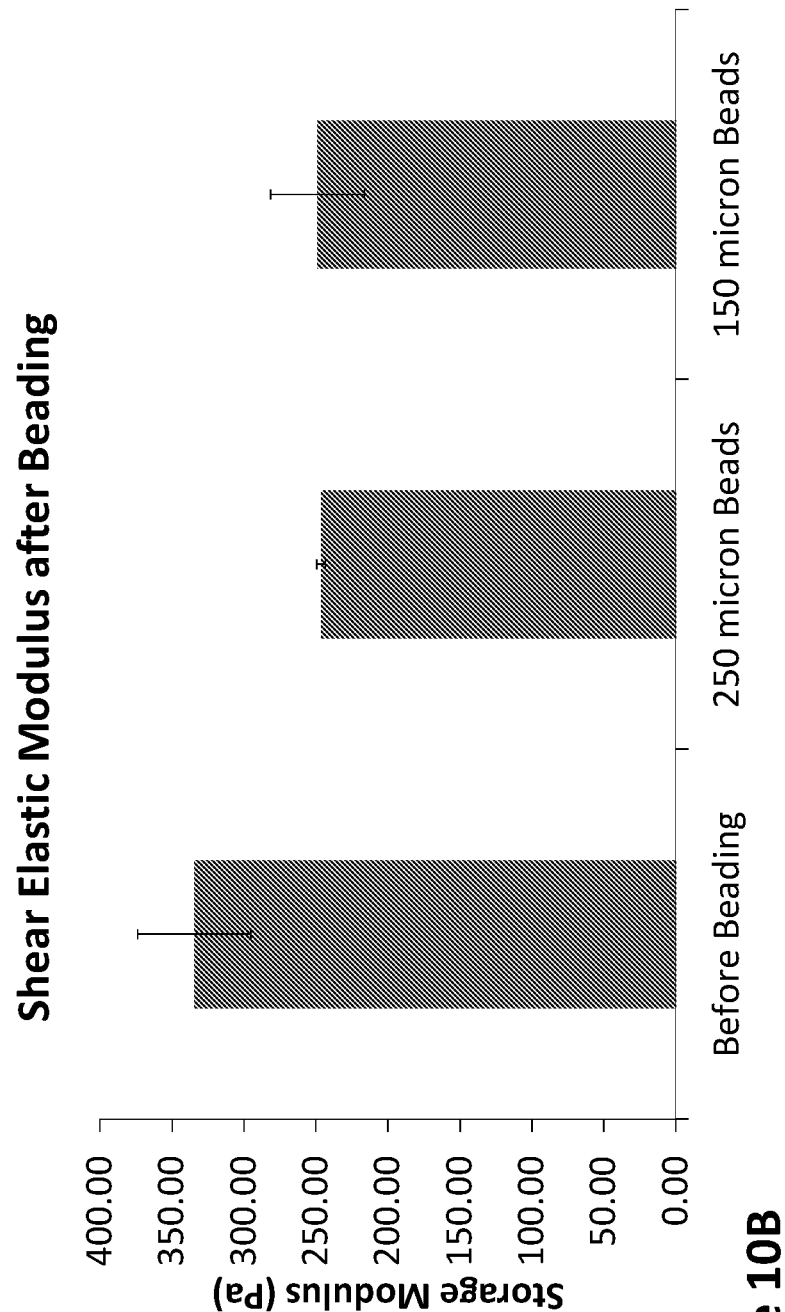

Bead screens with openings over 250 μm were excluded, since the resulting beads need to have at least one dimension that is sized smaller than the inner diameter of the syringe needle. The needles commonly used for dermal filler applications range from 25-gauge to 30-gauge, with an inner diameter of from 260 μm to 160 μm. Smaller beads were attempted via a screen with 90-μm openings, but the small mesh size disrupted the composite gel microarchitecture; the 90-μm opening size was smaller than the length of many of the individual fibers, which caused the fibers and gel to be ripped apart, instead of being cut into homogenous gel-fiber composite. The processing with a 90-μm screen did not produce enough material for characterization. The beads produced by the 250-μm and 150-μm screens (FIG. 10B) produced gels with similar rheological properties to beads formed as in FIG. 10A, especially storage modulus and tan delta, appropriate for dermal fillers.

Tan Delta

Figure 10C:
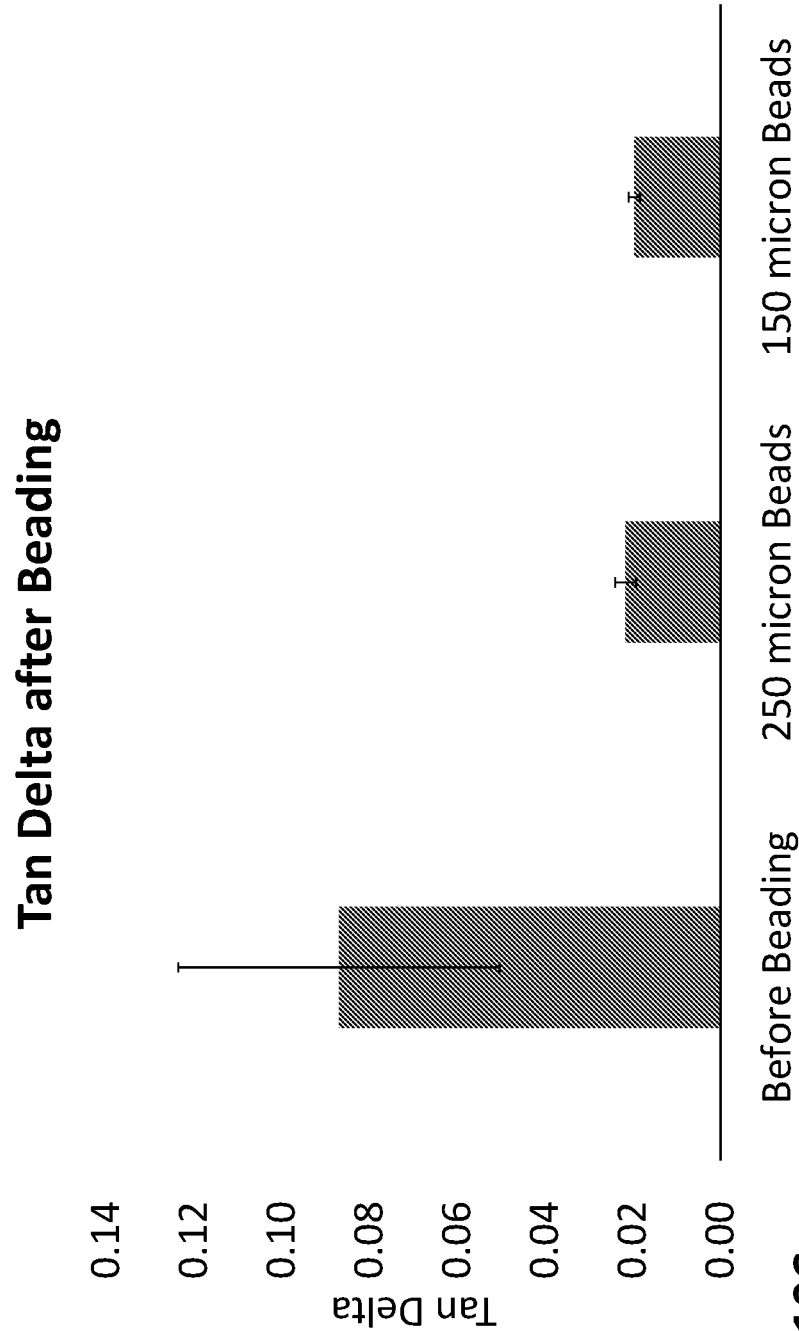
Figure 10D:
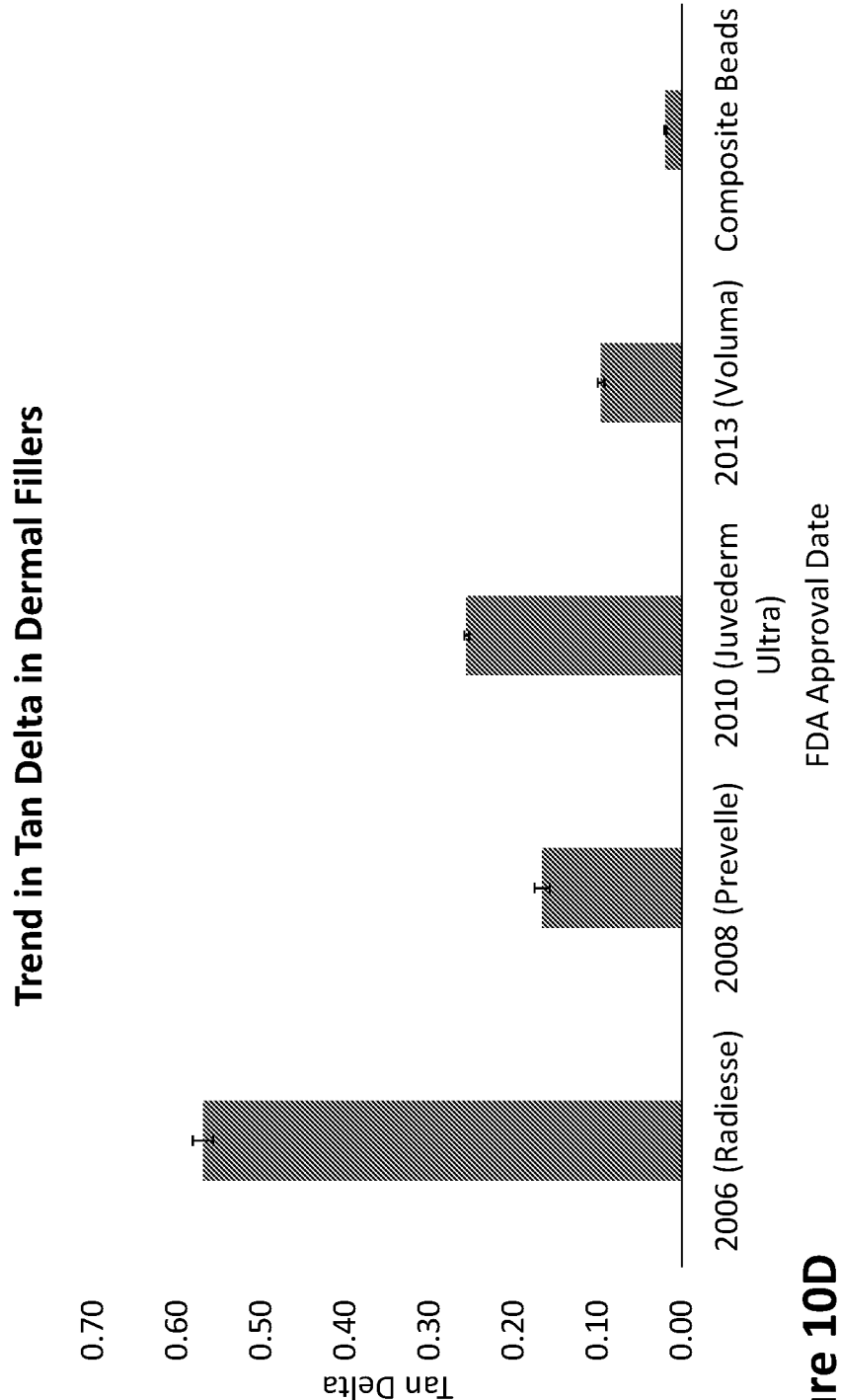

The tan delta is the rheological loss modulus divided by the storage modulus, which means that a lower tan delta number equates to a more "solid-like" as opposed to "liquid-like" material. The tan delta for samples the process described above (before beading, 250-μm beads, 150-μm beads) is shown in FIG. 10C. As seen in the trend illustrated in FIG. 10D, the dermal filling industry has been trending toward lower tan delta values over time. This is a trend toward a more solid-like feel, which has a better lifting capacity for filling a skin defect. The fiber-hydrogel composite material furthers that trend towards better lifting capacity and maintains that trait even after the beading process. The tan delta data were obtained during an amplitude sweep at 1 Hz from 0.1-10% amplitude, averaging the tan delta values from 1-10% amplitude on Ares G2 rheometer. Composite value is from the 150-μm bead group shown in FIG. 10C.

Example 13. Synthetic Soft Tissue Via Cell Delivery

Large Animal Soft Tissue Defect Model

The previous Examples have examined efficacy and host tissue response following subdermal injection models, as these are most relevant for the subdermal filler product disclosed therein. To further develop the uses of this technology, restoration of larger soft tissue defects for reconstructive surgery is explored.

Figure 11A:
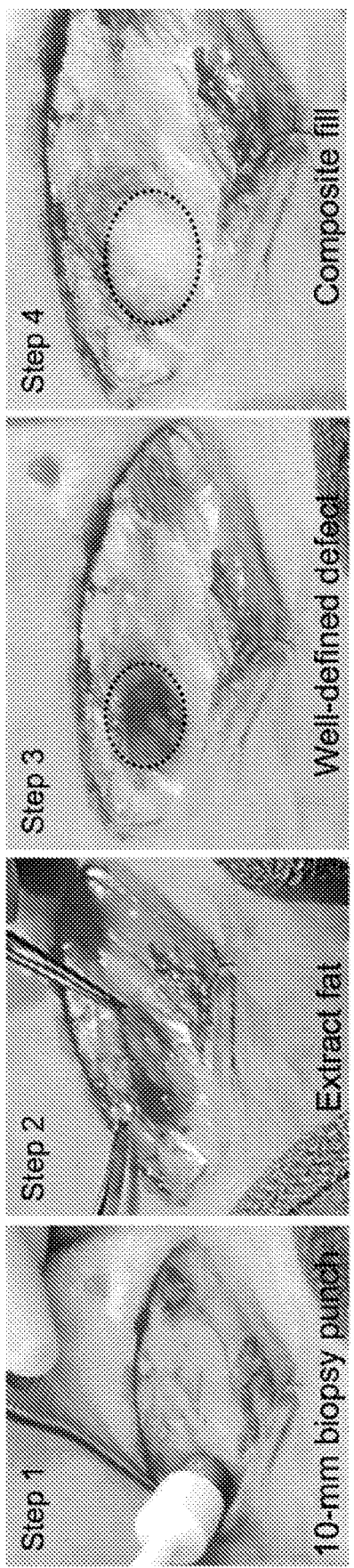
FIG. 11A-11B show a method for synthetic soft tissue generation.

A moderately-sized defect (cylinder: φ-10 mm×h-13 mm; ~1-cc) was generated in the inguinal fat pad of the New Zealand rabbit using a 10-mm biopsy punch, and a saline displacement method was used to ensure consistency in volume of the removed fat in different animals. The 1 cc volume is larger than the bolus size of individual fat grafts used currently for soft tissue restoration and serves as a relevant proof of concept. The in situ-forming and beaded composite, or control hydrogels which assumed the defect shape (FIG. 11A).

Figure 11B:
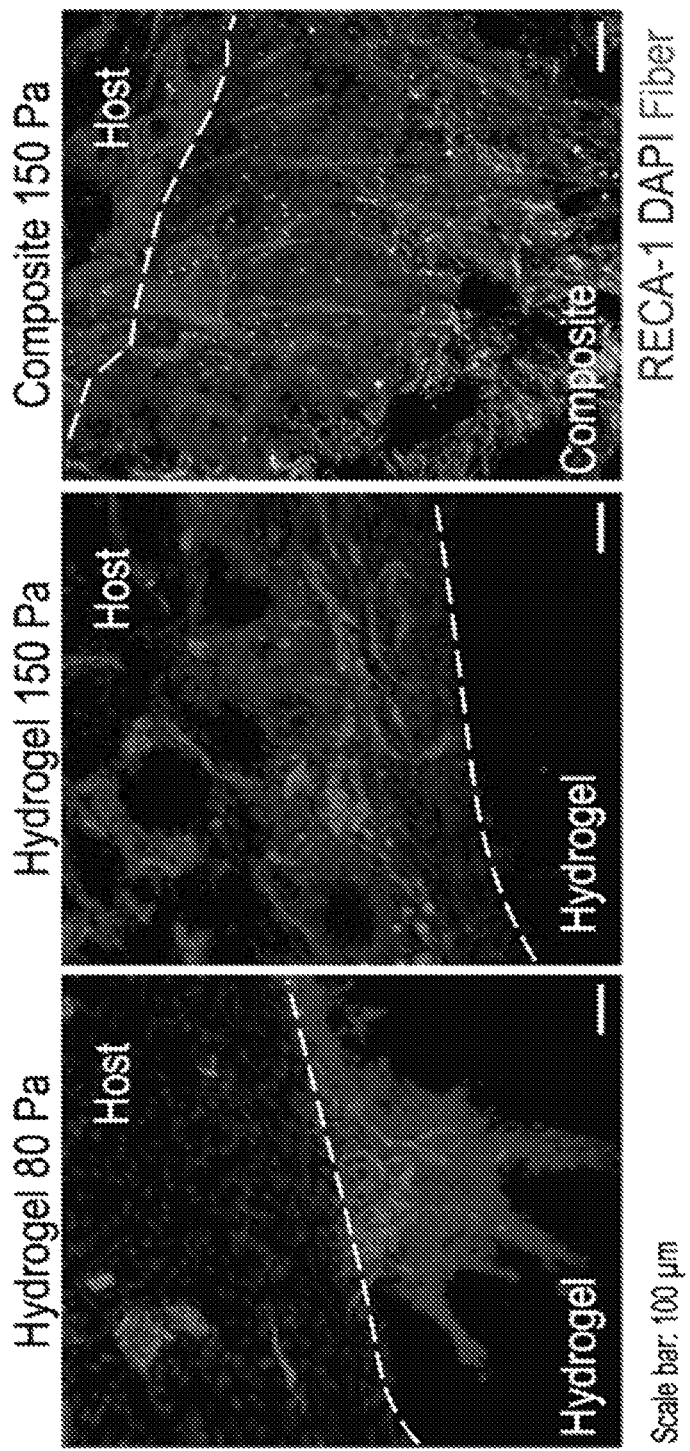

A preliminary survey of the tissue samples harvested on POD14 (post-operative day 14) confirmed that host blood vessels infiltrated into the 150-Pa composite more substantially than into the 80-Pa hydrogel on POD 14. In contrast, 150-Pa hydrogel did not show significant vessel ingrowth into the graft; and there appeared to be a clear boundary between the 150-Pa hydrogel and the host tissue. In this pilot investigation, stem cells were not seeded into the composite nor autologous fat grafting mixed into the composite. The results demonstrate vascular ingrowth into the composite alone. This will also be the model that is used going forward with larger volume soft tissue reconstruction with the incorporation of cells. FIG. 11B shows host blood vessel infiltration into different graft matrices (150-Pa composite, 150-Pa hydrogel, and 80-Pa hydrogel) on POD 14. Endothelial cells were stained with CD31 in red and cell nuclei were stained with DAPI in blue. Fibers were F8BT-labelled in green. Scale bar: 100 μm.

The study highlighted below demonstrates progress in restoring larger, deeper soft tissue defects in a large animal trauma model.

Example 14. Subdermal Implantation of the Composite Beads in Rat Model

Tissue samples were harvested at 13 weeks in vivo from a rat with LS-5 composite beads from the experiment in Example 5. The tissue samples were fixed, sectioned, and stained with H & E and Masson's Trichrome stains. The H & E-stained histology image (FIG. 12) shows the growth/infiltration pattern of the cells, which recapitulate the underlying bead morphology.

In alternative embodiments, various composite beads with different fiber density are implanted to evaluate cell proliferation, morphological changes, migration behavior.

Example 15. Stability Determination of Composite Beads

To evaluate the stability of the disclosed composite beads, rheological studies are performed on microbeads at various time points to determine mechanical stability. In hydrated form at 4° C., the microbeads were determined to be stable for 6 months.

Rheological tests (shear modulus) to determine structural integrity are performed at room temperature at 1 month, 3 months, 6 months, 9 months, 12 months and 24 months on hydrated form, and dehydrated form of the beads. Various composite beads with different hydrogel molecular weight, acrylation degree, fiber concentration, maleimide degree, and cross-linking density are tested for their stabilites.

As described in the Examples above, the beaded formulation remains easily injectable through clinically-relevant 27- to 31-gauge or 16- to 31-gauge needles and offers several improvements over the in situ gelling prototype. The beaded formulation enables a single syringe delivery system for improved ease of use. With much greater surface area, the lyophilized beads rehydrate more quickly, so extensive two-syringe mixing will no longer be required. The beaded formulation enables higher concentrations of hyaluronic acid, nanofibers, and crosslinker to be used in the formulation. Previously, the maximum concentrations were governed by viscosity and injection force. By moving to particularized beads, the constituent concentrations are no longer rate limiting and the team can further modify stiffness and enhance durability. The beaded formulation enables enhanced stability. The pre-reacted, beaded form of the composite is much more robust to temperature, humidity, and light variation than the unreacted form, and has had no change in properties after multiple cross-country shipments. Lastly, the beaded formulation provides an enhanced cell and tissue delivery scaffold.

EQUIVALENTS

It is understood that the detailed examples and embodiments described herein are given by way of example for illustrative purposes only, and are in no way considered to be limiting to the invention. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present invention will be apparent from the appended claims. Moreover, those skilled in the art will recognize, or be able to ascertain using no more than routine experimentation, many equivalents to the specific embodiments of the invention described herein. Such equivalents are intended to be encompassed by the following claims.

The invention claimed is:

1. An injectable population of substantially non-spherical microbeads comprising a functionalized hyaluronic acid network covalently linked to a plurality of polycaprolactone fibers having a mean length of less than about 200 micrometers and the diameter of the polycaprolactone fibers is within a range of about 100 nanometers to about 5 micrometers, and a reacted crosslinking agent present prior to crosslinking at a concentration from about 1 mg/mL to about 25 mg/mL,
   wherein the mean size of the non-spherical microbeads is within the range of about 50 micrometers to about 300 micrometers along the longest dimension,
   wherein the microbeads are substantially stable at room temperature for at least about 6 months,
   wherein the functionalized hyaluronic acid network, plurality of polycaprolactone fibers and crosslinking agent are reacted prior to injection or storage.

2. The microbeads of claim 1, wherein the microbeads are injectable through a 16- to 31-gauge needle.

3. A kit comprising a syringe comprising the microbeads of claim 1, wherein said microbeads are formulated during storage as i) substantially dehydrated beads or ii) hydrated beads that are ready for injection into a target tissue of a subject, wherein the dehydrated microbeads are suitable for reconstitution with water, saline solution or suitable reconstitution fluid to substantially replace the water mass lost (as measured by weight) prior to injection into a target tissue of a subject such that when the water mass lost is replaced to form the population of microbeads of claim 1, the concentration of the microbeads in the reconstitution fluid is the same or substantially the same as the concentration of microbeads before lyophilization.

4. The microbeads of claim 1, wherein the functionalized hydrogel network comprises reacted acrylated hyaluronic acid and thiolated poly(ethylene glycol).

5. The microbeads of claim 1, wherein the functionalized the functionalized hydrogel network comprises thiolated hyaluronic acid, and the crosslinking agent comprises poly(ethylene glycol) diacrylate (PEGDA), or a derivative thereof.

6. The microbeads of claim 1, comprising a plurality of pores, wherein pores are disposed throughout the hyaluronic acid network such that it promotes tissue growth and cell infiltration when administered into a target tissue of a subject.

7. The microbeads of claim 1 further comprising a compound selected from the group consisting of growth factors, compounds stimulating angiogenesis, immunomodulators, inhibitors of inflammation, and combinations thereof.

8. The microbeads of claim 1 further comprising a compound that have therapeutic effects, vascularization effects, anti-vascularization effects, anti-inflammatory effects, anti-bacterial effects, antihistamine effects, and combinations thereof.

9. The microbeads of claim 1 further comprising a processed tissue extracellular matrix, wherein the processed tissue extracellular matrix is derivable from an adipose tissue.

10. An implantable or injectable biomaterial comprising the population of microbeads of claim 1, wherein the biomaterial is formulated for dermal or subdermal administration into a target tissue of a subject.

11. The microbeads of claim 1 wherein the microbeads comprise a plurality of pores.

12. A formulation comprising the population of microbeads of claim 1, wherein the microbeads are lyophilized to form a population of dehydrated microbeads during storage, and wherein the dehydrated microbeads are suitable for reconstitution with water, saline solution or suitable reconstitution fluid to substantially replace the water mass lost (as measured by weight) such that when the water mass lost is replaced to form the population of microbeads, the concentration of the microbeads in the reconstitution fluid is the same or substantially the same as the concentration of microbeads before lyophilization.

13. A kit comprising the population of microbeads of claim 1 for administration into a target tissue of a subject, the kit comprising: a vial containing the microbeads, said microbeads having been lyophilized and formed into powder cakes, wherein the lyophilized powder cakes are able to be reconstituted by water, saline solution or suitable reconstitution fluid to form the population of microbeads.

14. A kit comprising the population of microbeads of claim 1 for immediate injection into a target tissue of a subject, the kit comprising: (i) a syringe comprising the microbeads formulated as lyophilized microbeads; and (ii) a vial comprising water, saline solution or suitable reconstitution fluid, wherein water, saline solution or suitable reconstitution fluid is capable of being drawn up from the vial into the syringe, whereby the lyophilized microbeads are rehydrated to form the population of microbeads.

15. A kit comprising the population of microbeads of claim 1 for immediate injection into a target tissue of a subject, the kit comprising: (i) a syringe comprising the microbeads formulated as lyophilized gel beads; (ii) a syringe comprising water, saline solution or suitable reconstitution fluid, wherein water, saline solution or suitable reconstitution fluid is capable of being drawn up from the vial into the syringe, whereby the lyophilized microbeads are rehydrated to form the population of microbeads of claim 1; and (iii) a luer connector, wherein the two syringes are capable of connecting with each other through luer connector.

16. A population of substantially non-spherical microbeads for administration to a subject comprising:
a functionalized hyaluronic acid network covalently linked to a plurality of polycaprolactone fibers having a mean length of less than about 200 micrometers and the diameter of the polycaprolactone fibers in within a range of about 100 nanometers to about 5 micrometers, and a reacted crosslinking agent present prior to crosslinking at a concentration from about 1 mg/mL to about 25 mg/mL,
wherein the mean size of the non-spherical microbeads is within the range of about 50 micrometers to about 300 micrometers along the longest dimension,
wherein the microbeads are substantially stable at room temperature for at least about 6 months,
wherein the functionalized hyaluronic acid network, plurality of polycaprolactone fibers and crosslinking agent are reacted prior to administration or storage.

17. The microbeads of claim 16 further comprising one or more compounds that have therapeutic effects, vascularization effects, anti-vascularization effects, anti-inflammatory effects, anti-bacterial effects, antihistamine effects, and combinations thereof.

18. The microbeads of claim 16 comprising a plurality of pores, wherein pores are disposed throughout the hyaluronic acid network such that it promotes tissue growth and cell infiltration when administered into a target tissue of a subject.

19. The device of claim 8, wherein the functionalized hydrogel network comprises acrylated hyaluronic acid, and the crosslinking agent comprises thiolated poly(ethylene glycol).

20. The microbeads of claim 16 wherein the functionalized hydrogel network comprises thiolated hyaluronic acid, and the crosslinking agent comprises poly(ethylene glycol) diacrylate (PEGDA).

* * * * *

SEQUENCE LISTING

```
<160> NUMBER OF SEQ ID NOS: 2

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Cys Cys Arg Arg Ile Lys Val Ala Val Trp Leu Cys
1               5                   10

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Gly Gly Gly Ser
1               5
```